US008613923B2

(12) United States Patent
Pfeifer et al.

(10) Patent No.: US 8,613,923 B2
(45) Date of Patent: Dec. 24, 2013

(54) MONOCLONAL ANTIBODY

(75) Inventors: Andrea Pfeifer, St-Légier (CH); Maria Pihlgren, St. Sulpice (CH); Andreas Muhs, Pully (CH); Ryan Watts, San Mateo, CA (US)

(73) Assignees: AC Immune S.A., Lausanne (CH); Genentech, Inc., South San Francisco, CA (US)

( * ) Notice: Subject to any disclaimer, the term of this patent is extended or adjusted under 35 U.S.C. 154(b) by 800 days.

(21) Appl. No.: 12/213,006

(22) Filed: Jun. 12, 2008

(65) Prior Publication Data

US 2009/0017040 A1    Jan. 15, 2009

Related U.S. Application Data

(60) Provisional application No. 60/943,541, filed on Jun. 12, 2007, provisional application No. 60/943,790, filed on Jun. 13, 2007.

(51) Int. Cl.
*A61K 39/395* (2006.01)
*C07K 16/18* (2006.01)
*C12N 5/20* (2006.01)
*A61K 38/18* (2006.01)

(52) U.S. Cl.
USPC ............... 424/141.1; 530/388.1; 435/326; 514/17.7; 514/17.8

(58) Field of Classification Search
None
See application file for complete search history.

(56) References Cited

U.S. PATENT DOCUMENTS

| | | | |
|---|---|---|---|
| 4,666,829 A | 5/1987 | Glenner et al. | |
| 4,895,841 A | 1/1990 | Sugimoto et al. | |
| 5,218,100 A | 6/1993 | Muller-Hill et al. | |
| 5,231,000 A | 7/1993 | Majocha et al. | |
| 5,231,170 A | 7/1993 | Averback | |
| 5,234,814 A | 8/1993 | Card et al. | |
| 5,262,332 A | 11/1993 | Selkoe | |
| 5,441,870 A | 8/1995 | Seubert et al. | |
| 5,538,845 A | 7/1996 | Knops | |
| 5,567,720 A | 10/1996 | Averback | |
| 5,589,154 A | 12/1996 | Anderson | |
| 5,593,846 A | 1/1997 | Schenk et al. | |
| 5,602,179 A | 2/1997 | Makovec et al. | |
| 5,605,811 A | 2/1997 | Seubert et al. | |
| 5,624,821 A | 4/1997 | Winter et al. | |
| 5,665,355 A | 9/1997 | Primi | |
| 5,679,531 A | 10/1997 | Konig | |
| 5,688,651 A | 11/1997 | Solomon | |
| 5,693,753 A | 12/1997 | Konig | |
| 5,705,401 A | 1/1998 | Masters et al. | |
| 5,721,130 A | 2/1998 | Seubert et al. | |
| 5,750,349 A | 5/1998 | Suzuki et al. | |
| 5,766,846 A | 6/1998 | Schlossmacher et al. | |
| 5,773,218 A | 6/1998 | Gallatin et al. | |
| 5,786,180 A | 7/1998 | Konig | |
| 5,955,285 A | 9/1999 | Averback | |
| 5,955,317 A | 9/1999 | Suzuki et al. | |
| 6,018,024 A | 1/2000 | Seubert et al. | |
| 6,080,588 A | 6/2000 | Glick et al. | |
| 6,114,133 A | 9/2000 | Seubert et al. | |
| 6,214,973 B1 | 4/2001 | Ohtomo et al. | |
| 6,218,506 B1 | 4/2001 | Krafft et al. | |
| 6,274,603 B1 * | 8/2001 | Poirier | 514/330 |
| 6,284,221 B1 | 9/2001 | Schenk et al. | |
| 6,287,793 B1 | 9/2001 | Schenk et al. | |
| 6,294,171 B2 | 9/2001 | McMichael | |
| 6,303,567 B1 | 10/2001 | Findeis et al. | |
| 6,309,892 B1 | 10/2001 | Averback | |
| 6,387,674 B1 | 5/2002 | Trasciatti | |
| 6,582,945 B1 | 6/2003 | Raso | |
| 6,610,493 B1 | 8/2003 | Citron et al. | |
| 6,664,442 B2 | 12/2003 | McConlogue et al. | |
| 6,737,056 B1 | 5/2004 | Presta | |
| 6,743,427 B1 | 6/2004 | Schenk | |
| 6,750,324 B1 | 6/2004 | Schenk | |
| 6,761,888 B1 | 7/2004 | Schenk | |
| 6,787,138 B1 | 9/2004 | Schenk | |

(Continued)

FOREIGN PATENT DOCUMENTS

| | | |
|---|---|---|
| CL | 2006-3485 | 12/2006 |
| CL | 2008-1741 | 6/2008 |

(Continued)

OTHER PUBLICATIONS

Casset et al (Biochemical and Biophysical Research Communications, 2003, vol. 307, pp. 198-205).*
U.S. Appl. No. 11/637,213, filed Dec. 11, 2006, Greferath et al.
U.S. Appl. No. 11/777,777, filed Jul. 13, 2007, Pfeifer et al.
U.S. Appl. No. 12/138,372, filed Jun. 12, 20068, Pfeifer et al.
U.S. Appl. No. 12/213,007, filed Jun. 12, 2008, Pfeifer et al.
U.S. Appl. No. 12/460,747, filed Jul. 23, 2009, Pfeifer et al.
Acha-Orbea et al., 1993, "Anti-T-cell receptor V beta antibodies in autoimmunity", Immunol Ser: 59:193-202.

(Continued)

*Primary Examiner* — Kimberly A Ballard
(74) *Attorney, Agent, or Firm* — Jones Day

(57) ABSTRACT

The present invention is related to methods and compositions for the therapeutic and diagnostic use in the treatment of diseases and disorders which are caused by or associated with amyloid or amyloid-like proteins including amyloidosis, a group of disorders and abnormalities associated with amyloid protein such as Alzheimer's disease. The present invention provides novel methods and compositions comprising highly specific and highly effective antibodies having the ability to specifically recognize and bind to specific epitopes from a range of β-amyloid proteins. The antibodies enabled by the teaching of the present invention are particularly useful for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD).

12 Claims, 9 Drawing Sheets

(56) References Cited

U.S. PATENT DOCUMENTS

| | | |
|---|---|---|
| 6,787,139 B1 | 9/2004 | Schenk |
| 6,787,140 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,815,175 B2 | 11/2004 | Weksler |
| 6,849,416 B2 | 2/2005 | Wiltfang et al. |
| 6,866,849 B2 | 3/2005 | Schenk |
| 6,866,850 B2 | 3/2005 | Schenk |
| 6,872,554 B2 | 3/2005 | Raso |
| 6,875,434 B1 | 4/2005 | Schenk |
| 6,905,686 B1 | 6/2005 | Schenk |
| 6,913,745 B1 | 7/2005 | Schenk |
| 6,936,698 B2 | 8/2005 | Taylor |
| 6,972,127 B2 | 12/2005 | Schenk |
| 6,998,124 B1 | 2/2006 | Erickson-Miller et al. |
| 7,014,855 B2 | 3/2006 | Schenk |
| 7,022,500 B1 | 4/2006 | Queen et al. |
| 7,060,270 B2 | 6/2006 | Nicolau et al. |
| 7,067,133 B2 | 6/2006 | Nicolau |
| 7,129,084 B2 | 10/2006 | Buelow et al. |
| 7,179,892 B2 | 2/2007 | Basi et al. |
| 7,189,819 B2 | 3/2007 | Basi et al. |
| 7,195,761 B2 | 3/2007 | Holtzman et al. |
| 7,256,273 B2 | 8/2007 | Basi et al. |
| 7,318,923 B2 | 1/2008 | Tsurushita et al. |
| 7,320,790 B2 | 1/2008 | Hinton et al. |
| 7,332,581 B2 | 2/2008 | Presta |
| 7,335,491 B2 | 2/2008 | Drapeau et al. |
| 7,339,035 B2 | 3/2008 | Yanagisawa et al. |
| 7,355,008 B2 | 4/2008 | Stavenhagen et al. |
| 7,371,365 B2 | 5/2008 | Poduslo et al. |
| 7,413,884 B2 | 8/2008 | Raso |
| 7,427,342 B2 | 9/2008 | Barber |
| 7,575,747 B2 | 8/2009 | Davies et al. |
| 7,625,560 B2 | 12/2009 | Basi et al. |
| 7,635,473 B2 | 12/2009 | Warne et al. |
| 7,732,568 B2 | 6/2010 | Mattner |
| 7,763,249 B2 | 7/2010 | Sugimura et al. |
| 7,763,250 B2 | 7/2010 | Rosenthal et al. |
| 7,771,722 B2 | 8/2010 | Holtzman et al. |
| 7,772,375 B2 * | 8/2010 | Greferath et al. ........ 530/388.85 |
| 7,780,963 B2 | 8/2010 | Acton et al. |
| 7,794,719 B2 | 9/2010 | Bardroff et al. |
| 7,807,157 B2 | 10/2010 | Yamaguchi et al. |
| 7,820,799 B2 | 10/2010 | Godavarti et al. |
| 7,871,615 B2 | 1/2011 | Basi et al. |
| 7,892,544 B2 | 2/2011 | Pfeifer et al. |
| 7,902,328 B2 | 3/2011 | Hillen et al. |
| 7,906,626 B2 | 3/2011 | Raso |
| 7,927,594 B2 | 4/2011 | Rosenthal et al. |
| 7,932,048 B2 | 4/2011 | Mendez |
| 8,034,339 B2 | 10/2011 | Schenk |
| 8,048,420 B2 | 11/2011 | Pfeifer et al. |
| 8,106,164 B2 | 1/2012 | Gellerfors et al. |
| 8,124,353 B2 | 2/2012 | Pfeifer et al. |
| 8,246,954 B2 | 8/2012 | Pfeifer et al. |
| 8,329,886 B2 | 12/2012 | Bardroff et al. |
| 2001/0029293 A1 | 10/2001 | Gallatin et al. |
| 2002/0009445 A1 | 1/2002 | Du et al. |
| 2002/0062009 A1 | 5/2002 | Taylor |
| 2002/0086847 A1 | 7/2002 | Chain |
| 2002/0094335 A1 | 7/2002 | Chalifour et al. |
| 2002/0182660 A1 | 12/2002 | Fong |
| 2002/0197258 A1 | 12/2002 | Ghanbari et al. |
| 2003/0068316 A1 | 4/2003 | Klein et al. |
| 2003/0108551 A1 | 6/2003 | Nicolau |
| 2003/0147882 A1 | 8/2003 | Solomon et al. |
| 2003/0190689 A1 | 10/2003 | Crosby et al. |
| 2003/0232758 A1 | 12/2003 | St. George-Hyslop et al. |
| 2004/0013647 A1 | 1/2004 | Solomon et al. |
| 2004/0043416 A1 | 3/2004 | Ji et al. |
| 2004/0043418 A1 | 3/2004 | Holtzman et al. |
| 2004/0058414 A1 | 3/2004 | Queen et al. |
| 2004/0087777 A1 | 5/2004 | Basi et al. |
| 2004/0142872 A1 | 7/2004 | Poduslo et al. |
| 2004/0146512 A1 | 7/2004 | Rosenthal et al. |
| 2004/0175394 A1 | 9/2004 | Schenk et al. |
| 2004/0181042 A1 | 9/2004 | Yanagisawa et al. |
| 2004/0191264 A1 | 9/2004 | Nielsen et al. |
| 2004/0192898 A1 | 9/2004 | Jia et al. |
| 2004/0213800 A1 | 10/2004 | Seubert et al. |
| 2004/0223912 A1 | 11/2004 | Montalto et al. |
| 2004/0241164 A1 | 12/2004 | Bales et al. |
| 2004/0242845 A1 | 12/2004 | Nicolau et al. |
| 2004/0248197 A1 | 12/2004 | Holtzman et al. |
| 2004/0265919 A1 | 12/2004 | Vanderstichele et al. |
| 2005/0013815 A1 | 1/2005 | Schenk |
| 2005/0019330 A1 | 1/2005 | Schenk |
| 2005/0031651 A1 | 2/2005 | Gervais et al. |
| 2005/0037000 A1 | 2/2005 | Stavenhagen et al. |
| 2005/0118651 A1 | 6/2005 | Basi et al. |
| 2005/0124016 A1 | 6/2005 | LaDu et al. |
| 2005/0129691 A1 | 6/2005 | Gerlai |
| 2005/0129695 A1 | 6/2005 | Mercken et al. |
| 2005/0130947 A1 | 6/2005 | Biggadike et al. |
| 2005/0147613 A1 | 7/2005 | Raso |
| 2005/0169925 A1 | 8/2005 | Bardroff et al. |
| 2005/0175626 A1 | 8/2005 | Delacourte et al. |
| 2006/0008458 A1 | 1/2006 | Solomon |
| 2006/0057646 A1 | 3/2006 | Wiltfang et al. |
| 2006/0057701 A1 | 3/2006 | Rosenthal et al. |
| 2006/0073149 A1 | 4/2006 | Bales et al. |
| 2006/0110388 A1 | 5/2006 | Davies et al. |
| 2006/0111301 A1 | 5/2006 | Mattner |
| 2006/0115477 A1 | 6/2006 | Unger et al. |
| 2006/0127954 A1 | 6/2006 | Mercken et al. |
| 2006/0160161 A1 | 7/2006 | Pavliakova et al. |
| 2006/0165682 A1 | 7/2006 | Basi et al. |
| 2006/0193850 A1 | 8/2006 | Warne et al. |
| 2006/0198851 A1 | 9/2006 | Basi et al. |
| 2006/0228349 A1 | 10/2006 | Acton et al. |
| 2006/0246075 A1 | 11/2006 | Mercken et al. |
| 2006/0280733 A1 | 12/2006 | Kayed et al. |
| 2006/0292152 A1 | 12/2006 | Rosenthal et al. |
| 2007/0010435 A1 | 1/2007 | Frangione et al. |
| 2007/0015218 A1 | 1/2007 | Cao et al. |
| 2007/0031416 A1 | 2/2007 | Shoji et al. |
| 2007/0072307 A1 | 3/2007 | Godavarti et al. |
| 2007/0098721 A1 | 5/2007 | Hillen et al. |
| 2007/0110750 A1 | 5/2007 | Glabe et al. |
| 2007/0128191 A1 | 6/2007 | Barrio |
| 2007/0166311 A1 | 7/2007 | Greferath et al. |
| 2007/0190046 A1 | 8/2007 | DeMattos et al. |
| 2007/0213512 A1 | 9/2007 | Krafft et al. |
| 2007/0218499 A1 | 9/2007 | Lambert et al. |
| 2008/0025988 A1 | 1/2008 | Yamaguchi et al. |
| 2008/0107601 A1 | 5/2008 | Lauwereys et al. |
| 2008/0121422 A1 | 5/2008 | Karasawa et al. |
| 2008/0131422 A1 | 6/2008 | Sugimura et al. |
| 2008/0199879 A1 | 8/2008 | Takayama et al. |
| 2008/0292639 A1 | 11/2008 | Shen et al. |
| 2009/0017040 A1 | 1/2009 | Pfeifer et al. |
| 2009/0017041 A1 | 1/2009 | Pfeifer et al. |
| 2009/0023159 A1 | 1/2009 | Mendez |
| 2009/0035295 A1 | 2/2009 | Hillen et al. |
| 2009/0035307 A1 | 2/2009 | Barghorn et al. |
| 2009/0074775 A1 | 3/2009 | Holtzman et al. |
| 2009/0093002 A1 | 4/2009 | Pfeifer et al. |
| 2009/0155246 A1 | 6/2009 | Gellerfors et al. |
| 2009/0155249 A1 | 6/2009 | Pfeifer et al. |
| 2009/0155256 A1 | 6/2009 | Black et al. |
| 2009/0156471 A1 | 6/2009 | Gazit et al. |
| 2009/0162362 A1 | 6/2009 | Sarasa |
| 2009/0162878 A1 | 6/2009 | Kim et al. |
| 2009/0175847 A1 | 7/2009 | Barghorn et al. |
| 2009/0191190 A1 | 7/2009 | Barghorn et al. |
| 2009/0214515 A1 | 8/2009 | Holzman et al. |
| 2009/0232801 A1 | 9/2009 | Hillen et al. |
| 2009/0238831 A1 | 9/2009 | Hillen et al. |
| 2010/0080800 A1 | 4/2010 | Pfeifer et al. |
| 2010/0150906 A1 | 6/2010 | Pfeifer |
| 2010/0291097 A1 | 11/2010 | Pfeifer et al. |
| 2010/0297012 A1 | 11/2010 | Pfeifer et al. |

(56) References Cited

U.S. PATENT DOCUMENTS

| | | |
|---|---|---|
| 2010/0297013 A1 | 11/2010 | Pfeifer et al. |
| 2010/0297132 A1 | 11/2010 | Greferath et al. |
| 2011/0070613 A1 | 3/2011 | Greferath et al. |
| 2011/0212109 A1 | 9/2011 | Barghorn et al. |
| 2012/0064065 A1 | 3/2012 | Pfeifer et al. |
| 2012/0171216 A1 | 7/2012 | Pfeifer et al. |
| 2012/0244165 A1 | 9/2012 | Greferath et al. |
| 2012/0288896 A1 | 11/2012 | Greferath et al. |
| 2012/0329149 A1 | 12/2012 | Pfeifer et al. |
| 2013/0164278 A1 | 6/2013 | Pfeifer et al. |

FOREIGN PATENT DOCUMENTS

| | | |
|---|---|---|
| CL | 2008-1742 | 6/2008 |
| CL | 2007-2070 | 7/2011 |
| CN | 1396183 | 2/2003 |
| DE | 3805744 | 2/1988 |
| EP | 0296560 B1 | 6/1988 |
| EP | 0613007 | 8/1994 |
| EP | 0623675 | 11/1994 |
| EP | 0304013 | 6/1996 |
| EP | 0783104 | 7/1997 |
| EP | 1130032 | 9/2001 |
| EP | 1420032 | 5/2004 |
| EP | 1741783 | 1/2007 |
| EP | 1861422 | 12/2007 |
| EP | 1954718 | 8/2008 |
| EP | 1963363 | 9/2008 |
| EP | 1976877 | 10/2008 |
| JP | 2007238096 | 9/1995 |
| JP | 2003-509020 | 3/2003 |
| JP | 2003-523764 | 8/2003 |
| JP | 2004-500354 | 1/2004 |
| JP | 2005185281 | 7/2005 |
| JP | 2005-527199 | 9/2005 |
| JP | 2007077103 | 3/2007 |
| JP | 2009-519711 | 5/2009 |
| WO | WO 89/07657 | 8/1989 |
| WO | 90/05746 * | 5/1990 |
| WO | WO 90/05746 | 5/1990 |
| WO | WO 91/18983 A1 | 12/1991 |
| WO | WO 92/11018 | 7/1992 |
| WO | WO 95/11994 | 5/1995 |
| WO | WO 96/01359 | 1/1996 |
| WO | WO 96/28187 | 9/1996 |
| WO | WO 96/29605 | 9/1996 |
| WO | WO 96/03631 | 11/1996 |
| WO | WO 96/36361 A1 | 11/1996 |
| WO | WO 96/40731 | 12/1996 |
| WO | WO 97/10505 | 3/1997 |
| WO | WO 97/18476 | 5/1997 |
| WO | WO 97/21728 | 6/1997 |
| WO | WO 99/05175 | 2/1999 |
| WO | WO 99/27944 | 6/1999 |
| WO | 99/40837 * | 8/1999 |
| WO | WO 99/40837 | 8/1999 |
| WO | WO 99/40909 | 8/1999 |
| WO | WO 99/59571 | 11/1999 |
| WO | WO 00/42072 A2 | 7/2000 |
| WO | WO 00/56771 | 9/2000 |
| WO | WO 00/72880 | 12/2000 |
| WO | WO 01/16364 | 3/2001 |
| WO | WO 01/18169 | 3/2001 |
| WO | WO 01/39796 A2 | 6/2001 |
| WO | WO 01/62801 | 8/2001 |
| WO | WO 01/85093 | 11/2001 |
| WO | WO 02/46237 | 6/2002 |
| WO | WO 02/096937 | 12/2002 |
| WO | WO 03/014162 | 2/2003 |
| WO | WO 03/016466 | 2/2003 |
| WO | WO 03/031475 A2 | 4/2003 |
| WO | WO 03/039467 A2 | 5/2003 |
| WO | WO 03/070760 | 8/2003 |
| WO | WO 03/076006 | 9/2003 |
| WO | WO 03/077858 | 9/2003 |
| WO | WO 03/089460 A1 | 10/2003 |
| WO | WO 03/090772 | 11/2003 |
| WO | WO 2004/024090 | 3/2004 |
| WO | WO 2004/029093 | 4/2004 |
| WO | WO 2004/031400 A2 | 4/2004 |
| WO | WO 2004/050707 | 6/2004 |
| WO | WO 2004/058258 | 7/2004 |
| WO | WO 2004/065569 | 8/2004 |
| WO | WO 2004/067561 | 8/2004 |
| WO | WO 2004/071408 | 8/2004 |
| WO | WO 2004/108895 | 12/2004 |
| WO | WO 2005/005638 | 1/2005 |
| WO | WO 2005/018424 | 3/2005 |
| WO | WO 2005/025516 | 3/2005 |
| WO | WO 2005/053604 | 6/2005 |
| WO | WO 2005/058941 A2 | 6/2005 |
| WO | WO 2005/081872 | 9/2005 |
| WO | WO 2005/105998 | 11/2005 |
| WO | WO 2005/120571 | 12/2005 |
| WO | WO 2006/014478 A1 | 2/2006 |
| WO | WO 2006/016644 | 2/2006 |
| WO | WO 2006/029879 A2 | 3/2006 |
| WO | WO 2006/036291 | 4/2006 |
| WO | WO 2006/037604 | 4/2006 |
| WO | WO 2006/039327 | 4/2006 |
| WO | WO 2006/055178 | 5/2006 |
| WO | WO 2006/066049 | 6/2006 |
| WO | WO 2006/066089 A1 | 6/2006 |
| WO | WO 2006/066171 | 6/2006 |
| WO | WO 2006/081171 A1 | 8/2006 |
| WO | WO 2006/083533 | 8/2006 |
| WO | WO 2006/083689 A2 | 8/2006 |
| WO | WO 2006/094724 | 9/2006 |
| WO | WO 2006/103116 | 10/2006 |
| WO | WO 2006/118959 A2 | 11/2006 |
| WO | WO 2006/121656 | 11/2006 |
| WO | WO 2006/138737 A2 | 12/2006 |
| WO | WO 2007/011639 | 1/2007 |
| WO | WO 2007/017686 | 2/2007 |
| WO | WO 2007/022416 | 2/2007 |
| WO | WO 2007/042261 | 4/2007 |
| WO | WO 2007/050359 | 5/2007 |
| WO | WO 2007/062088 | 5/2007 |
| WO | WO 2007/062852 | 6/2007 |
| WO | WO 2007/064917 | 6/2007 |
| WO | WO 2007/064919 | 6/2007 |
| WO | WO 2007/064972 | 6/2007 |
| WO | WO 2007/068412 | 6/2007 |
| WO | WO 2007/068429 | 6/2007 |
| WO | WO 2007/070432 A2 | 6/2007 |
| WO | WO 2007/106617 | 9/2007 |
| WO | WO 2007/108756 | 9/2007 |
| WO | WO 2007/113172 | 10/2007 |
| WO | WO 2007/123345 | 11/2007 |
| WO | WO 2008/002893 | 1/2008 |
| WO | WO 2008/011348 | 1/2008 |
| WO | WO 2008/012101 | 1/2008 |
| WO | WO 2008/030251 | 3/2008 |
| WO | WO 2008/045962 | 4/2008 |
| WO | WO 2008/060364 | 5/2008 |
| WO | WO 2008/061795 | 5/2008 |
| WO | WO 2008/067464 | 6/2008 |
| WO | WO 2008/070229 | 6/2008 |
| WO | WO 2008/071394 | 6/2008 |
| WO | WO 2008/104385 | 9/2008 |
| WO | WO 2008/104386 | 9/2008 |
| WO | WO 2008/110885 | 9/2008 |
| WO | WO 2008/143708 | 11/2008 |
| WO | WO 2008/150946 | 12/2008 |
| WO | WO 2008/150949 | 12/2008 |
| WO | WO 2008/156621 | 12/2008 |
| WO | WO 2008/156622 | 12/2008 |
| WO | WO 2009/048537 | 4/2009 |
| WO | WO 2009/048538 | 4/2009 |
| WO | WO 2009/048539 | 4/2009 |

(56) References Cited

FOREIGN PATENT DOCUMENTS

OTHER PUBLICATIONS

Anderson et al., 2004, "Characterization of beta amyloid assemblies in drusen: the deposits associated with aging and age-related macular degeneration", Experimental Eye Research: 78:243-256.
Bard et al., 2000, "Peripherally administered antibodies against amyloid bipeptide enter the central nervous system and reduce pathology in a mouse model of Alzheimer disease", Nature Med.; 6:916-919.
Bard et al., 2003, "Epitope and isotype specificities of antibodies to beta-amyloid peptide for protection against Alzheimer's disease-like neuropathology", Proc Natl Acad Sci USA; 100(4): 2023-2028.
Barghorn et al., 2005, "Globular amyloid beta-peptide 1-42 oligomer—a homogeneous and stable neuropatholgical protein in Alzheimer's disease", J Neurochem; 95(31):834-847.
Barrow et al.,1992, "Solution conformations and aggregational properties of synthetic amyloid beta-peptides of Alzheimer's disease. Analysis of circular dichroism spectra", J. Mol. Biol.; 225:1075-1093.
Blond et al., 1987, "Partly native epitopes are already present on early intermediates in the folding of trytophan synthase", Proc Natl Acad Sci USA; 84:1147-1151.
Burdick et al., 1992, "Assembly and aggregation properties of synthetic Alzheimer's A4/beta amyloid peptide analogs", J Biol Chem; 267:546-554.
Campbell et al., 1984, "General properties and applications of monoclonal antibodies", Elsevier Science Publishers B.V., pp. 1-32.
Celli et al., 1998, "Origin and pathogenesis of antiphospholipid antibodies", Braz J Med Biol Res; 31(6):723-732.
Clackson et al., 1991, "Making antibody fragments using phage display libraries"Nature; 352(15):624-328.
Database EMBL [Online], 1988, "Mouse innunoglobulin rearranged kappa-chain V-region V105 gene from C.AL20-TEPC-105 myeloma, exons 1 and 2", retrieved from EBI accession No. EMBL:M12183 Database accession No. M12183.
Database EMBL [Online], 1999, "Mus musculus F5.20G3 low-affinity anti-phosphorylcholine IgG antibody mRNA, partial cds", retrieved from EBI accession No. EMBL:AF044238 Database accession No. AF044238.
Database Geneseq [Online], 1988. "L chain subunit of FAS specific antibody coding sequence", retrieved from EBI accession No. GSN:AAT88870 Database accession No. AAT88870.
Database Geneseq [Online], 1999, "Anti-human FAS monoclonal antibody CHII light chain cDNA", retrieved from EBI accession No. GSN:AAV66736 Database accession No. AAV66736.
Database Geneseq [Online], 2003, "Mouse DNA encoding antibody 3D8 heavy chain variable region", retrieved from FBI accession No. GSN:ABXI6569 Database accession No. ABX16569.
Database Geneseq [Online], 2005, "Humanized monoclonal antibody Hu4785-2 heavy chain", retrieved from EBI accession No. GSP:ADX39139 Database accession No. ADX39139.
Database Geneseq [Online], 2005, "Humanized monoclonal antibody Hu4785-2 VH region", retrieved from FBI accession No. Gsp:ADX39I43 Database accession No. ADX39I43.
Database Geneseq [Online], 2005, "Humanized monoclonal antibody Hu4785-2 partial protein", retrieved from EBI accession No. GSP:ADX39104 Database accession No. ADX39104.
Database Geneseq [Online], 2005, "Mouse monoclonal antibody 4785 heavy chain SEQ ID 38", retrieved from EBI accession No. GSP:ADX39137 Database accession No. ADX39137.
Database Geneseq [Online], 2005, "Mouse monoclonal antibody 4785 heavy chain SEQ ID 1" retrieved from EBI accession No. GSP:ADX39100 Database accession No. ADX39100.
Database NCBI Protein [Online] dated Apr. 11, 1996, accession No. AAA96779.
Database NCBI Protein [Online] dated Aug. 30, 1993, accession No. AAA38584.
Database NCBI Protein [Online] dated Mar. 23, 2002, accession No. AAL92941.
Database NCBI Protein [Online] dated Mar. 23, 2002, accession No. AAL92933.
David et al., 1991,"A significant reduction in the incidence of collagen induced arthritis in mice treated with anti-TCRV-beta antibodies". J Cell Biochem; p. I79.
Davies et al., 1995, "Antibody VH domains as small recognition units", Biotechnology;13:475-479.
De Giorgi et al., 1993, "Induction of foetal lethality in AKR offspring after repeated inoculations into AKR females of anti-TCR/V beta 6 monoclonal antibody", Res Immunol: 144(4):245-255.
De Giorgi et al., 1993, "Murine hybridomas secreting monoclonal antibodies reacting with Mlsa antigens", Exp Clin Immunogenet; 10(4):219-223.
Demattos et al., 2001, "Peripheral anti-Aβ antibody alters CNS and plasma Aβ clearance and decreases brain Aβ burden in a mouse model of Alzheimer's disease", Proc Natl Acad Sci USA; 98:8850-8855.
Dewachter et al., 2000, "Aging increased amyloid peptide and caused amyloid plaques in brain of old APP/V717I transgenic mice by a different mechanism than mutant presenilin 1", J Neurosci; 20:6452-6458.
Dewachter et al., 2002, "Neuronal deficiency of presenilin 1 inhibits amyloid plaque formation and corrects hippocampal long-term potentiation but not a cognitive defect of amyloid precursor protein [V7171] transgenic mice", J Neurosci; 22:3445-3453.
Ding et al., 2007, "Targeting age-related macular degeneration with Alzheimer's disease based immunotherapies: anti-amyloid-beta antibody attenuates pathologies in an age-related macular degeneration mouse model", Vision Research, Pergamon Press, Oxford, GB; 48(3):339-345.
Dorronsoro et al., 2003, "Peripheral and dual binding site inhibitors of acetylcholinesterase as neurodegenerative disease-modifying agents", Expert Opin Ther Pat; 13(11): 1725-1732.
Dumoulin et al., 2002, "Single-domain antibody fragments with high conformational stability", Protein Sci; 11:500-515.
European Office Action of application No. 06829456.0-2402, dated Dec. 23, 2008.
European Office Action of Application No. 08768370.2-1222, dated May 3, 2010.
European Office Action of application No. 08768371.0-2406, dated Jun. 28, 2010.
Frenkel et al., 2000, "Modulation of Alzheimer's beta-amyloid neurotoxicity by site-directed single-chain antibody", J Neuroimmunol; 106(1-2):23-31.
Fujimuro et al., 1994, "Production and characterization of monoclonal antibodies specific to multi-ubiquitin chains of polyubiquitinated proteins", FEBS; 349:173-180.
Fujimuro et al., 2005, "Production of antipolyubiquitin monoclonal antibodies and their use for characterization and isolation of polyubiquitinated proteins", Meth Enzymol; 399:75-86.
Fukuchi et al., 2006, "Amelioration of amyloid load by anti-Abeta single-chain antibody in Alzheimer mouse model", Biochem Biophys Res Commun; 344(1):79-86.
Glenner et al., 1984, "Alzheimer's disease: initial report of the purification and characterization of a novel cerebrovascular amyloid protein", Biochem Biophys Res Comm; 129:885-890.
Guo et al., 2007, "Targeting amyloid-beta in glaucoma treatment", Proc Nalt Acad Sci USA; 104(33):13444-13449.
Heneka et al., 2005, "Focal glial activation coincides with increased with increased BACE1 activation and precedes amyloid plaque deposition in APP[V171] transgenic mice", J Neuroinflammation; 2:22.
Hicke, 2001, "Protein regulation by monoubiquitin", Nat Rev; 2:196-201.
International Preliminary Report on Patentability of International application No. PCT/US2007/073504, dated Jan. 22, 2009.
International Preliminary Report on Patentability of International application No. PCT/EP2006/011862, dated Jun. 26, 2008.
International Preliminary Report on Patentability of International application No. PCT/US2008/007318, dated Dec. 17, 2009.
International Preliminary Report on Patentability of International application No. PCT/US2007/021134, dated Apr. 7, 2009.
International Preliminary Report on Patentability of International application No. PCT/US2008/007317. dated Dec. 17, 2009.

(56) References Cited

OTHER PUBLICATIONS

International Preliminary Report on Patentability of International application No. PCT/US2008/011491, dated Apr. 15, 2010.
International Preliminary Report on Patentability of International application No. PCT/US2008/011492, dated Apr. 15, 2010.
International Preliminary Report on Patentability of International application No. PCT/US2008/011493, dated Apr. 15, 2010.
International Search Report for International Application No. PCT/EP2006/011862, dated Jun. 12, 2007.
International Search Report for International Application No. PCT/US2007/073504. dated May 14, 2008.
International Search Report of International application No. PCT/US2000/014810, dated Dec. 15, 2000.
International Search Report of International application No. PCT/US2007/021134, dated Dec. 19, 2008.
International Search Report of International application No. PCT/US2008/007317, dated Oct. 28, 2008.
International Search Report of International application No. PCT/US2008/007318, dated Nov. 21, 2008.
International Search Report of International application No. PCT/US2008/011491, dated Jul. 20. 2009.
International Search Report of International application No. PCT/US2008/011492, dated Sep. 7, 2009.
International Search Report of International application No. PCT/US2008/011493, dated Oct. 12, 2009.
Johnson-Wood et al.,1997, "Amyloid precursor protein processing and A beta42 deposition in a transgenic mouse model of Alzheimer disease", Proc. Natl. Acad. Sci. USA; 94(4):1550-1555.
Jung et al., 1996, "Alzheimer's beta-amyloid precursor protein is expressed on the surface of immediately ex vivo brain cells: a flow cytometric study", J. Neurosci. Res.; 46(3):336-348.
Khaw et al., 1982, "Technetium-99m labeling of antibodies to cardiac myosin Fab and to human fibrinogen", J Nucl Med; 23:1011-1019.
Kim et al., 2004, "Development of conformation-specific antibodies for neutralization of beta-amyloid oligomers", Neurobiol Aging; 25(1):S145, P1-175 Abstract.
Kirschner et al., 1986, "X-ray diffraction from intraneuronal paired helical filaments and extraneuronal amyloid fibers in Alzheimer disease indices cross-beta conformation". Proc Natl Acad Sci USA: 83:503-507.
Kisilevsky et al., 1995. "Arresting amyloidosis in vivo using small-molecule anionic sulphonates or sulphates: Implications for Alzheimer's disease". Nat Med; 1(2):143-148.
Kisilevsky, 1996. "Anti-amyloid drugs potential in the treatment of diseases associated with aging", Drugs Aging; 8(2):75-83.
Klein et al., 2002, "Abeta toxicity in Alzheimer's disease: globular oligomers (ADDLs) as new vaccine and drug targets", Neurochem Int; 41(5):345-352.
Klimka et al., 2000, "Human anti-CD30 recombinant antibodies by guided phage antibody selection using cell panning", Brit J Cancer; 83(2):252-260.
Lambert et al., 2007. "Monoclonal antibodies that target pathological assemblies of Abeta", J Neurochem; 100(1): 23-35.
Langdon et al., 2000, "Germline sequences of $V_H$7183 gene family members in C57BL/6 mice demonstrate natural selection of particular sequences during recent evolution", Immunogen; 51:241-245.
Lee et al., 2002, "Molecular cloning of agonistic and antagonistic monoclonal antibodies against human 4-1BB", Eur J Immunogenet; 29(5):449-452.
Levine et al., 2002, "4,4'-dianilino-1,1'-binaphthyl-5-disulfonate (bis-ANS) reports on non-β-sheet conformers of Alzheimer's peptide β (1-40)", Arch Biochem Biophys; 404:106-115.
Liu Ruitian et al., 2004, "Single chain variable fragments against beta-amyloid (Abeta) can inhibit Abeta aggregation and prevent Abeta-induced neurotoxicity", Biochem; 43(22):6959-6967.
Lund et al., 1995, "Oligosaccharide-protein interactions in IgG can modulate recognition by Fc-gamma receptors". FASEB J; 9(1):115-119.
Marks et al., 1992, "By-passing immunization: Building high affinity human antibodies by chain shuffling", Biotechnology; 10:779-783.
McGreer et al., 1994, "Pathological proteins in senile plaques". Tohoku J Exp Med; 174:269-277.
McKinnon et al., 2002. "Caspase activation and amyloid precursor protein cleavage in rat ocular hypertension", Invest Ophthamol & Vis Sci: 43(4):1077-1087.
McLaurin et al., 2002, "Therapeutically effective antibodies against amyloid-beta peptide target amyloid-beta residues 4-10 and inhibit cytotoxicity and fibrillogenesis", Nat Med; 8(11):1263-1269.
Moechars et al., 1999, "Early phenotypic changes in transgenic mice that overexpress different mutants of amyloid precursor protein in brain", J Biol Chem; 274:6483-6492.
Moretto et al., 2007, "Conformation-sensitive antibodies against Alzheimer amyloid-beta by immunization with a thioredoxin-constrained B-cell epitope peptide", J Biol Chem: 282(15):11436-11445.
Nelson et al.. 2006, "Recent atomic models of amyloid fibril structure", Curr Opin Struct Biol: 16:260-265.
Nemes et al., 2004, "Cross-linking of ubiquitin, HSP27, parkin, and α-synuclein by γ-glutamyl-ε-lysine bonds in Alzheimer's neurofibrillary tangles", FASEB J; 18:1135-37.
Nicolau et al., 2002,"A liposome-based therapeutic vaccine against beta-amyloid plaques on the pancreas of transgenic norba mice", Proc Natl Acad Sci USA; 99(4): 2332-2337.
Notice of Allowance and Fees Due of U.S. Appl. No. 11/637,213, dated Dec. 14, 2009.
Office Action of U.S. Appl. No. 11/637,213, dated Aug. 31, 2009.
Office Action of U.S. Appl. No. 11/637,213, dated Feb. 17, 2009.
Office Action of U.S. Appl. No. 11/637,213, dated Sep. 11, 2009.
Office Action of U.S. Appl. No. 12/138,372, dated Sep. 1. 2009.
Padlan et al., 1989, "Structure of an antibody-antigen complex: crystal structure of the HyHEL-10 Fab-lysozyme complex", Proc Natl Acad Sci USA; 86(15):5938-42.
Paul eds., 1993, "Fv structure and diversity in three dimensions", Fundamental Immunology; 292-295.
Pereira et al., 1998, "Cardiolipin binding a light chain from lupus-prone mice", Biochemistry: 37(5):1430-1437.
Petkova et al., 2002. "A structural model for Alzheimer's β-amyloid fibrils based on experimental constraints from solid state NMR", Proc Natl Acad Sci USA; 99:16742-16747.
Petkova et al., 2004, "Solid state NMR reveals a pH-dependent antiparallel β-sheet registry in fibrils formed by a β-amyloid peptide", J Mol Biol; 335:247-260.
Portolano et al., 1993. "Lack of promiscuity in autoantigen-specific H and L chain combination as revealed by human H and L chain roulette", J Immunol; 150(3):880-887.
Racke et al., 2005, "Exacerbation of cerebral amyloid angiopathy-associated microhemorrhage in amyloid precursor protein transgenic mice by immunotherapy is dependent on antibody recognition of deposited forms of amyloid beta", J. Neurosci.; 25(3):629-636.
Rader et al., 1998 "A phage display approach for rapid antibody humanization:designed combinatorial V gene libraries", Proc Natl Acad Sci USA; 95:8910-8915.
Rudikoff et al., 1982, "Single amino acid substitution altering antigen-binding specificity", Proc Natl Acad Sci USA; 79(6):1979-1983.
Russian Office Action, dated May 6, 2009.
Rzepecki et al., 2004, "Prevention of Alzheimer's disease-associated Aβ aggregation by rationally designed non-peptide β-sheet ligands", J Biol Chem; 279(46):47497-47505.
Saudi Arabian Office Action of application No. GCC/P/2006/7389. dated Mar. 5, 2010.
Schable et al., 1999, "Characteristics of the immunoglobulin V kappa genes, pseudogenes relics and orphons in the mouse genome". Eur J Immunol; 29:2082-2086.
Schenk et al., 1999, "Immunization with anyloid-beta attenuates Alzheimer-disease-like pathology in the PDAPP mouse". Nature; 400:173-177.
Seubert et al., 1992, "Isolation and quantification of soluble Alzheimer's beta-peptide from biological fluids", Nature 359(6393):325-327.

(56) References Cited

OTHER PUBLICATIONS

Smith et al., 1995, "Determination of helix-helix interactions in membranes by rotational resonance NMR", Proc Natl Acad Sci USA; 92:488-491.
Solomon et al., 1996, "Monoclonal antibodies inhibit in vitro fibrillar aggregation of the Alzheimer beta-amyloid peptide", Proc Natl Acad Sci USA:93:452-455.
Solomon et al., 1997 "Disaggregation of Alzheimer β-amyloid by site-directed mAb", Proc Natl Acad Sci USA; 94:4109-4112.
Solomon, 2007, "Beta-amyloid based immunotherapy as a treatment of Alzheimer's disease", Drugs of Today: 43(5):333-342.
Soto et al., 1995, "The alpha-helical to beta-strand transition in the amino-terminal fragment of the amyloid beta-peptide modulates amyloid formation", J. Biol. Chem.; 270(7):3063-3067.
Tenno et al., 1994, "Structural basis for distinct roles of Lys63- and Lys48-linked polyubiquitin chains". Genes to Cells: 9:865-875.
Van Den Beucken et al., 2001, "Building novel binding ligands to B7.1 and B7.2 based on human antibody single variable light chain domains", J Mol Biol: 310:591-601.
Van Der Auwera et al., 2005, "A ketogenic diet reduces amyloid beta 40 and 42 in a mouse model of Alzheimer's disease", Nutr Metab (Lond): 2:28.
Van Gool et al., 1994, "Concentrations of amyloid-beta protein in cerebrospinal fluid increase with age in patients free from neurodegenerative disease", Neurosci Let: 172(1-2):122-124.
Ward et al.. 1989, "Binding activities of a repertoire of single immunoglobulin variable domains secreted from *Escherichia coli*". Letters to Nature; 341(12):544-546.
Weaver-Feldhaus et al., 2004, "Yeast mating for combinatorial Fab library generation and surface display", FEBS Letters; 564(2):24-34.
Written Opinion of International Application No. PCT/EP2006/011862, dated Jun. 12, 2007.
Written Opinion of International Application No. PCT/US2007/021134, dated Dec. 19, 2008.
Written Opinion of International Application No. PCT/US2007/073504, dated May 14, 2008.
Written Opinion of International application No. PCT/US2008/007318, dated Nov. 21, 2008.
Written Opinion of International application No. PCT/US2008/007317, dated Oct. 28, 2008.
Written Opinion of International Application No. PCT/US2008/011493, dated Oct. 12, 2009.
Written Opinion of International Application No. PCT/US2008/011492, dated Sep. 7, 2009.
Written Opinion of International Application No. PCT/US2008/011491, dated Jul. 20, 2009.
European Office Action of European application No. 06829456.0-2402, dated Jul. 30, 2010.
Hanan et al., 1996. "Inhibitory effect of monoclonal antibodies on Alzheime'sβ-amyloid peptide aggregation", Amyloid: Int J Exp Clin Invest; 3:130-133.
Notice of Allowance of U.S. Appl. No. 11/777,777, dated Jul. 30, 2010.
Office Action of U.S. Appl. No. 12/213,007, dated Jun. 7, 2010.
Russian Office Action of U.S. Appl. No. 2008128139, dated Jul. 13, 2010.
Chilean Office Action of application No. 2007-2070 with English Technical Report, dated Mar. 14, 2011.
Chinese Office Action of application No. 200680046466.9, dated Mar. 24, 2011.
Davies et al., 1996, "Affinity improvement of single antibody VH domains: residues in all three hypervariable regions affect antigen binding", Immunotechnology; 2(3):169-179.
European Office Action of EP application No. 08836966.5-2406, dated May 18, 2010.
European Office Action of EP application No. 08837467.3-406, dated Oct. 21, 2010.
Ewert et al., 2003 "Biophysical properties of human antibody variable domains", J Mol Biol; 325;531-553.

Holt et al., 2003, "Domain antibodies: proteins for therapy", Trends in Biotechnology; 21(11);484-490.
Indonesian Office Action of application No. W-00200801821, dated Feb. 25, 2011.
Maynard et al., 2000, "Antibody engineering", Annu Rev Biomed Eng; 2:339-376.
Mexican Office Action (translation) of application No. MX/a/2009/000476 dated Mar. 30, 2011.
Mexican Office Action of application No. MX/a/2008/007477, dated Mar. 17, 2011.
Mitchell et al. 2007, "Prevention of intracerebral haemorrhage", Current Drug Targets; 8:832-838.
New Zealand Examination Report of application No. 574188, dated Jun. 23, 2010.
New Zealand Examination Report of application No. 581834, dated Oct. 29, 2010.
New Zealand Examination Report of application No. 581835, dated Nov. 2, 2010.
New Zealand Examination Report of application No. 585110, dated Jan. 19, 2011.
Office Action of U.S. Appl. No. 12/311,505 dated Apr. 4, 2011.
Office Action of U.S. Appl. No. 12/460,747, dated Jun. 8, 2011.
Office Action of U.S. Appl. No. 11/637,213, dated Apr. 27, 2009.
Office Action of U.S. Appl. No. 11/777,777, dated Aug. 10, 2009.
Office Action of U.S. Appl. No. 11/777,777, dated May 5, 2010.
Pini et al., 1998, "Design and use of a phage display library. Human antibodies with subnanornolar affinity against a marker of angiogenesis eluted from a two-dimensional gel", J Biol Chem; 273(34)11769-21776.
Russian Office Action of application No. 2008128139, dated Oct. 1, 2008.
Russian Office Action of application No. 2009104769, dated Mar. 17, 2011.
Singapore Examination Report of application No. 200900163-7, dated Sep. 30, 2010.
Singapore Written Opinion of application No. 200900163-7, dated Nov. 30, 2009.
Hungarian Search Report of Singaporean application No. 200908189-4, dated Dec. 17, 2010.
Vickers, 2002, "A vaccine against Alzheimer's disease", Drugs Aging; 19(7):487-494.
Vietnamese Office Action of application No. 1-2008-01736, dated Dec. 1, 2008.
Vietnamese Office Action of application No. 1-2008-01736, dated Dec. 1, 2009.
Vietnamese Office Action of application No. 1-2008-01736, dated Jul. 22, 2009.
Written Opinion of Singapore application No. 201002372-9, dated Oct. 22, 2010.
Casset et al., 2003, "A peptide mimetic of an anti-CD4 monoclonal antibody by rational design", Biochemical and Biophysical Research Communications; 307(1):198-205.
Chen et al., 1999, "Selection and analysis of an optimized anti-VEGF antibody: crystal structure of an affinity-matured Fab in complex with antigen", J Mol Biol; 293:865-881.
European Office Action of European application No. 08768371.0-2406, dated Feb. 8, 2011.
European Office Action of European application No. 08838455.7-2406, dated Oct. 21, 2010.
Holm et al., 2007, "Functional mapping and single chain construction of the anti-cytokeratin 8 monoclonal antibody TS1", Mol Immunol; 44:1075-1084.
MacCallum et al., 1996, "Antibody-antigen interactions: contact analysis and binding site topography", J Mol Biol; 262:732-745.
Mexican Office Action (translation) of application No. MX/a/2009/013503, dated Dec. 28, 2010.
Office Action of U.S. Appl. No. 12/138,372, dated Feb. 2, 2011.
Office Action of U.S. Appl. No. 12/213,007, dated Nov. 19, 2010.
Rebe et al., 2005, "Deglycosylation of anti-βamyloid antibodies inhibits microglia activation in BV-2 cellular model", American Journal of Alzheimer's Disease and Other Dimentias; 20(5):303-313.
Russian Office Action of application No. 2008128139, dated Nov. 8, 2010.

(56) References Cited

OTHER PUBLICATIONS

Russian Office Action of application No. 2010200342/20(000411), dated Jul. 12, 2010.
Sergeant, 2003, "Truncated beta-amyloid peptide species in preclinical Alzheimer's disease as new targets for the vaccination approach", J Neurochem; 85(6):1581-91.
Singapore Office Action of patent application No. 200804129-5, dated Aug. 23, 2010, with Examination Report, dated Jun. 9, 2010.
Vajdos et al., 2002, "Comprehensive functional maps of the antigen-binding site of an anti-ErbB2 antibody obtained with shotgun scanning mutagenesis", J Mol Biol; 320(2):415-428.
"Comparison of 8F5 and FP12H3-C2/ACI-01-Ab-7-C2 antibodies", AC Immune, Aug. 2009, pp. 1-3.
"Staining of human Brain Sections with AC Immune's humanized ACI-01-Ab7 Antibody", Study ACI-Bonn-01, AC Immune, Sep. 26, 2006, pp. 1-4.
"Studies of Influence of Passive Caccination with ACI-01-Ab7 on Memory Capacity in single transgenic hAPP Mice" AC Immune, 2006, pp. 1-3.
"Studies to map the Epitope of AC Immune's monoclonal Antibody ACI-01-Ab7", AC Immune, 2006, pp. 1-5.
"Study to analyze the Binding of AC Immune's monoclonal Antibody ACI-01-Ab7 to Amyloid Species in Western Blot and Dot Blot", AC Immune, 2006, pp. 1-4.
"Study to analyze the Binding of AC Immune's murine monoclonal Antibody ACI-01-Ab7 to Amyloid Species in ELISA", AC Immune, 2006, pp. 1-2.
Abuchowski et al., 1977, "Effect of covalent attachment of polyethylene glycol on immunogenicity and circulating life of bovine liver catalase", J Biol Chem; 252(11):3582-3586.
Adolfsson et al., 2012, "An effector-reduced anti-β-amyloid (Aβ) antibody with unique aβ binding properties promotes neuroprotection and glial engulfment of Aβ", J Neurosci; 32(28):9677-9689.
Australian Examination Report dated Apr. 20, 2012 of Australian application No. 2007275467.
Australian Examination Report dated Aug. 23, 2011 of Australian application No. 2006326284.
Australian Examination Report dated Feb. 15, 2013 of Australian application No. 2008311367.
Australian Examination Report dated May 29, 2013 of Australian application No. 2008311366.
Australian Examination Report dated Nov. 14, 2012 of Australian application No. 2008267037.
Australian Examination Report dated Oct. 17, 2012 of Australian application No. 2008267038.
Australian Examination Report dated Oct. 24, 2012 of Australian application No. 2006326284.
Australian Examination Report dated May 29, 2013 of Australian application No. 2008311365.
Australian Written Opinion dated Sep. 15, 2009 of Singapore application No. 200804129-5.
Austrian Search Report dated Apr. 12, 2013 of Singapore application No. 20109285-6.
Austrian Written Opinion dated Apr. 12, 2013 of Singapore application No. 20109285-6.
Bandyopadhyay et al., 2006, "Interleukin-1 alpha stimulates non-amyloidogenic pathway by alpha-secretase (ADAM-10 and ADAM-17) cleavage of APP in human astrocytic cells involving p38 MAP kinase", J Neurosci Res; 84:106-118.
Bateman et al., 2007, "Requirement of aggregation propensity of Alzheimer amyloid peptides for neuronal cell surface binding", BMC Neurosci; 8:29 pp. 1-13.
Bedzyk et al., 1990, "Active site structure and antigen binding properties of idiotypically cross-reactive anti-fluorescein monoclonal antibodies", J Biol Chem; 265(1):133-138.
Bitan et al., 2003, "Amyloid beta-protein (Abeta) assembly: Abeta 40 and Abeta42 oligomerize through distinct pathways", Proc Natl Acad Sci USA; 100:330-335.
Brazilian Office Action dated Mar. 8, 2012 of Brazilian application No. PI 0619748-5.

Brown et al., 1996, "Tolerance of single, but not multiple, amino acid replacements in antibody VH CDR 2: a means of minimizing B cell wastage from somatic hypermutation?", J Immunol; 156(9):3285-3291.
Campbell, 2001, "Beta-amyloid: friend or foe", Med Hypotheses; 56(3):388-391.
Casas et al., 2004, "Massive CA1/2 neuronal loss with intraneuronal and N-terminal truncated Abeta42 accumulation in a novel Alzheimer transgenic model", Am J Pathol; 165:1289-1300.
Chilean Office Action (with English Technical Report) dated Aug. 11, 2011 of Chilean application No. 1742-2008.
Chilean Office Action (with English translation) dated Sep. 7, 2012 of Chilean application No. 10-2011.
Chilean Office Action dated Aug. 16, 2011 of application No. 1741-2008 (with English Technical Report dated Oct. 31, 2011).
Chilean Office Action dated Mar. 14, 2012 of application No. 1742-2008 (with English Technical Report).
Chilean Office Action dated Apr. 13, 2011 of application No. 3485-2006 (with English Technical Report).
Chilean Office Action dated Mar. 9, 2012 of Chilean application No. 2070-2007.
Chinese Office Action (with English translation) dated Jul. 27, 2011 of application No. 200780033976.7 dated Jul. 27, 2011.
Chinese Office Action (with English translation) dated May 14, 2012 of application No. 200680046466.9.
Chinese Office Action (with English translation) dated May 17, 2012 of application No. 200780033976.7.
Chinese Office Action (with English translation) dated Oct. 14, 2011 of Chinese application No. 200780044555.4.
Chinese Office Action (with English translation) dated Sep. 23, 2011 of Chinese Patent application No. 200780033976.7.
Chinese Office Action dated Apr. 24, 2013 of Chinese application No. 200880119317.X (with English translation).
Chinese Office Action dated Apr. 5, 2012 of Chinese application No. 2008801032036.
Chinese Office Action dated Feb. 28, 2013 of Chinese application No. 200680046466.9 (with English translation).
Chinese Office Action dated Feb. 9, 2012 of Chinese application No. 200880103155.0.
Chinese Office Action dated Jan. 29, 2013 of Chinese application No. 200980120048.3.
Chinese Office Action dated Jan. 4, 2013 of Chinese application No. 200880103155.0.
Chinese Office Action dated Jun. 14, 2012 of Chinese application No. 2008801187520.
Chinese Office Action dated Mar. 11, 2013 of Chinese application No. 2008801187520 (with English translation).
Chinese Office Action dated Mar. 7, 2013 of Chinese application No. 200780033976.7 (with English translation).
Chinese Office Action dated May 16, 2013 of Chinese application No. 200780044555.4.
Chinese Office Action dated May 22, 2013 of Chinese application No. 200880118795.9.
Chinese Office Action dated Sep. 3, 2012 of Chinese application No. 200880119317.X.
Chinese Office Action dated Aug. 26, 2012 of Chinese application No. 200880118795.9 (English translation).
Chinese Office Action dated Feb. 6, 2013 of Chinese application No. 2008801032036 (with English translation).
Clark, 1997, "IgG effector mechanisms", Chem Immuol; 65:88-110.
Cleary et al., 2005, "Natural oligomers of the amyloid-beta protein specifically disrupt cognitive function", Nat Neurosci; 8:79-84.
Colombian Office Action dated Apr. 2, 2013 of Colombian application No. 9-7328-A-1.
Colombian Office Action dated Aug. 24, 2012 of Colombian application No. 08.054.164.
Colombian Office Action dated Jan. 29, 2013 of Colombian application No. 2008054164-B (English translation).
Colombian Office Action dated Aug. 24, 2012 of Colombian application No. 08.054.164A.
Cox et al., 1994, "A directory of human germ-line V kappa segments reveals a strong bias in their usage", Eur J Immunol; 24:827-836.

(56) References Cited

OTHER PUBLICATIONS

Cuenda et al., 2007, "p38 MAP-kinases pathway regulation, function and role in human diseases", Biochimica et Biophysica Acta; 1773:1358-1375.

Culbert et al., 2006, "MAPK-activated protein kinase 2 deficiency in microglia inhibits pro-inflammatory mediator release and resultant neurotoxicity", J Biol Chem; 281(33):23658-23667.

De Pascalis et al., 2002, "Grafting of "Abbreviated" complementarity-determining regions contains specificity-determining residues essential for ligand contact to engineer a less immunogenic humanized monoclonal antibody", J Immunol; 169:3076-3084.

Delgado et al., 2008, "Vasoactive intestinal peptide protects against beta-amyloid-induced neurodegeneration by inhibiting microglia activation at multiple levels", Glia; 56:1091-1103.

Doyle et al., 2004, "Toll-like receptors induce a phagocytic gene program through p38", J Exp Med; 199:81-90.

Du et al., 2003, "Human anti-β-amyloid antibodies block beta-amyloid fibril formation and prevent β-amyloid-induced neurotoxicity", Brain; 126(9):1935-1939.

Egyptian Office Action (as sent in an email) dated Dec. 20, 2012 of Egyptian application No. PCT/55/2009.

Egyptian Office Action, as sent in an email dated Mar. 24, 2012 of Egyptian application No. PCT/794/2008.

Esler et al., 1996, "Point substitution in the central hydrophobic cluster of a human beta-amyloid congener disrupts peptide folding and abolishes plaque competence", Biochemistry; 35:13914-13921.

European Office Action dated Apr. 14, 2011of European application No. 08768370.2-1222.

European Office Action dated Dec. 13, 2011 of European application No. 07867188.0-2406.

European Office Action dated Dec. 23, 2008 of European application No. 06829456.0-2402.

European Office Action dated Jul. 11, 2012 of European application No. 06829456.0-2402.

European Office Action dated Jul. 11, 2012 of European application No. 10196705.7.

European Office Action dated Jul. 18, 2011 of European application No. 06829456.0-2402.

European Office Action dated Jul. 20, 2012 of European application No. 08768371.0-2406.

European Office Action dated Jun. 3, 2013 of European application No. 08768371.0-1412.

European Office Action dated May 21, 2012 of EP application No. 08768370.2-1222.

European Office Action dated Oct. 24, 2012 of European application No. 08836966.5-2406.

European Office Action dated Sep. 11, 2012 of European application No. 08837467.3-2406.

European Office Action dated Sep. 21, 2012 of European application No. 08838455.7-2406.

European Office Action dated Oct. 11, 2011 of European application No. 08768371.0-2406.

European Search Report dated Jul. 11, 2011 of European application No. 10196705.

European Search Report dated Mar. 4, 2013 of European application No. 12173871.0-1412.

European Search Report dated May 25, 2012 of European application No. 11192705.9-2406.

European Search Report dated Oct. 25, 2012 of European application No. 12167447.7-1222.

European Summons to Attend Oral Proceedings dated Dec. 22, 2011 of European application No. 07840408.4-2406.

Frenkel et al., 1999, "High affinity binding of monoclonal antibodies to the sequential epitope EFRH of beta-amyloid peptide is essential for modulation of fibrillar aggregation"; J Neuroimmunol; 95(1-2):136-142.

Frenkel et al., 2001, "Generation of auto-antibodies towards Alzheimer's disease vaccination", Vaccine; 19(17-19):2615-2619.

Gallagher et al., 1997, "Regulation of stress-induced cytokine production by pyridinylimidazoles; inhibition of CSBP kinase", Bioorg Med Chem; 5:49-64.

Gelinas et al., 2004, "Immunotherapy for Alzheimer's disease", Proc Natl Acad Sci; 101(suppl. 2):14657-14662.

GenBank accession No. BAE71460.1, Furkawa et al , "immunoglobulin H-chain V-region [*Mus musculus*]," [online], Jan. 6, 2006 [retrieved on Apr. 8, 2012], Retrieved from the Internet < URL: www.ncbi.nlm.nih.gov/protein/bae71460.1>.

GenBank accession No. CAA80022, Tillman et al., "immunologulin variable region [*Mus musculus* domesticus]," [online], Nov. 5, 1994 [retrieved on Apr. 8, 2012], Retrieved from the Internet < URL: www.ncbi.nlm.nih.gov/protein/caa80022>.

Gessner et al., 1998, "The IgG Fc receptor family", Ann Hematol; 76:231-248.

Gouras et al., 2000, "Intraneuronal Abeta42 accumulation in human brain", Am J Pathol; 156:15-20.

Gulf Cooperation Council Office Action dated Oct. 16, 2011, of GCC application No. GCC/P/2007/8700, with Chinese Examination Report dated Jul. 19, 2011.

Gulf Cooperation Council Office Action dated Jul. 5, 2011 of GCC application No. 7389 (English translation), with Examination Report of application GCC/P/2006/7389 dated Mar. 3, 2011.

Haass et al., 1992, "Amyloid beta-peptide is produced by cultured cells during normal metabolism", Nature; 359:322-327.

Haass et al., 2007, "Soluble protein oligomers in neurodegeneration: lesions from the Alzheimer's amyloid beta-peptide", Nature Reviews; 8:101-112.

Hazenberg et al., 2004, "Diagnostic and therapeutic approach of systemic amyloidosis", The Netherlands Journal of Medicine; 62(4):121-128.

Hensley et al., 1999, "p38 kinase is activated in the Alzheimer's disease brain", J Neurochem; 72:2053-2058.

Hermanson, 1995, Antibody modification and conjugation, Bioconjugate Techniques; Ch. 10:456-457.

Hickman et al., 2008, "Microglial dysfunction and defective beta-amyloid clearance pathways in aging Alzheimer's disease mice", J Neurosci; 28:8354-8360.

Hieter et al., 1980, "Cloned human and mouse kappa immunoglobulin constant and J region genes conserve homology in functional segments", Cell; 22(1 Pt 1):197-207.

Holmes et al., 2008, "Long-term effects of Abeta42 immunisation in Alzheimer's disease: follow-up of a randomized, placebo-controlled phase I trial", Lancet; 372:216-223.

Hu et al., 2003, "Monoclonal antibody induced liver injury in transgenic mice harbouring HBV genes", Academic Journal of Second Military Medical University; 24(2):164-167.

Hungarian Search Report dated Jul. 19, 2012 of Singapore application No. 200908189-4.

Hungarian Written Opinion dated Feb. 2, 2012 of Singaporean application No. 201002355-4.

Hungarian Written Opinion of Singaporean application No. 200908189-4 dated Nov. 10, 2011.

International Search Report dated Apr. 3, 2012 of International application No. PCT/US11/45948.

Israeli Office Action dated Apr. 2, 2012 of Israeli application No. 202567.

Israeli Office Action dated Feb. 22, 2012 of Israeli patent application No. 204836.

Israeli Office Action dated Feb. 27, 2012 of Israeli patent application No. 204837 (Un-officiall translation).

Israeli Office Action dated Jan. 4, 2012 of Israeli application No. 191230 (Un-formal translation).

Israeli Office Action dated Mar. 10, 2013 of Israeli application No. 196478.(English translation).

Israeli Office Action dated Sep. 12, 2011, of Israeli patent application No. 196748 (Informal translation).

Japanese Notice of Reasons for Rejection dated Jul. 23, 2012 of Japanese application No. 2009-519711.

Japanese Notice of Reasons for Rejection dated Jun. 11, 2012 of Japanese application No. 2008-544834.

(56) References Cited

OTHER PUBLICATIONS

Japanese Office Action (Notice of Reasons for Rejection) (with English translation) dated Oct. 17, 2012 of Japanese application No. 2010-039568.
Japanese Office Action (Notice of Reasons for Rejection) (with English translation) dated Dec. 12, 2012 of Japanese application No. 2009-531414.
Japanese Office Action dated Apr. 18, 2013 of Japanese application No. 2010-512182 (with English translation).
Japanese Office Action dated Apr. 22, 2013 of Japanese application No. 2010-512181.
Japanese Office Action dated Jun. 19, 2013 of Japanese application No. 2010-039568 (with English translation).
Kabat et al., 1991, "Sequences of proteins of immunological interest", U.S. Department of Health and Human Services; pp. XV-XVI.
Kayed et al., 2003, "Common structure of soluable amyloid oligomers implies common mechanism of pathogenesis", Science; 300:486-489.
Koenigsknecht-Talboo et al., 2008, "Rapid microglial response around amyloid pathology after systemic anti-Aβ antibody administration in PDAPP mice", Neurobiology of Disease; 28(52):14156-14164.
Lambert et al., 1998, "Diffusable, nonfibrillar ligands derived from Abetal-42 are potent central nervous system neurotoxins", Proc Natl Acad Sci USA; 95:6448-6453.
Lee et al., 1994, "A protein kinase involved in the regulation of inflammatory cytokine biosynthesis", Nature; 372:739-746.
Lee et al., 2000, "p38 map kinase regulate TNF-alpha production in huma strocytes and microglia by multiple mechanisms", Cytokine; 12:874-880.
Lee et al., 2005, "Meningoencephalitis associated with passive immunization of a transgenic murine model of Alzheimer's amyloidosis", FEBS Lett; 579:2564-2568.
Lee et al., 2006, "Targeting amyloid-beta peptide (Abeta) oligomers by passive immunization with a conformation-selective monoclonal antibody improves learning and memory in Abeta precursor protein (APP) transgenic mice", J Biol Chem; 281:4292-4299.
Legleiter et al., 2004, "Effect of different anti-Abeta antibodies on Abeta fibrillogenesis as assessed by atomic force microscopy", J Mol Biol; 335:997-1006.
Levine et al., 1993, "Thioflavine T interaction with synthetic Alzheimer's disease beta-amyloid peptides: detection of amyloid aggregation in solution", Protein Sci; 2:404-410.
Li et al., 2003, "Interleukin-1 mediates pathological effects of microglia on tau phosphorylation and on synaptophysin synthesis in cortical neurons through a p38-MAPK pathway", J Neuroscience; 23(5):16051611.
Li et al., 2004, "Tumor necrosis factor death receptor signaling cascade is required for amyloid-beta protein-induced neuron death", J Neurosci; 24:1760-1771.
Ling et al., 2003, "Amyloid precursor protein (APP) and the biology of proteolytic processing: relevance to Alzheimer's disease", Int J Biochem Cell Biol; 35:1505-1535.
Liu et al., 1998, "Amyloid beta peptide alters intracellular vesicle trafficking and cholesterol homeostasis", Proc Natl Acad Sci USA; 95:13266-13271.
Liu et al., 2009, "A novel nicotinic acetylcholine receptor subtype in basal forebrain cholinergic neurons with high sensitivity to amyloid peptides", J Neurosci; 29:918-929.
Malaysian Examination Report dated May 15, 2012 of Malaysian application No. PI 20090150 (with Search Report).
Malaysian Office Action dated Nov. 30, 2011 of Malaysian application No. PI 20081950.
Mamikonyan et al., 2007, "Amelioration of amyloid load by anti-Aβ-11 antibody binds to different β-amyloid species, inhibits fibril formation, and disaggregates preformed fibrils but not the most toxic oligomers", J Biol Chem; 282(31):22376-22386.
Matrone et al., 2008, "NGF and BDNF signaling control amyloidogenic route and Aβ production in hippocampal neurons", Proc Natl Acad Sci USA; 105(35):13139-13144.

Meberg et al., 2003, "Culturing hippocampal and cortical neurons", Methods Cell Biol; 71:111-127.
Mexican Office Action (translation) dated Nov. 22, 2011 of Mexican application No. MX/a/2009/013505.
Mexican Office Action (translation) dated Nov. 23, 2011 of Mexican application No. MX/a/2011/004131.
Mexican Office Action (with English translation) dated Mar. 8, 2013 of Mexican application Mo. MX/a/2011/004131.
Mexican Office Action of Mexican application No. MX/a/2012/007484 with English translation dated May 24, 2013.
Mexican Office Action dated Aug. 8, 2011 of application No. MX/a/2009/003468.
Mexican Office Action dated Nov. 9, 2011 of Mexican application No. MX/a/2008/007477.
Mohajeri et al., 2004, "Assessment of the bioactivity of antibodies against β-amyloid peptide in vitro and in vivo", Neurodegenerative Disease; 1:160-167.
Morgan, 2009, "The role of microglial in antibody-mediated clearance of amyloid-beta from the brain", CNS & Neurological Disorders—Drug Targets; 8:7-15.
Muhs et al., 2007, "Liposomal vaccines with conformation-specific amyloid peptide antigens define immune response and efficacy in APP transgenic mice", Proc Natl Acad Sci USA; 104:9810-9815.
Mulligan et al., 1980, "Expression of a bacterial gene in mammalian cells", Science; 209:1422-1427.
Munoz et al., 2007, "A novel p38α MAPK inhibitor suppresses brain proinflammatory cytokine up-regulation and attenuates synaptic dysfunction and behavioral deficits in an Alzheimer's disease mouse model", J Neuroinflammation; 4(21):1-14.
Munoz et al., 2010, "Targeting p38 MAPK pathway for the treatment of Alzheimer's disease", Neuropharmacology; 5(3):561-568.
New Zealand Examination Report dated Aug. 16, 2012 of application No. 601843.
New Zealand Examination Report dated Feb. 3, 2012 of New Zealand application No. 568012.
New Zealand Examination Report dated Jan. 18, 2013 of New Zealand application No. 605548.
New Zealand Examination Report dated Jul. 18, 2012 of New Zealand application No. 585110.
New Zealand Examination Report dated Jul. 19, 2011 of New Zealand application No. 594023.
New Zealand Examination Report dated Jul. 19, 2011 of New Zealand application No. 568012.
New Zealand Examination Report dated Mar. 9, 2012 of New Zealand application No. 574188.
New Zealand Examination Report dated May 8, 2012 of New Zealand application No. 581835.
New Zealand Examination Report dated Sep. 13, 2011 of New Zealand application No. 574188.
New Zealand Examination Report dated Sep. 13, 2011 of New Zealand application No. 595068.
Nimmerjahn et al., 2006, "Fc gamma receptors: old friends and new family members", Immunity; 24:19-28.
Notice of Allowance and Fees Due dated Oct. 19, 2011 of U.S. Appl. No. 12/311,505.
Oddo et al., 2003, "Triple-transgenic model of Alzheimer's disease with plaques and tangles: intracellular Abeta and synaptic dysfunction", Neuron; 39:409-421.
Office Action dated Feb. 2, 2012 of U.S. Appl. No. 12/681,673.
Office Action dated Feb. 2, 2012 of U.S. Appl. No. 12/681,683.
Office Action dated Jun. 10, 2013 of U.S. Appl. No. 13/568,995.
Office Action dated Jun. 11, 2013 of U.S. Appl. No. 13/272,603.
Office Action dated Jun. 6, 2013 of U.S. Appl. No. 13/558,256.
Office Action dated Mar. 27, 2012 of U.S. Appl. No. 12/701,199.
Office Action dated May 9, 2013 of U.S. Appl. No. 13/136,435.
Office Action dated Aug. 10, 2012 of U.S. Appl. No. 13/461,658.
Office Action dated Aug. 12, 2011 of U.S. Appl. No. 12/138,372.
Office Action dated Dec. 19, 2012 of U.S. Appl. No. 13/461,658.
Office Action dated Dec. 26, 2012 of U.S. Appl. No. 13/272,603.
Office Action dated Feb. 17, 2009 of U.S. Appl. No. 11/637,213.
Office Action dated Jan. 16, 2013 of U.S. Appl. No. 13/568,995.
Office Action dated Jul. 12, 2012 of U.S. Appl. No. 12/681,683.
Office Action dated Jul. 13, 2012 of U.S. Appl. No. 12/681,673.

(56) References Cited

OTHER PUBLICATIONS

Office Action dated Jul. 20, 2011 of U.S. Appl. No. 12/589,570.
Office Action dated Mar. 6, 2013 of U.S. Appl. No. 12/681,696.
Office Action dated Nov. 1, 2011 of U.S. Appl. No. 12/460,747.
Office Action dated Nov. 2, 2011 of U.S. Appl. No. 12/589,570.
Office Action dated Nov. 27, 2012 of U.S. Appl. No. 13/136,435.
Office Action dated Sep. 1, 2009 of U.S. Appl. No. 12/138,372.
Office Action dated Sep. 11, 2009 of U.S. Appl. No. 11/637,213.
Office Action dated Sep. 20, 2012 of U.S. Appl. No. 13/558,256.
Ohno et al., 1985, "Antigen binding specificities of antibodies are primarily determined by seven residues of VH", Proc Natl Acad Sci USA; 82(9):2945-2949.
Orgogozo et al., 2003, "Subacute meningoencephalitis in a subset of patients with AD after Abeta immunization", Neurology; 61:46-54.
Origlia et al., 2008, "Receptor for advanced glycation end product-dependent activation of p38 mitogen-activated protein kinase contributes to amyloid-β-mediated cortical synaptic dysfuntion", J Neurosci; 28(13):3521-3530.
Ozawa et al., 2002, "Enhanced $A\beta_{40}$ deposition was associated with increased $A\beta_{42/43}$ in cerebral vasculature with dutch-type hereditary cerebral hemorrhage with amyloidosis (HCHWA-D)", Ann NY Acad Sci; 977:149-154.
Pakula et al., 1989, "Genetic analysis of protein stability and function", Annu Rev Genet; 23:289-310.
Partial European Search Report dated Mar. 22, 2013 of European application No. 12189859.
Perry et al., 2001, "The role of TNF and its receptors in Alzheimer's disease", Neurobiol Aging; 22:873-883.
Peruvian Office Action (with English translation) dated Oct. 29, 2012 of Peru application No. 1010-2008.
Peruvian Office Action dated Aug. 29, 2012 of Peru application No. 001009-2008.
Peruvian Resolution and Technical Report dated Jun. 4, 2013 of Peru application No. 1010-2008.
Philippines Office Action dated Mar. 6, 2013 of Philippines application No. 1-2010-500727.
Philippines Office Action dated May 16, 2013 of Philippines application No. 1-2010-500728.
Philippines Office Action dated May 25, 2012 of Philippines application No. 12009500117.
Phillippines Office Action dated Sep. 14, 2011 of Philippines application No. 12008501065.
Pihlgren, M., "Binding of the murine monoclonal anti-Abeta antibody ACI-01-Ab7 to Abeta1-42 monomers, oligomers, and fibers", AC Immune, 2006, pp. 1-4.
Pihlgren, M., "Study ACI-ACI-2009.03 Disaggregation of Abeta1-42 fibers by ACI-01-Ab-7C2", AC Immune, 2009, pp. 1-4.
Pike et al., 1993, "Neurodegeneration induced by beta-amyloid peptides in vitro: the role of peptide assembly state", J Neurosci; 13:1676-1687.
Piorkowska and Pihlgren, "Study ACI-ACI-2009.02; Binding of ACI-01-Ab-7C2 to plaques", AC Immune, 2009, pp. 1-3.
Plant et al., 2003, "The production of amyloid beta peptide is a critical requirement for the viability of central neurons", J Neurosci; 23(13):5531-5535.
Poduslo et al., 2010, "HH domain of Alzheimer's disease Abeta provides structural basis for neuronal binding in PC12 and mouse cortical/hippocampal neurons", PLoS One; 5:e8813.
Poling et al., 2008, "Oligomers of the amyloid-beta protein disrupt working memory: confirmation with two behavioral procedures", Behav Brain Res; 193:230-234.
Ransohoff et al., 2009, "Microglial physiology: unique stimuli, specialized responses", Annu Rev Immunol; 27:119-145.
Riechmann et al., 1988, "Reshaping human antibodies for therapy", Nature; 332:323-327.
Roher et al., 1993, "β-Amyloid-(1-42) is a major component fo cerebrovascular amuloid deposits: inmplications for the pathology of Alzheimer disease", Proc Natl Acad Sci USA; 90:10836-10840.
Roitt et al., 2000, "Humanized antibodies to amyloid beta", Immunology (translation from English, Moscow, Mir, 2000, p. 110).
Russian Office Action (Notification of the results of a check on patentability) dated Aug. 7, 2012 of Russian application No. 2008128139/10 (with English translation).
Russian Office Action (translation) dated Nov. 30, 2011 of Russian application No. 2008128139.
Russian Office Action (translation dated Jul. 6, 2011) of Russian application No. 2008128139/10.
Russian Office Action dated Apr. 1, 2013 of Russian application No. 2008128139 (English translation).
Russian Office Action dated Feb. 21, 2013 of Russian application No. 2010100354 (with English translation).
Russian Office Action dated May 20, 2013 of Russian application No. 2012133155 (with English translation).
Russian Office Action dated Apr. 19, 2012 of Russian application No. 2010100354 (English translation).
Russian Office Action dated Feb. 6, 2012 of Russian application No. 2010 100 342 (translation).
Russian Office Action dated Jan. 9, 2013 of Russian application No. 2010116823 (with English translation).
Russian Office Action dated Jul. 5, 2012 of Russian application No. 2010116823 (translation).
Russian Office Action dated Jun. 6, 2012 of Russian application No. 2009104769/10 (English translation).
Russian Office Action dated May 6, 2009 of Russian application No. 2009104769/20.
Russian Office Action dated Oct. 1, 2012 of Russian application No. 2010100342.
Russian Office Action dated Sep. 9, 2011 of Russian application No. 2009104769/10.
Salloway et al., 2009, "A phase 2 multiple ascending dose trial of bapineuzumab in mild to moderate Alzheimer's disease", Neurology; 73:2061-2070.
Selkoe, 2002, "Alzheimer's disease is a synaptic failure", Science; 298(5594):789-791.
Shankar et al., 2007, "Natural oligomers of the Alzheimer amyloid-beta protein induce reversible synapse loss by modulating an NMDA-type glutamate receptor-dependent signaling pathway", J Neurosci; 27:2866-2875.
Shields et al., 2001, "High resolution mapping of the binding site on human IgG1 for Fc gamma RI, Fc gamma RII, Fc gamma RIII, and FcRn and design of IgG1 variants with improved binding to the Fc gamma R", J Biol Chem; 276:6591-6604.
Shinoda et al., 1981, "Complete amino acid sequence of the Fc region of a human delta chain", Proc Natl Acad Sci USA; 78(2):785-789.
Simon et al., 1985, "A modified assay for interleukin-1 (IL-1)", J Immunol Methods; 84:85-94.
Singapore Examination Report dated Feb. 10, 2012 of Singapore application No. 200908190-2.
Singapore Written Opinion dated Sep. 7, 2012 of Singapore application No. 201002371-1.
Spires-Jones et al., 2009, "Passive immunotherapy rapidly increases structural plasticity in a mouse model of Alzheimer disease", Neurobiol Dis; 33:213-220.
Strittmatter et al., 1993, "Apolipoprotein E: high-avidity binding to beta-amyloid and increased frequency of type 4 allele in late-onset familial Alzheimer disease", Proc Natl Acad Sci USA; 90:1977-1981.
Taiwanese Office Action (with English Search Report) dated Oct. 23, 2012 of Taiwanese application No. 095146548.
Taiwanese Office Action dated Mar. 20, 2013 of Taiwanese application No. 097121924 (English translation).
Taiwanese Search Report dated Mar. 18, 2013 of Taiwanese application No. 097121924 (English translation).
The International Federation of Alzheimer's Disease and Related Disorders Societies I, 2009, World Alzheimer Report—2009 Executive Summary, pp. 1-21.
The Merck Index, 2006, "An Encyclopedia of Chemicals, Drugs, and Biological", 14th Edition; pp. 1422-1423, 578, and 746.
Tomlinson et al., 1992, "The repertoire of human germline VH sequences reveals about 50 groups of VH segments with different hypervariable loops", J Mol Biol; 227:776-798.

(56) References Cited

OTHER PUBLICATIONS

Townsend et al., 2006, "Effects secreted oligomers of amyloid beta-protein on hippocampal synaptic plasticity: a potent role for trimers", J Physiol; 572:477-492.

Turner et al., 2003, "Roles of amyloid precursor protein and its fragments in regulating neural activity, plasticity and memory", Prog Neurobiol; 70:1-32.

Ukrainian Office Action dated Dec. 1, 2011 of Ukrainian application No. 200808792.

Ukrainian Office Action dated Jun. 1, 2011 of Ukrainian application No. 200808792.

Ukrainian Office Action dated Oct. 3, 2011 of Ukrainian application No. 200900880 (with English translation).

Varisco et al., 2010, "MABT5102A is an effector-reduced anti-AB antibody with unique binding properties that promotes neuroprotection and glial engulfment of AB", Abstract presented at the 3rd Conference Clinical Trials on Alzheimer's Disease, Nov. 3-5, 2010, Toulouse, France. The Journal of Nutrition, Health, & Aging; 14(Suppl. 2):S5.

Vellas et al., 2009, "Long-term follow-up of patients immunized with AN1792: reduced functional decline in antibody responders", Curr Alzheimer Res; 6:144-151.

Vietnamese Office Action dated Feb. 9, 2012 of Vietnamese application No. 1-2008-01736.

Vietnamese Office Action dated Jul. 12, 2012 of Vietnamese application No. 1-2008-01736.

Walsh et al., 2002, "Naturally secreted oligomers of amyloid beta protein potently inhibit hippocampal long-term potentiation in vivo", Nature; 416:535-539.

Walsh et al., 2005, "The role of cell-derived oligomers of Abeta in Alzheimer's disease and avenues for therapeutic intervention", Biochem Soc Trans; 33:1087-1090.

Wang et al., 2004, "Block of long-term potentiation by naturally secreted and synthetic amyloid beta-peptide in hippocampal slices is mediated via activation of the kinases c-Jun N-terminal kinase, cyclin-dependent kinase5, and p38 mitogen-activated protein kinase as well as metabotropic glutamate receptor type 5", J Neurosci; 24:3370-3378.

Wikipedia, The Free Encyclopedia, 2012, "Glaucoma," [on-line], Jan. 30, 2012 [retrieved on Jan. 30, 2012], pp. 1-18, Retrieved from the Internet:< URL: en.wikipedia.org/wiki/Glaucoma>.

Wirths et al., 2001, "Intraneuronal Abeta accumulation precedes plaque formation in beta-amyloid precursor protein and presenilin-1 double-transgenic mice", Neurosci Lett; 306:116-120.

Written Opinion dated Apr. 3, 2012 of International application No. PCT/US11/45948.

Written Opinion dated Jul. 8, 2011 of Singapore application No. 200908190-2.

Wu et al., 1999, "Humanization of a murine monoclonal antibody by simultaneous optimization of framework and CDR residues", J Mol Biol; 294:151-162.

\* cited by examiner

SEQUENCE LISTING

```
<160> NUMBER OF SEQ ID NOS: 20

<210> SEQ ID NO 1
<211> LENGTH: 14
<212> TYPE: PRT
<213> ORGANISM: Homo sapiens
<220> FEATURE:
<221> NAME/KEY: MISC_FEATURE
<223> OTHER INFORMATION: antigenic peptide AB 22-35

<400> SEQUENCE: 1

Glu Asp Val Gly Ser Asn Lys Gly Ala Ile Ile Gly Leu Met
1               5                   10

<210> SEQ ID NO 2
<211> LENGTH: 12
<212> TYPE: PRT
<213> ORGANISM: Homo sapiens
<220> FEATURE:
<221> NAME/KEY: MISC_FEATURE
<223> OTHER INFORMATION: antigenic peptide AB 29-40

<400> SEQUENCE: 2

Gly Ala Ile Ile Gly Leu Met Val Gly Gly Val Val
1               5                   10

<210> SEQ ID NO 3
<211> LENGTH: 28
<212> TYPE: PRT
<213> ORGANISM: Homo sapiens
<220> FEATURE:
<221> NAME/KEY: MISC_FEATURE
<223> OTHER INFORMATION: Amyloid beta peptide fragment AB 1-28

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

<210> SEQ ID NO 4
<211> LENGTH: 24
<212> TYPE: PRT
<213> ORGANISM: Homo sapiens
<220> FEATURE:
<221> NAME/KEY: MISC_FEATURE
<223> OTHER INFORMATION: Amyloid beta peptide fragment AB 17-40
```

```
<400> SEQUENCE: 4

Leu Val Phe Phe Ala Glu Asp Val Gly Ser Asn Lys Gly Ala Ile Ile
1               5                   10                  15

Gly Leu Met Val Gly Gly Val Val
            20

<210> SEQ ID NO 5
<211> LENGTH: 40
<212> TYPE: PRT
<213> ORGANISM: Homo sapiens
<220> FEATURE:
<221> NAME/KEY: MISC_FEATURE
<223> OTHER INFORMATION: Amyloid beta peptide fragment AB 1-40

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 6
<211> LENGTH: 42
<212> TYPE: PRT
<213> ORGANISM: Homo sapiens
<220> FEATURE:
<221> NAME/KEY: MISC_FEATURE
<223> OTHER INFORMATION: Amyloid beta peptide fragment AB 1-42

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 7
<211> LENGTH: 109
<212> TYPE: PRT
<213> ORGANISM: Mus musculus
<220> FEATURE:
<221> NAME/KEY: MISC_FEATURE
<223> OTHER INFORMATION: Light chain variable domain of ACI-11-Ab-9

<400> SEQUENCE: 7

Gln Ala Val Val Thr Gln Glu Ser Ala Leu Thr Thr Ser Pro Gly Gly
1               5                   10                  15

Thr Val Ile Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Ser Asn Arg Ala Pro Gly Val Pro Val Arg Phe
    50                  55                  60

Ser Gly Ser Leu Ile Gly Asp Lys Ala Ala Leu Thr Ile Thr Gly Ala
65                  70                  75                  80

Gln Thr Glu Asp Asp Ala Met Tyr Phe Cys Ala Leu Trp Tyr Ser Thr
                85                  90                  95

His Tyr Val Phe Gly Gly Gly Thr Lys Val Thr Val Leu
            100                 105
```

<210> SEQ ID NO 8
<211> LENGTH: 117
<212> TYPE: PRT
<213> ORGANISM: Mus musculus
<220> FEATURE:
<221> NAME/KEY: MISC_FEATURE
<223> OTHER INFORMATION: Heavy chain variable domain of ACI-11-Ab-9

<400> SEQUENCE: 8

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
                20                  25                  30

Thr Ile His Trp Met Lys Gln Arg Pro Glu Gln Gly Leu Glu Trp Ile
            35                  40                  45

Gly Tyr Ile Tyr Pro Arg Asp Gly Ser Thr Lys Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Asp Tyr Gly Tyr Ala Phe Asp Tyr Trp Gly Gln Gly Thr Thr
                100                 105                 110

Leu Thr Val Ser Ser
        115

<210> SEQ ID NO 9
<211> LENGTH: 109
<212> TYPE: PRT
<213> ORGANISM: Mus musculus
<220> FEATURE:
<221> NAME/KEY: MISC_FEATURE
<223> OTHER INFORMATION: Light chain variable domain of ACI-12-Ab-11

<400> SEQUENCE: 9

Gln Ala Val Val Thr Gln Glu Ser Ala Leu Thr Thr Ser Pro Gly Gly
1               5                   10                  15

Thr Val Ile Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Gly Thr Ser Asn Arg Ala Pro Gly Val Pro Val Arg Phe
        50                  55                  60

Ser Gly Ser Leu Ile Gly Asp Lys Ala Ala Leu Thr Ile Thr Gly Ala
65                  70                  75                  80

Gln Thr Glu Asp Asp Ala Met Tyr Phe Cys Ala Leu Trp Tyr Ser Thr
                85                  90                  95

His Tyr Val Phe Gly Gly Gly Thr Lys Val Thr Val Leu
                100                 105

<210> SEQ ID NO 10
<211> LENGTH: 117
<212> TYPE: PRT
<213> ORGANISM: Mus musculus
<220> FEATURE:
<221> NAME/KEY: MISC_FEATURE
<223> OTHER INFORMATION: Heavy chain variable domain of ACI-12-Ab-11

<400> SEQUENCE: 10

Gln Val Gln Leu Gln Gln Ser Asp Ala Glu Leu Val Lys Pro Gly Ala

```
                1               5                  10                 15
Ser Val Lys Ile Ser Cys Lys Val Ser Gly Tyr Thr Phe Thr Asp His
                      20                  25                  30

Thr Ile His Trp Met Lys Gln Arg Pro Glu Gln Gly Leu Glu Trp Ile
            35                  40                  45

Gly Tyr Ile Tyr Pro Arg Asp Gly Ser Thr Tyr Asn Glu Lys Phe
        50                  55                  60

Lys Gly Lys Ala Thr Leu Thr Ala Asp Lys Ser Ser Thr Ala Tyr
 65                  70                  75                  80

Met Gln Leu Asn Ser Leu Thr Ser Glu Asp Ser Ala Val Tyr Phe Cys
                    85                  90                  95

Ala Arg Asp Tyr Gly Tyr Ala Phe Asp Tyr Trp Gly Gln Gly Thr Thr
                100                 105                 110

Leu Thr Val Ser Ser
        115

<210> SEQ ID NO 11
<211> LENGTH: 14
<212> TYPE: PRT
<213> ORGANISM: Mus musculus
<220> FEATURE:
<221> NAME/KEY: MISC_FEATURE
<223> OTHER INFORMATION: Light chain CDR1

<400> SEQUENCE: 11

Arg Ser Ser Thr Gly Ala Val Thr Thr Ser Asn Tyr Ala Asn
1               5                   10

<210> SEQ ID NO 12
<211> LENGTH: 7
<212> TYPE: PRT
<213> ORGANISM: Mus musculus
<220> FEATURE:
<221> NAME/KEY: MISC_FEATURE
<223> OTHER INFORMATION: Light chain CDR2

<400> SEQUENCE: 12

Gly Thr Ser Asn Arg Ala Pro
1               5

<210> SEQ ID NO 13
<211> LENGTH: 9
<212> TYPE: PRT
<213> ORGANISM: Mus musculus
<220> FEATURE:
<221> NAME/KEY: MISC_FEATURE
<223> OTHER INFORMATION: Light chain CDR3

<400> SEQUENCE: 13

Ala Leu Trp Tyr Ser Thr His Tyr Val
1               5

<210> SEQ ID NO 14
<211> LENGTH: 10
<212> TYPE: PRT
<213> ORGANISM: Mus musculus
<220> FEATURE:
<221> NAME/KEY: MISC_FEATURE
<223> OTHER INFORMATION: Heavy chain CDR1

<400> SEQUENCE: 14

Gly Tyr Thr Phe Thr Asp His Thr Ile His
1               5                   10
```

```
<210> SEQ ID NO 15
<211> LENGTH: 17
<212> TYPE: PRT
<213> ORGANISM: Mus musculus
<220> FEATURE:
<221> NAME/KEY: MISC_FEATURE
<223> OTHER INFORMATION: Heavy chain CDR2

<400> SEQUENCE: 15

Tyr Ile Tyr Pro Arg Asp Gly Ser Thr Lys Tyr Asn Glu Lys Phe Lys
1               5                   10                  15

Gly

<210> SEQ ID NO 16
<211> LENGTH: 8
<212> TYPE: PRT
<213> ORGANISM: Mus musculus
<220> FEATURE:
<221> NAME/KEY: MISC_FEATURE
<223> OTHER INFORMATION: Heavy chain CDR3

<400> SEQUENCE: 16

Asp Tyr Gly Tyr Ala Phe Asp Tyr
1               5

<210> SEQ ID NO 17
<211> LENGTH: 327
<212> TYPE: DNA
<213> ORGANISM: Mus musculus
<220> FEATURE:
<221> NAME/KEY: misc_feature
<223> OTHER INFORMATION: ACI-11-Ab-9 light chain variable domain coding
      sequence

<400> SEQUENCE: 17
caggcagttg tgactcagga atctgcactc accacgtcac ctggtggaac agtcatactc    60
acttgtcgct caagtactgg ggctgttaca actagtaact atgccaactg ggtccaagaa   120
aaaccagatc atttattcac tggtctaata ggtggtacca gcaaccgagc tccaggtgtt   180
cctgtcagat tctcaggctc cctgattgga acaaggctg ccctcaccat cacaggggca    240
cagactgagg atgatgcaat gtatttctgt gctctatggt acagcaccca ttatgttttc   300
ggcggtggaa ccaaggtcac tgtccta                                       327

<210> SEQ ID NO 18
<211> LENGTH: 351
<212> TYPE: DNA
<213> ORGANISM: Mus musculus
<220> FEATURE:
<221> NAME/KEY: misc_feature
<223> OTHER INFORMATION: ACI-11-Ab-9 heavy chain variable domain coding
      sequence

<400> SEQUENCE: 18
caggttcagc tgcagcagtc tgacgctgag ttggtgaaac tggagcttc agtgaagata     60 tcctgcaagg tttctggcta caccttcact gaccatacta ttcactggat gaagcagagg   120
cctgaacagg gcctggaatg gattggatat atttatccta gagatggtag tactaagtac   180
aatgagaagt tcaagggcaa ggccacattg actgcagaca atcctccag cacagcctac    240 atgcagctca acagcctgac atctgaggac tctgcagtct atttctgtgc aagagactat   300
ggttacgcct ttgactactg gggccaaggc accactctca cagtctcctc a            351

<210> SEQ ID NO 19
<211> LENGTH: 327
```

```
<212> TYPE: DNA
<213> ORGANISM: Mus musculus
<220> FEATURE:
<221> NAME/KEY: misc_feature
<223> OTHER INFORMATION: ACI-12-Ab-11 light chain variable domain coding
      sequence

<400> SEQUENCE: 19
caggccgttg tgactcagga atctgcactc accacgtccc ctggtggaac agtcatactc      60
acttgtcgct caagtactgg ggctgttaca actagtaact atgccaactg ggtccaagaa     120
aaaccagatc atttattcac tggtctaata ggtggtacca gcaaccgagc tccaggtgtt     180
cctgtcagat tctcaggctc cctgattgga gacaaggctg ccctcaccat cacagggca      240 cagactgagg atgatgcaat gtatttctgt gctctatggt acagcaccca ttatgttttc     300
ggcggtggaa ccaaggtcac tgtccta                                         327

<210> SEQ ID NO 20
<211> LENGTH: 351
<212> TYPE: DNA
<213> ORGANISM: Mus musculus
<220> FEATURE:
<221> NAME/KEY: misc_feature
<223> OTHER INFORMATION: ACI-12-Ab-11 heavy chain variable domain coding
      sequence

<400> SEQUENCE: 20
caggttcagc tgcagcagtc tgacgctgag ttggtgaaac ctggagcttc agtgaagata      60
tcctgcaagg tttctggcta caccttcact gaccatacta ttcactggat gaagcagagg     120
cctgaacagg gcctggaatg gattggatat atttatccta gagatggtag tactaagtac     180
aatgagaagt tcaagggcaa ggccacattg actgcagaca atcctccag cacagcctac      240 atgcagctca acagcctgac atctgaggac tctgcagtct atttctgtgc aagagactat     300
ggttacgcct ttgactactg gggccaaggc accactctca cagtctcctc a              351
```

MONOCLONAL ANTIBODY

CROSS-REFERENCE TO RELATED APPLICATION

This application claims the benefit of U.S. Provisional Application No. 60/943,541, filed Jun. 12, 2007, and U.S. Provisional Application No. 60/943,790, filed Jun. 13, 2007.

The present invention is related to methods and compositions for the therapeutic and diagnostic use in the treatment of diseases and disorders which are caused by or associated with amyloid or amyloid-like proteins including amyloidosis, a group of disorders and abnormalities associated with amyloid protein such as Alzheimer's disease.

Amyloidosis is not a single disease entity but rather a diverse group of progressive disease processes characterized by extracellular tissue deposits of a waxy, starch-like protein called amyloid, which accumulates in one or more organs or body systems. As the amyloid deposits build up, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs in people who have a chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease, and leprosy.

Amyloid protein fibrils, which account for about 90% of the amyloid material, comprise one of several different types of proteins. Certain of these proteins are capable of folding into so-called "beta-pleated" sheet fibrils, a unique protein configuration which exhibits binding sites for Congo red resulting in the unique staining properties of the amyloid protein. In addition, amyloid deposits are closely associated with the amyloid P (pentagonal) component (AP), a glycoprotein related to normal serum amyloid P (SAP), and with sulfated glycosaminoglycans (GAG), complex carbohydrates of connective tissue.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and others, including macular degeneration.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators (McGeer et al., 1994).

Alzheimer's Disease (AD) is a neurological disorder primarily thought to be caused by amyloid plaques, an accumulation of abnormal deposit of proteins in the brain. The most frequent type of amyloid found in the brain of affected individuals is composed primarily of A$\beta$ fibrils. Scientific evidence demonstrates that an increase in the production and accumulation of beta-amyloid protein in plaques leads to nerve cell death, which contributes to the development and progression of AD. Loss of nerve cells in strategic brain areas, in turn, causes reduction in the neurotransmitters and impairment of memory. The proteins principally responsible for the plaque build up include amyloid precursor protein (APP) and two presenilins (presenilin I and presenilin II). Sequential cleavage of the amyloid precursor protein (APP), which is constitutively expressed and catabolized in most cells, by the enzymes $\beta$ and $\gamma$ secretase leads to the release of a 39 to 4$\beta$ amino acid A$\beta$ peptide. The degradation of APPs likely increases their propensity to aggregate in plaques. The A$\beta$(1-42) fragment in particular has a high propensity of building aggregates due to two very hydrophobic amino acid residues at its C-terminus. The A$\beta$(1-42) fragment is therefore believed to be mainly involved and responsible for the initiation of neuritic plaque formation in AD and to have, therefore, a high pathological potential. There is therefore a need for specific antibodies that can target and diffuse amyloid plaque formation.

The symptoms of AD manifest slowly and the first symptom may only be mild forgetfulness. In this stage, individuals may forget recent events, activities, the names of familiar people or things and may not be able to solve simple math problems. As the disease progresses, symptoms are more easily noticed and become serious enough to cause people with AD or their family members to seek medical help. Midstage symptoms of AD include forgetting how to do simple tasks such as grooming, and problems develop with speaking, understanding, reading, or writing. Later stage AD patients may become anxious or aggressive, may wander away from home and ultimately need total care.

Presently, the only definite way to diagnose AD is to identify plaques and tangles in brain tissue in an autopsy after death of the individual. Therefore, doctors can only make a diagnosis of "possible" or "probable" AD while the person is still alive. Using current methods, physicians can diagnose AD correctly up to 90 percent of the time using several tools to diagnose "probable" AD. Physicians ask questions about the person's general health, past medical problems, and the history of any difficulties the person has carrying out daily activities. Behavioral tests of memory, problem solving, attention, counting, and language provide information on cognitive degeneration and medical tests such as tests of blood, urine, or spinal fluid, and brain scans can provide some further information.

The management of AD consists of medication-based and non-medication based treatments. Treatments aimed at changing the underlying course of the disease (delaying or reversing the progression) have so far been largely unsuccessful. Medicines that restore the deficit (defect), or malfunctioning, in the chemical messengers of the nerve cells (neurotransmitters), in particular the cholinesterase inhibitors (ChEIs) such as tacrine and rivastigmine, have been shown to improve symptoms. ChEIs impede the enzymatic degradation of neurotransmitters thereby increasing the amount of chemical messengers available to transmit the nerve signals in the brain.

For some people in the early and middle stages of the disease, the drugs tacrine (COGNEX®, Morris Plains, N.J.), donepezil (ARICEPT®, Tokyo, JP), rivastigmine (EX- ELON®, East Hanover, N.J.), or galantamine (REMINYL®, New Brunswick, N.J.) may help prevent some symptoms from becoming worse for a limited time. Another drug, memantine (NAMENDA®, New York, N.Y.), has been approved for treatment of moderate to severe AD. Medications are also available to address the psychiatric manifestations of AD. Also, some medicines may help control behavioral symptoms of AD such as sleeplessness, agitation, wandering, anxiety, and depression. Treating these symptoms often makes patients more comfortable and makes their care easier for caregivers. Unfortunately, despite significant treatment advances showing that this class of agents is consistently better than a placebo, the disease continues to progress, and the average effect on mental functioning has only been modest. Many of the drugs used in AD medication such as, for example, ChEIs also have side effects that include gastrointestinal dysfunction, liver toxicity and weight loss.

Other diseases that are based on or associated with the accumulation and deposit of amyloid-like protein are mild cognitive impairment, Lewy body dementia (LBD), amyotrophic lateral sclerosis (ALS), inclusion-body myositis (IBM) and macular degeneration, in particular age-related macular degeneration (AMD).

Mild cognitive impairment (MCI) is a general term most commonly defined as a subtle but measurable memory disorder. A person with MCI experiences memory problems greater than normally expected with aging, but does not show other symptoms of dementia, such as impaired judgment or reasoning. MCI is a condition that frequently reflects a pre-clinical stage of AD.

The deposition of β-amyloid within the entorhinal cortex (EC) is believed to play a key role in the development of mild cognitive impairment (MCI) in the elderly. This is in line with the observation that the CSF-A Aβ(1-42) levels decline significantly once AD becomes clinically overt. In contrast to CSF-Aβ(1-42) CSF-tau levels are significantly increased in the MCI stage, and these values continue to be elevated thereafter, indicating that increased levels of CSF-tau may help in detecting MCI subjects who are predicted to develop AD.

Lewy body dementia (LBD) is a neurodegenerative disorder that can occur in persons older than 65 years of age, which typically causes symptoms of cognitive (thinking) impairment and abnormal behavioural changes. Symptoms can include cognitive impairment, neurological signs, sleep disorder, and autonomic failure. Cognitive impairment is the presenting feature of LBD in most cases. Patients have recurrent episodes of confusion that progressively worsen. The fluctuation in cognitive ability is often associated with shifting degrees of attention and alertness. Cognitive impairment and fluctuations of thinking may vary over minutes, hours, or days.

Lewy bodies are formed from phosphorylated and non-phosphorylated neurofilament proteins; they contain the synaptic protein alpha-synuclein as well as ubiquitin, which is involved in the elimination of damaged or abnormal proteins. In addition to Lewy Bodies, Lewy neurites, which are inclusion bodies in the cell processes of the nerve cells, may also be present. Amyloid plaques may form in the brains of patients afflicted with LBD, however they tend to be fewer in number than seen in patients with Alzheimer's disease. Neurofibrillary tangles, the other micropathological hallmark of AD, are not a main characteristic of LBD but are frequently present in addition to amyloid plaques.

Amyotrophic lateral sclerosis (ALS) is characterized by degeneration of upper and lower motor neurons. In some ALS patients, dementia or aphasia may be present (ALS-D). The dementia is most commonly a frontotemporal dementia (FTD), and many of these cases have ubiquitin-positive, tau-negative inclusions in neurons of the dentate gyrus and superficial layers of the frontal and temporal lobes.

Inclusion-body myositis (IBM) is a crippling disease usually found in people over age 50, in which muscle fibers develop inflammation and begin to atrophy—but in which the brain is spared and patients retain their full intellect. Two enzymes involved in the production of amyloid-β protein were found to be increased inside the muscle cells of patients with this most common, progressive muscle disease of older people, in which amyloid-β is also increased.

Another disease that is based on or associated with the accumulation and deposit of amyloid-like protein is macular degeneration.

Macular degeneration is a common eye disease that causes deterioration of the macula, which is the central area of the retina (the paper-thin tissue at the back of the eye where light-sensitive cells send visual signals to the brain). Sharp, clear, 'straight ahead' vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans age 40 and older have advanced AMD, and another 7.3 million people with intermediate AMD are at substantial risk for vision loss. The government estimates that by 2020 there will be 2.9 million people with advanced AMD. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. Macugen® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of drusen between the basal lamina of the retinal pigmented epithelium (RPE) and Bruch's membrane (BM). Recent studies conducted by Anderson et al. have confirmed that drusen contains amyloid beta. (Experimental Eye Research 78 (2004) 243-256).

Ongoing research continues with studies exploring environmental, genetic, and dietary factors that may contribute to AMD. New treatment strategies are also being explored, including retinal cell transplants, drugs that will prevent or slow down the progress of the disease, radiation therapy, gene therapies, a computer chip implanted in the retina that may help stimulate vision and agents that will prevent the growth of new blood vessels under the macula.

An important factor to consider when developing new drugs is the ease of use for the target patients. Oral drug delivery, specifically tablets, capsules and softgels-, account for 70% of all dosage forms consumed because of patient convenience. Drug developers agree that patients prefer oral delivery rather than subjecting themselves to injections or other, more invasive forms of medicinal administration. Formulations resulting in low dosing intervals (i.e. once a day or sustained release) are also preferable. The ease of administering antibiotics in oral dosage forms results in an increase of patient compliance during treatment.

What is needed are effective methods and compositions for the generation of highly specific and highly effective antibodies, which is a prerequisite if the antibodies are to be provided in an oral dosage form. Preferably such antibodies would recognize specific epitopes on various antigens such as amyloid protein.

What is also needed therefore, are effective compositions and methods for addressing the complications associated with diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and others, including macular degeneration. In particular what is need are specialized and highly effective antibodies capable of counteracting the physiological manifestations of the disease such as the formation of plaques associated with aggregation of fibers of the amyloid or amyloid-like peptide.

Anti-amyloid antibodies elicited by the inoculation of $A\beta_{1-42}$ mixed with Freund complete or incomplete adjuvant had proved capable to reduce the amyloid burden in transgenic mice for human Alzheimer disease (Schenk et al., 1999).

Intraperitonal inoculation of tetrapalmitoylated $A\beta_{1-16}$ reconstituted in liposomes to NORBA transgenic mice elicited significant titers of anti-amyloid antibodies, which also proved capable to solubilize amyloid fibers and plaques in vitro and in vivo. (Nicolau et al., 2002).

A possible mechanism by which the dissolution of amyloid plaques and fibres occurred was first suggested by Bard et al., (2000), who advanced the conclusion, based upon their data, that the antibodies opsonized the plaques, which were subsequently destroyed by the macrophages of the microglia. De Mattos et al., (2001) indicated that a MAb directed against the central domain of β-amyloid was able to bind and completely sequester plasma amyloid. They argued that the presence of these mAbs in circulation shifted the equilibrium of Aβ between brain and plasma, favoring the peripheral clearing and catabolism instead of deposition within the brain.

The present invention provides novel methods and compositions comprising highly specific and highly effective antibodies having the ability to specifically recognize and bind to specific β-amyloid proteins. The antibodies enabled by the teaching of the present invention are particularly useful for the treatment of diseases and disorders in a subject, which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, hereditary cerebral hemorrhage with amyloidosis Dutch type, Parkinson's disease, HIV-related dementia, ALS (amyotropic lateral sclerosis), inclusion-body myositis (IBM), Adult Onset Diabetes; senile cardiac amyloidosis; endocrine tumors, and others, including macular degeneration, to name just a few.

Moreover, the present invention provides novel methods and compositions for retaining or increasing the cognitive memory capacity in a subject, particularly a mammal exhibiting an amyloid-associated disease or condition comprising administering to a subject, particularly a mammal, more particularly a human in need of such a treatment, a therapeutically effective amount of a monoclonal antibody according to the invention.

SUMMARY OF THE INVENTION

The present invention makes use of antigen presentations that result in enhanced exposure and stabilization of a preferred antigen conformation, which ultimately results in antibodies with unique properties.

In one embodiment of the invention, an antibody is provided including any functionally equivalent antibody or functional parts thereof, or, more particularly, a monoclonal antibody including any functionally equivalent antibody or functional parts thereof, which has been raised against a supramolecular antigenic construct comprising an antigenic peptide corresponding to the amino acid sequence of the β-amyloid peptide, particularly of β-amyloid peptide $A\beta_{22-35}$ and $A\beta_{29-40}$, respectively, modified with a hydrophilic moiety such as, for example, polyethylene glycol (PEG), wherein said hydrophilic moiety, is covalently bound to each of the termini of the antigenic peptide through at least one, particularly one or two amino acids such as, for example, lysine, glutamic acid and cysteine or any other suitable amino acid or amino acid analogue capable of serving as a connecting device for coupling the hydrophilic moiety to the peptide fragment. When a PEG is used as the hydrophilic moiety, the free PEG termini may be covalently bound to phosphatidylethanolamine or any other compound suitable to function as the anchoring element, for example to embed the antigenic construct in the bilayer of a liposome.

In one embodiment of the invention, an antibody is provided, particularly a monoclonal antibody including any functionally equivalent antibody or functional parts thereof, which antibody recognizes and binds to a conformational epitope and binds to polymeric soluble amyloid and to amyloid fibrils or fibers, respectively, particularly to polymeric soluble amyloid Aβ peptides and amyloid Aβ fibrils or fibers, respectively.

In one embodiment of the invention, an antibody is provided, particularly a monoclonal antibody including any functionally equivalent antibody or functional parts thereof, which antibody recognizes and binds to a conformational epitope preferentially displayed on polymeric soluble amyloid and oligomeric amyloid peptides, respectively, but also on amyloid fibrils or fibers, particularly on polymeric soluble amyloid Aβ peptides and oligomeric amyloid Aβ peptides comprising a plurality of monomeric Aβ1-42 peptides, and on amyloid fibrils or fibers incorporating a plurality of said oligomeric peptides, respectively.

The inheritance of the ε4 allele of the apolipoproteinE (apoE4) protein is a strong genetic risk factor for AD. This protein is able to bind to amyloid and is known to be involved in both the clearance of Aβ across the blood-brain-barrier as well as the promotion of Aβ deposition. In reverse, the binding of amyloid maps in the hydrophobic lipoprotein binding region of ApoE and this association dramatically diminish the overall lipid binding ability of ApoE.

Accordingly, it is a further embodiment of the invention to provide an antibody, particularly a monoclonal antibody, including any functionally equivalent antibody or functional parts thereof as described herein, which antibody is capable of inhibiting or otherwise lessening the interaction of amyloid with ApoE4 in the brain of a subject, particularly a mammal, but especially a human, particularly in the brain of a subject, particularly a mammal, but especially a human suffering from a disease or condition associated with increased concentration of Aβ in the brain.

Accordingly, it is a further embodiment of the invention to provide an antibody, particularly a monoclonal antibody, including any functionally equivalent antibody or functional parts thereof as described herein, which antibody is capable of inhibiting or otherwise lessening the interaction of amyloid with ApoE4 in the brain of a subject, particularly a mammal, but especially a human, particularly in the brain of a subject, particularly a mammal, but especially a human suffering from a disease or condition associated with increased concentration of Aβ in the brain. The antibody according to the present invention, particularly a monoclonal antibody including any functionally equivalent antibody or functional parts thereof, thus preferentially binds to polymeric soluble amyloid and amyloid fibrils or fibers, respectively, particularly to polymeric soluble Aβ peptides comprising a plurality of $Aβ_{1-42}$ monomeric peptides and Aβ fibrils or fibers incorporating a plurality of said polymeric peptides, respectively.

In one embodiment the invention relates to an antibody, as described herein, particularly a monoclonal antibody including any functionally equivalent antibody or functional parts thereof, which antibody binds to Aβ monomeric peptides having at least 10, particularly at least 20, more particularly at least 30, even more particularly at least 40 amino acid residues, and/or to soluble polymeric amyloid peptides comprising a plurality of said amyloid monomeric peptides and/or to amyloid fibers or fibrils incorporating a plurality of said polymeric peptides but especially to an $Aβ_{1-42}$ monomeric peptide and polymeric soluble Aβ peptides comprising a plurality of $Aβ_{1-42}$ monomeric peptides and Aβ fibrils or fibers incorporating a plurality of said polymeric peptides, and shows essentially no binding to Aβ monomeric peptides having 8 or fewer amino acid residues.

In one specific embodiment, the invention relates to an antibody as described herein, particularly a monoclonal antibody including any functionally equivalent antibody or functional parts thereof, which antibody binds to Aβ monomeric peptides having at least 30, even more particularly at least 40 amino acid residues, and/or to soluble polymeric amyloid peptides comprising a plurality of said amyloid monomeric peptides and/or to amyloid fibers or fibrils incorporating a plurality of said polymeric peptides but especially to an $Aβ_{1-42}$ monomeric peptide and polymeric soluble Aβ peptides comprising a plurality of $β_{1-42}$ monomeric peptides and Aβ fibrils or fibers incorporating a plurality of said polymeric peptides, but shows essentially no binding to Aβ monomeric peptide 17-40.

In another specific embodiment of the invention, an antibody is provided as described herein, particularly a monoclonal antibody including any functionally equivalent antibody or functional parts thereof, which antibody binds to Aβ monomeric peptide 1-42 and polymeric soluble Aβ peptides comprising a plurality of $Aβ_{1-42}$ monomeric peptides and Aβ fibrils or fibers incorporating a plurality of said polymeric peptides, but shows a substantially weaker binding to Aβ monomeric peptide 1-28.

In another specific embodiment of the invention, an antibody is provided as described herein, particularly a monoclonal antibody including any functionally equivalent antibody or functional parts thereof, which antibody binds to Aβ monomeric peptide 1-42 and polymeric soluble Aβ peptides comprising a plurality of $Aβ_{1-42}$ monomeric peptides and Aβ fibrils or fibers incorporating a plurality of said polymeric peptides, but shows a substantially weaker binding to Aβ monomeric peptide 1-28 and essentially no binding to Aβ monomeric peptide 17-40.

By a "substantially weaker binding" a binding is meant, which is at least about 60%, particularly at least about 65%, more particularly at least about 70%, even more particularly at least about 80%, but especially at least about 90% and up to 100% less than the binding to Aβ monomeric peptide 1-42.

By "essentially no binding" a binding is meant, which is at least about 85%, particularly at least about 90%, more particularly at least about 95%, even more particularly at least about 98%, but especially at least about 99% and up to 100% less than the binding to Aβ monomeric peptide 1-42.

In one embodiment of the invention the binding of the antibody according to the invention as described herein, particularly a monoclonal antibody including any functionally equivalent antibody or functional parts thereof, to Aβ monomeric peptides is determined by an ELISA-type assay, particularly by an ELISA assay using biotinylated Aβ monomeric peptides, but especially by an ELISA assay as described in Example 13 below.

In one embodiment the antibody according to the invention and as described herein, upon co-incubation with an Aβ peptide in a monomeric and/or an oligomeric form having at least 30, particularly at least 35, more particularly at least 38, even more particularly at least 40 amino acid residues, but especially with an Aβ142 peptide, particularly at a molar concentration ratio of antibody to $A\beta_{1-42}$ of up to 1:1000, but especially at a molar concentration ratio of between 1:10 and 1:100, inhibits the aggregation of the Aβ monomers and/or oligomers to high molecular polymeric fibrils.

In particular, the co-incubation of the antibody according to the invention with amyloid monomeric and/or oligomeric peptides is carried out for 24 hours to 60 hours, particularly for 30 hours to 50 hours, more particularly for 48 hours at a temperature of between 28° C. and 40° C., particularly of between 32° C. and 38° C., more particularly at 37° C.

In a specific embodiment of the invention, co-incubation with amyloid monomeric and/or oligomeric peptides is accomplished for 48 hours at a temperature of 37° C.

In particular, the antibody, particularly a monoclonal antibody according to the invention including any functionally equivalent antibody or functional parts thereof binds to Aβ1-42 monomeric peptide and polymeric soluble Aβ peptides comprising a plurality of Aβ1-42 monomeric peptides and Aβ fibrils or fibers incorporating a plurality of said polymeric peptides, but shows a substantially weaker binding to Aβ monomeric peptide 1-28 and/or essentially no binding to Aβ monomeric peptide 17-40. and, upon co-incubation with $A\beta_{1-42}$ monomeric and/or oligomeric peptide inhibits the aggregation of the Aβ monomers to high molecular polymeric fibrils.

In one embodiment, the antibody, particularly a monoclonal antibody according to the invention including any functionally equivalent antibody or functional parts thereof inhibits the aggregation of the Aβ monomers and/or oligomers to high molecular polymeric fibrils by at least 20%, by at least 30%, particularly by at least 40%, particularly by at least 50%, more particularly by at least 60%, even more particularly by at least 70%, but especially by at least 80%-90%, or more as compared to the respective amyloid peptide monomers incubated in buffer (control).

In one embodiment of the invention, an antibody is provided, particularly a monoclonal antibody according to the invention including any functionally equivalent antibody or functional parts thereof, which antibody binds to Aβ1-42 monomeric peptide and polymeric soluble Aβ peptides comprising a plurality of Aβ1-42 monomeric peptides and Aβ fibrils or fibers incorporating a plurality of said polymeric peptides, but shows a substantially weaker binding to Aβ monomeric peptide 1-28 and/or essentially no binding to Aβ monomeric peptide 17-40 and, upon co-incubation with $A\beta_{1-42}$ monomeric and/or oligomeric peptide for 24 hours at a temperature of 37° C. inhibits the aggregation of the Aβ monomers to high molecular polymeric fibrils by at least 20%, by at least 30%, particularly by at least 40%, particularly by at least 50%, more particularly by at least 60%, even more particularly by at least 70% at a molar concentration ratio of antibody to $A\beta_{1-42}$ of 1:100 and by at least 50%, more particularly by at least 60%, more particularly by at least 65%, even more particularly by at least 70% at a molar concentration ratio of antibody to $A\beta_{1-42}$ of 1:10 as determined by a thioflavin T (Th-T) fluorescent assay, particularly a thioflavin T (Th-T) fluorescent assay as described in Example 4.

Binding of the antibodies according to the invention and as described herein to amyloidogenic monomeric and/or oligomeric peptides but, particularly, to the amyloid form (1-42) leads to inhibition of the aggregation of monomeric and/or oligomeric amyloidogenic peptides to high molecular fibrils or filaments. Through the inhibition of the aggregation of amyloidogenic monomeric and/or oligomeric peptides the antibodies according to the present invention are capable of preventing or slowing down the formation of amyloid plaques, particularly the amyloid form (1-42), which is known to become insoluble by a change of secondary conformation and to be the major part of amyloid plaques in brains of diseased animals or humans.

The aggregation inhibition potential of the antibody according to the invention may be determined by any suitable method known in the art, for example, by density-gradient ultracentrifugation followed by a SDS-PAGE sedimentation analysis on a preformed gradient and/or by a thioflavin T (Th-T) fluorescent assay.

In one embodiment, the invention relates to an antibody, particularly a monoclonal antibody as described herein including any functionally equivalent antibody or functional parts thereof, which antibody, upon co-incubation, particularly at a molar concentration ratio of between 1:10 and 1:1000, more particularly at a ratio of between 1:10 and 1:100, with preformed high molecular polymeric amyloid fibrils or filaments formed by the aggregation of Aβ monomeric and/or oligomeric peptides having at least 30, particularly at least 35, more particularly at least 38, even more particularly at least 40 amino acid residues and, but especially of $A\beta_{1-42}$ monomeric and/or oligomeric peptides, is capable of disaggregating the preformed polymeric fibrils or filaments by at least 10%, by at least 20%, particularly by at least 30%, more particularly by at least 40%, even more particularly by at least 50%, but especially by at least 60%-70% or more.

In a specific embodiment of the invention, the aggregation inhibition and the disaggregation potential of the antibody, respectively, are determined by density-gradient ultracentrifugation followed by a SDS-PAGE sedimentation analysis on a preformed gradient.

In another specific embodiment of the invention, the aggregation inhibition and the disaggregation potential of the antibody, respectively, are determined by a thioflavin T (Th-T) fluorescent assay.

In another specific embodiment, the antibody according to the invention is co-incubated with preformed high molecular polymeric amyloid fibrils or filaments for 12 hours to 36 hours, particularly for 18 hours to 30 hours, more particularly for 24 hours at a temperature of between 28° C. and 40° C., particularly of between 32° C. and 38° C., more particularly at 37° C.

In particular, the co-incubation with preformed high molecular polymeric amyloid fibrils or filaments is performed for 24 hours at a temperature of 37° C.

In particular, the invention relates to an antibody, particularly the monoclonal antibody according to the invention including any functionally equivalent antibody or functional parts thereof, which antibody binds to Aβ1-42 monomeric peptide and polymeric soluble Aβ peptides comprising a plurality of Aβ1-42 monomeric peptides and Aβ fibrils or fibers incorporating a plurality of said polymeric peptides, but shows a substantially weaker binding to Aβ monomeric peptide 1-28 and/or essentially no binding to Aβ monomeric peptide 17-40. and, upon co-incubation with preformed high molecular polymeric amyloid fibrils or filaments formed by the aggregation of $A\beta_{1-42}$ monomeric and/or oligomeric peptides is capable of disaggregating the preformed polymeric fibrils or filaments, particularly by at least 10%, by at least 20%, particularly by at least 30%, more particularly by at least 40%, even more particularly by at least 50%, but especially by at least 60% or more.

In one embodiment of the invention, an antibody is provided, particularly a monoclonal antibody according to the invention including any functionally equivalent antibody or functional parts thereof, which antibody binds to Aβ1-42 monomeric peptide and polymeric soluble Aβ peptides comprising a plurality of Aβ1-42 monomeric peptides and Aβ fibrils or fibers incorporating a plurality of said polymeric peptides, but shows a substantially weaker binding to Aβ monomeric peptide 1-28 and/or essentially no binding to Aβ monomeric peptide 17-40 and, upon co-incubation with preformed high molecular polymeric amyloid fibrils or filaments formed by the aggregation of $A\beta_{1-42}$ monomeric and/or oligomeric peptide for 24 hours at a temperature of 37° C. results in a disaggregation of the preformed polymeric fibrils or filaments by at least 10%, by at least 20%, by at least 30%, particularly by at least 40%, particularly by at least 50%, more particularly by at least 60%, even more particularly by at least 70%, at a molar concentration ratio of antibody to $A\beta_{1-42}$ of 1:100 and by at least 40%, particularly by at least 50%, more particularly by at least 60%, even more particularly by at least 70% at a molar concentration ratio of antibody to $A\beta_{1-42}$ of 1:10 as determined by a thioflavin T (Th-T) fluorescent assay, particularly a thioflavin T (Th-T) fluorescent assay as described in Example 4 below.

Through both the inhibition of the aggregation of amyloid protein and through the disaggregation of amyloidogenic polymeric fibrils or filaments the antibodies according to the present invention are capable of preventing or slowing down the formation of amyloid plaques which leads to an alleviation of the symptoms associated with the disease and a delay or reversal of its progression.

Accordingly, it is a further embodiment of the invention to provide an antibody, particularly a monoclonal antibody, including any functionally equivalent antibody or functional parts thereof as described herein, which antibody is capable of decreasing the total amount of Aβ in the brain of a subject, particularly a mammal, but especially a human suffering from a disease or condition associated with to increased concentration of Aβ in the brain.

In another embodiment of the invention an antibody, particularly a monoclonal antibody, including any functionally equivalent antibody or functional parts thereof as described herein is provided, which antibody is capable of disrupting plaques thus decreasing the plaque load in the brain of a subject, particularly a mammal, but especially a human suffering from a disease or condition associated with an increased plaque load in the brain. An antibody according to the invention including any functionally equivalent antibody or functional parts thereof decreases the plaque load in the brain by at least 20%, particularly by at least 25%, more particularly by at least 30%, even more particularly more than 30%.

In still another embodiment of the invention an antibody, particularly a monoclonal antibody, including any functionally equivalent antibody or functional parts thereof as described herein is provided, which antibody is capable of solubilizing plaques associated with a reduction of the amount of plaques in the brain of a subject, particularly a mammal, but especially a human suffering from a disease or condition associated with an increased plaque load in the brain. An antibody according to the invention including any functionally equivalent antibody or functional parts thereof reduces the amount of plaques in the brain by at least 10%, particularly by at least 15%, more particularly by at least 20%.

It is to be understood that an antibody according to the invention can exhibit one, two or more of the specific properties described herein in various combinations.

For example, in one embodiment, the present invention provides antibodies, but especially monoclonal antibodies including any functionally equivalent antibody or functional parts thereof, which antibodies are bi-specific or bi-effective in that they exhibit both an aggregation inhibition property as well as a disaggregation property as defined herein, particularly paired with a high degree of conformational sensitivity.

In one embodiment, an antibody according to the invention and as described herein is bi-specific or bi-effective and, upon co-incubation with an Aβ monomeric and/or oligomeric peptide having at least 30, particularly at least 35, more particularly at least 38, even more particularly at least 40 amino acid residues, but especially with an $A\beta_{1-42}$ monomeric and/or oligomeric peptide, inhibits the aggregation of the Aβ monomers to high molecular polymeric fibrils and, in addition, upon co-incubation with preformed high molecular polymeric amyloid fibrils or filaments formed by the aggregation of Aβ monomeric and/or oligomeric peptides having at least 30, particularly at least 35, more particularly at least 38, even more particularly at least 40 amino acid residues and, but especially $A\beta_{1-42}$ monomeric and/or oligomeric peptides, is capable of disaggregating the preformed polymeric fibrils or filaments.

In particular, co-incubation with amyloid monomeric and/or oligomeric peptides and preformed high molecular polymeric amyloid fibrils or filaments, respectively, takes place at a molar concentration ratio of up to 1:1000, but especially at a molar concentration ratio of between 1:10 and 1:1000, particularly at a molar concentration ratio of 1:100.

Co-incubation of an antibody according to the invention with amyloid monomeric and/or oligomeric peptides is carried out for 24 hours to 60 hours, particularly for 30 hours to 50 hours, more particularly for 48 hours at a temperature of between 28° C. and 40° C., particularly of between 32° C. and 38° C., more particularly at 37° C., whereas the co-incubation with amyloid preformed high molecular polymeric amyloid fibrils or filaments is carried out for 12 hours to 36 hours, particularly for 18 hours to 30 hours, more particularly for 24 hours at a temperature of between 28° C. and 40° C., particularly of between 32° C. and 38° C., more particularly at 37° C.

In one embodiment, a bi-specific or bi-effective antibody according to the invention and as described herein, particularly a monoclonal antibody including any functionally equivalent antibody or functional parts thereof, is capable of disaggregating the preformed polymeric fibrils or filaments by at least 10%, by at least 20%, by at least 30%, particularly by at least 40%, particularly by at least 50%, more particularly by at least 60%, even more particularly by at least 70%.

In one embodiment, a bi-specific or bi-effective antibody according to the invention and as described herein, particularly a monoclonal antibody including any functionally equivalent antibody or functional parts thereof, is capable of inhibiting the aggregation of Aβ monomeric and/or oligomeric peptides having at least 30, particularly at least 35, more particularly at least 38, even more particularly at least 40 amino acid residues, but especially $A\beta_{1-42}$ monomeric and/or oligomeric peptides by at least 30%, particularly by at least 40%, particularly by at least 50%, more particularly by at least 60%, even more particularly by at least 70%, but especially by at least 80-90%, or more as compared to the respective amyloid peptide monomers incubated in buffer (control).

In one embodiment, the invention provides a bi-specific or bi-effective antibody as described herein, particularly a monoclonal antibody including any functionally equivalent antibody or functional parts thereof, which antibody exhibits high specificity to $A\beta_{1-42}$ monomeric peptides but shows essentially no or only minor cross-reactivity to an amyloid peptide monomer selected from the group consisting of $A\beta_{1-28}$, and $A\beta_{17-40}$ monomeric peptides.

In a specific embodiment, the invention relates to an antibody as described herein, particularly a monoclonal antibody including any functionally equivalent antibody or functional parts thereof, which antibody is up to 1000 fold, particularly 50 to 1000 fold, more particularly 80 to 100 fold, but especially 100 fold more sensitive to amyloid peptide $A\beta_{1-42}$ as compared to $A\beta_{1-28}$, and/or $A\beta_{17-40}$, and is capable of inhibiting, in vitro and in vivo, the aggregation of amyloidogenic monomeric and/or oligomeric peptides and/or of disaggregating preformed polymeric fibrils or filaments.

In one embodiment, the invention provides a bi-specific or bi-effective antibody as described herein, particularly a monoclonal antibody including any functionally equivalent antibody or functional parts thereof, which antibody binds to Aβ1-42 monomeric peptide and polymeric soluble Aβ peptides comprising a plurality of Aβ1-42 monomeric peptides and Aβ fibrils or fibers incorporating a plurality of said polymeric peptides, but shows a substantially weaker binding to Aβ monomeric peptide 1-28 and/or essentially no binding to Aβ monomeric peptide 17-40 and, upon co-incubation with $A\beta_{1-42}$ monomeric and/or oligomeric peptide for 24 hours at a temperature of 37° C. inhibits the aggregation of the Aβ monomers to high molecular polymeric fibrils by at least 30% at a molar concentration ratio of antibody to $A\beta_{1-42}$ of 1:100 and by at least 65% at a molar concentration ratio of antibody to $A\beta_{1-42}$ of 1:10 and, upon co-incubation with preformed high molecular polymeric amyloid fibrils or filaments formed by the aggregation of $A\beta_{1-42}$ monomeric and/or oligomeric peptide for 24 hours at a temperature of 37° C. results in a disaggregation of the preformed polymeric fibrils or filaments by at least 20%, at a molar concentration ratio of antibody to $A\beta_{1-42}$ of 1:100 and by at least 50% at a molar concentration ratio of antibody to $A\beta_{1-42}$ of 1:10 as determined by a thioflavin T (Th-T) fluorescent assay, particularly a thioflavin T (Th-T) fluorescent assay as described in Example 4 below.

In another specific embodiment, the invention relates to an antibody as described herein, particularly a monoclonal antibody including any functionally equivalent antibody or functional parts thereof, which antibody has a high binding sensitivity to amyloid peptide $A\beta_{1-42}$ and is capable of detecting $A\beta_{1-42}$ fibers in a concentration of up to 0.01 μg, but particularly in a concentration range of between 0.5 μg and 0.01 μg, more particularly between 0.1 μg and 0.01 μg, but especially in a concentration of 0.01 μg.

In one embodiment, the invention provides an antibody as described herein, particularly a monoclonal antibody including any functionally equivalent antibody or functional parts thereof, which antibody has been raised against a supramolecular antigenic construct comprising an antigenic peptide corresponding to the amino acid sequence of the β-amyloid peptide $A\beta_{22-35}$ and $A\beta_{29-40}$, respectively, modified with a hydrophilic moiety such as, for example, polyethylene glycol (PEG), wherein said hydrophilic moiety is covalently bound to each terminus through an amino acid such as, for example, lysine or any other suitable amino acid or amino acid analogue capable of serving as a linker molecule.

The antibody according to the invention and as described herein, particularly a monoclonal antibody including any functionally equivalent antibody or functional parts thereof recognizes and binds to a conformational epitope.

In one embodiment, the invention relates to a light chain variable region exhibiting an amino acid sequence that is 85%, 86%, 87%, 88%, 89%, 90%, 91%, 92%, 93%, 94%, 95%, 96%, 97%, 98% or 99% identical to the sequences given in SEQ ID NO: 7 and SEQ ID NO: 9, respectively, or a functional part thereof comprising at least one, particularly at least two, more particularly at least 3 of the light chain CDRs, but especially all CDRs embedded in their natural framework regions.

In one embodiment, the invention relates to a heavy chain variable region exhibiting an amino acid sequence that is 85%, 86%, 87%, 88%, 89%, 90%, 91%, 92%, 93%, 94%, 95%, 96%, 97%, 98% or 99% identical to the sequences given in SEQ ID NO: 8 and SEQ ID NO: 10, respectively, or a functional part thereof comprising at least one, particularly at least two, more particularly at least 3 of the heavy chain CDRs, but especially all CDRs embedded in their natural framework regions.

Further, the invention relates to an antibody, particularly a monoclonal antibody including any functionally equivalent antibody or functional parts thereof according to the present invention and as described herein wherein said antibody comprises a light chain variable domain exhibiting an amino acid sequence that is 85%, 86%, 87%, 88%, 89%, 90%, 91%, 92%, 93%, 94%, 95%, 96%, 97%, 98% or 99% identical to the sequences given in SEQ ID NO: 7 and SEQ ID NO: 9, respectively, or a functional part thereof comprising at least one, particularly at least two, more particularly at least 3 of the light chain CDRs, but especially all CDRs embedded in their natural framework regions.

Further, the invention relates to an antibody, particularly a monoclonal antibody including any functionally equivalent antibody or functional parts thereof according to the present invention and as described herein wherein said antibody comprises a heavy chain variable domain exhibiting an amino acid sequence that is 85%, 86%, 87%, 88%, 89%, 90%, 91%, 92%, 93%, 94%, 95%, 96%, 97%, 98% or 99% identical to the sequences given in SEQ ID NO: 8 and SEQ ID NO: 10, respectively, or a functional part thereof comprising at least one, particularly at least two, more particularly at least 3 of the heavy chain CDRs, but especially all CDRs embedded in their natural framework regions.

In one embodiment, the invention relates to an antibody, particularly a monoclonal antibody including any functionally equivalent antibody or functional parts thereof according to the present invention and as described herein, wherein said antibody comprises a light chain and a heavy chain variable domain exhibiting an amino acid sequence that is 85%, 86%, 87%, 88%, 89%, 90%, 91%, 92%, 93%, 94%, 95%, 96%, 97%, 98% or 99% identical to the sequences given in SEQ ID NO: 7, SEQ ID NO: 9, SEQ ID NO: 8 and SEQ ID NO: 10, or a functional part thereof comprising part or all the heavy and the light chain CDRs.

The invention further relates to a monoclonal antibody including any functionally equivalent antibody or functional parts thereof which antibody comprises the polypeptide sequence as given in SEQ ID NOs: 7 and SEQ ID NOs:9 and/or in SEQ ID NO: 8 and SEQ ID NOs:10. The invention further relates to the monoclonal antibody ACI-11-Ab-9 having the polypeptide sequences SEQ ID NO: 7-8 and ACI-12-Ab-11 having the polypeptide sequences SEQ ID NOs: 9-10.

Also comprised by the present invention is an antibody the sequence of which has been altered by introducing at least one, particularly at least two, more particularly at least 3 or more conservative substitutions into the sequences of SEQ ID NOs: 7-8 and SEQ ID NOs: 9-10, respectively, such that the antibody essentially maintains its full functionality.

In one embodiment the invention relates to a peptide fragment comprising the light chain CDR1 as given in SEQ ID NO: 11 and/or the light chain CDR2 as given in SEQ ID NO:12 and/or the light chain CDR3 as given in SEQ ID NO:13.

In one embodiment the invention relates to a peptide fragment comprising the heavy chain CDR1 as given in SEQ ID NO:14 and/or the heavy chain CDR2 as given in SEQ ID NO:15 and/or the heavy chain CDR3 as given in SEQ ID NO:16.

In one embodiment the invention relates to the light chain CDR1 as given in SEQ ID NO:1.

In one embodiment the invention relates to the light chain CDR2 as given in SEQ ID NO:12.

In one embodiment the invention relates to the light chain CDR3 as given in SEQ ID NO:13.

In one embodiment the invention relates to the heavy chain CDR1 as given in SEQ ID NO:14.

In one embodiment the invention relates to the heavy chain CDR2 as given in SEQ ID NO:15.

In one embodiment the invention relates to the heavy chain CDR3 as given in SEQ ID NO:16.

In one embodiment, the invention relates to a polynucleotide comprising a nucleotide sequence encoding a light chain variable region exhibiting an amino acid sequence that is 85%, 86%, 87%, 88%, 89%, 90%, 91%, 92%, 93%, 94%, 95%, 96%, 97%, 98% or 99% identical to the sequences given in SEQ ID NO: 7 and SEQ ID NO: 9, respectively, or a functional part thereof comprising at least one, particularly at least two, more particularly at least 3 of the light chain CDRs as depicted in SEQ ID NOs: 11-13, but especially all CDRs embedded in their natural framework regions.

In one embodiment, the invention relates to a polynucleotide comprising a nucleotide sequence encoding a heavy chain variable region exhibiting an amino acid sequence that is 85%, 86%, 87%, 88%, 89%, 90%, 91%, 92%, 93%, 94%, 95%, 96%, 97%, 98% or 99% identical to the sequences given in SEQ ID NO: 8 and SEQ ID NO: 10, respectively, or a functional part thereof comprising at least one, particularly at least two, more particularly at least 3 of the heavy chain CDRs as depicted in SEQ ID NOs: 14-16, but especially all CDRs embedded in their natural framework regions.

In one embodiment, the invention relates to a polynucleotide comprising a nucleotide sequence encoding an antibody, particularly a monoclonal antibody including any functionally equivalent antibody or functional parts thereof according to the present invention and as described herein wherein said antibody comprises a light chain variable domain exhibiting an amino acid sequence that is 85%, 86%, 87%, 88%, 89%, 90%, 91%, 92%, 93%, 94%, 95%, 96%, 97%, 98% or 99% identical to the sequences given in SEQ ID NO: 7 and SEQ ID NO: 9, respectively, or a functional part thereof comprising at least one, particularly at least two, more particularly at least 3 of the light chain CDRs as depicted in SEQ ID NOs: 11-13, but especially all CDRs embedded in their natural framework regions.

In one embodiment, the invention relates to a polynucleotide comprising a nucleotide sequence encoding an antibody, particularly a monoclonal antibody including any functionally equivalent antibody or functional parts thereof according to the present invention and as described herein wherein said antibody comprises a heavy chain variable domain exhibiting an amino acid sequence that is 85%, 86%, 87%, 88%, 89%, 90%, 91%, 92%, 93%, 94%, 95%, 96%, 97%, 98% or 99% identical to the sequences given in SEQ ID NO: 8 and SEQ ID NO: 10, respectively, or a functional part thereof comprising at least one, particularly at least two, more particularly at least 3 of the heavy chain CDRs as depicted in SEQ ID NOs: 14-16, but especially all CDRs embedded in their natural framework regions.

In one embodiment, the invention relates to a polynucleotide comprising a nucleotide sequence encoding an antibody, particularly a monoclonal antibody including any functionally equivalent antibody or functional parts thereof according to the present invention and as described herein wherein said antibody comprises a light chain and a heavy chain variable domain exhibiting an amino acid sequence that is 85%, 86%, 87%, 88%, 89%, 90%, 91%, 92%, 93%, 94%, 95%, 96%, 97%, 98% or 99% identical to the sequences given SEQ ID NO: 7 and SEQ ID NO: 9 and in SEQ ID NO: 8 and SEQ ID NO: 10, respectively, or a functional part thereof comprising the light chain and the heavy chain CDRs as depicted in SEQ ID NOs: 11-16.

In another embodiment of the invention, a polynucleotide is provided comprising a nucleotide sequence encoding the antibody according to the invention as described herein, but particularly a nucleotide sequence encoding a monoclonal antibody having the polypeptide sequences in SEQ ID NOs: 7-8 or a monoclonal antibody having the polypeptide sequences SEQ ID NOs: 9-10. In particular, the polynucleotides encoding SEQ ID NOs: 7-8 and SEQ ID NOs:9-10 are SEQ ID NOs: 17-18 and SEQ ID NO: 19-20, respectively.

In another embodiment, a polynucleotide is provided which hybridizes under stringent conditions to a nucleotide sequence encoding the monoclonal antibody having the polypeptide sequences SEQ ID NOs: 7-8 or a monoclonal antibody having the polypeptide sequences SEQ ID NOs: 9-10. In particular a polynucleotide is provided which hybridizes under stringent conditions to nucleotides sequences SEQ ID NOs: 17-18 or SEQ ID NO: 19-20.

In a specific embodiment, the invention relates to a monoclonal antibody including any functionally equivalent antibody or functional parts thereof which antibody has the characteristic properties of an antibody produced by hybridoma cell line FG1F9E4, deposited on May 25, 2007 as DSM ACC2845.

In particular, the invention relates to a monoclonal antibody including any functionally equivalent antibody or functional parts thereof produced by hybridoma cell line FG1F9E4, deposited on May 25, 2007 as DSM ACC2845.

In a specific embodiment, the invention relates to a monoclonal antibody including any functionally equivalent antibody or functional parts thereof which antibody has the characteristic properties of an antibody produced by hybridoma cell line FK2A6A6, deposited on May 25, 2007 as DSM ACC2846.

In particular, the invention relates to a monoclonal antibody including any functionally equivalent antibody or functional parts thereof produced by hybridoma cell line FK2A6A6, deposited on May 25, 2007 as DSM ACC2846.

In particular, the invention also relates to an Aβ epitope which bind to a monoclonal antibody including any functionally equivalent antibody or functional parts thereof, which antibody has been raised against a supramolecular antigenic construct comprising an antigenic peptide corresponding to the amino acid sequence of the β-amyloid peptide, $A\beta_{22-35}$ and $A\beta_{29-40}$, respectively, modified with a hydrophilic moiety such as, for example, polyethylene glycol (PEG), wherein said hydrophilic moiety is covalently bound to each terminus through an amino acid such as, for example, lysine or any other suitable amino acid or amino acid analogue capable of serving as a linker molecule. The invention further relates to an Aβ epitope which binds to the monoclonal antibody ACI-11-Ab-9. The invention further relates to an Aβ epitope which binds to the monoclonal antibody ACI-12-Ab-11.

In one aspect, an antibody according to the invention as described herein, particularly a monoclonal antibody including any functionally equivalent antibody or functional parts thereof is capable of decreasing the total amount of soluble Aβ in the brain of a subject, particularly a mammal, but especially a human suffering from a disease or condition associated with increased concentrations of soluble Aβ in the brain.

In another aspect, an antibody according to the invention and as described herein is capable of disrupting plaques thus decreasing the plaque load in the brain of a subject, particularly a mammal, but especially a human suffering from a disease or condition associated with an increased plaque load in the brain.

In another aspect, an antibody according to the invention and as described herein is capable of solubilizing plaques leading to a reduction of the amount of plaques in the brain of a subject, particularly a mammal, but especially a human suffering from a disease or condition associated with an increased plaque load in the brain.

It is another object of the present invention to provide methods and compositions comprising an antibody according to the invention and as described herein for the prevention and/or therapeutic treatment and/or alleviation of the effects of diseases and disorders in a subject, which are caused by or associated with amyloid or amyloid-like proteins including but not limited to, amyloidosis (a group of diseases and disorders associated with amyloid plaque formation including secondary amyloidosis and age-related amyloidosis such as diseases including, but not limited to, neurological disorders such as Alzheimer's Disease (AD), diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases and conditions which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; and senile cardiac amyloidosis); endocrine tumors, and macular degeneration, for example, by passively immunizing a subject, including a human or animal, with an antibody according to the invention and as described herein. In a further aspect of the invention the monoclonal antibodies of these methods are ACI-1-Ab-9 having the polypeptide sequences SEQ ID NOs: 7-8 or ACI-12-Ab-11 having the polypeptide sequences SEQ ID NO: 9-10, respectively, or a functional part thereof as described herein.

The invention further relates to a therapeutic composition comprising an antibody as described herein, particularly a monoclonal antibody including any functionally equivalent antibody or functional parts thereof in a therapeutically effective amount.

In one embodiment, the pharmaceutical composition further comprises a pharmaceutically acceptable carrier, particularly in a therapeutically effective amount.

In one embodiment, the invention provides a composition as described herein for use in the treatment of diseases and disorders in a subject, which are caused by or associated with amyloid or amyloid-like proteins including, but not limited to, amyloidosis, tumors, and macular degeneration. In a further aspect of such embodiments the monoclonal antibodies used are selected from monoclonal antibody protein ACI-11-Ab-9 having the polypeptide sequences SEQ ID NOs: 7-8 and monoclonal antibody protein ACI-12-Ab-11 having the polypeptide sequences SEQ ID NO: 9-10, or a functional part thereof.

An antibody, according to the invention, particularly a monoclonal antibody including any functionally equivalent antibody or functional parts thereof may be administered in combination with other biologically active substances or other treatment procedures for the treatment of diseases. The other biologically active substances may be part of the same composition already comprising an antibody according to the invention, in the form of a mixture, wherein the antibody and the other biologically active substance are intermixed in or with the same pharmaceutically acceptable solvent and/or carrier or the antibody and the other biologically active substance may be provided separately as part of a separate composition, which may be offered separately or together in the form of a kit of parts.

The antibody, particularly a monoclonal antibody according to the invention including any functionally equivalent antibody or functional parts thereof may be administered to a subject in need thereof at the same time with the other biologically active substance or substances, intermittently or sequentially. For example, a monoclonal antibody according to the invention including any functionally equivalent antibody or functional parts thereof, may be administered to a subject in need thereof simultaneously with a first additional biologically active substance or sequentially after or before administration of the antibody. If an application scheme is chosen where more than one additional biologically active substance are administered together with the at least one antibody according to the invention, the compounds or substances may partially be administered simultaneously, partially sequentially in various combinations.

In one embodiment, the invention relates to a therapeutic composition comprising an antibody as described herein, particularly a monoclonal antibody including any functionally equivalent antibody or functional parts thereof in a therapeutically effective amount and a further biologically active substance or compound, particularly a compound used in the medication of diseases and disorders in a subject, which are caused by or associated with amyloid or amyloid-like proteins including, but not limited to, amyloidosis, endocrine tumors, and macular degeneration, and/or a pharmaceutically acceptable carrier and/or a diluent and/or an excipient.

In one embodiment, a therapeutic composition is provided according to the invention and as described herein comprising an antibody as described herein, particularly a monoclonal antibody including any functionally equivalent antibody or functional parts thereof, and further comprising at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, β- and γ-secretase inhibitors, tau proteins, neurotransmitter, β-sheet breakers, anti-inflammatory molecules, or cholinesterase inhibitors (ChEIs) such as tacrine, rivastigmine, donepezil, and/or galantamine and other drugs and nutritive supplements, and, optionally, a pharmaceutically acceptable carrier and/or a diluent and/or an excipient.

In a specific embodiment, the invention provides a therapeutic composition comprising an antibody as described herein, particularly a monoclonal antibody, including any functionally equivalent antibody or functional parts thereof, further comprising at least one cholinesterase inhibitor (ChEIs).

In another specific embodiment, the invention provides a therapeutic composition comprising an antibody as described herein, particularly a monoclonal antibody, including any functionally equivalent antibody or functional parts thereof, further comprising at least one additional compound selected from the group consisting of tacrine, rivastigmine, donepezil, galantamine, niacin and memantine.

In still another embodiment of the invention therapeutic compositions are provided comprising an antibody as described herein, particularly a monoclonal antibody, including any functionally equivalent antibody or functional parts thereof, further comprising at least one "atypical antipsychotic" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, and, optionally, further comprising a pharmaceutically acceptable carrier and/or a diluent and/or an excipient.

Other compounds that can be suitably used in mixtures in combination with an antibody according to the present invention, including any functionally equivalent antibody or functional parts thereof, are, for example, described in WO 2004/058258 (see especially pages 16 and 17) including therapeutic drug targets (page 36-39), alkanesulfonic acids and alkanolsulfuric acids (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptor (PPAR) agonists (pages 63-67), cholesterol-lowering agents (pages 68-75); amyloid inhibitors (pages 75-77), amyloid formation inhibitors (pages 77-78), metal chelators (pages 78-79), anti-psychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference.

In particular, the therapeutic composition according to the invention comprises the monoclonal antibody and/or the biologically active substance, including any functionally equivalent antibody or functional parts thereof, in a therapeutically effective amount.

In one embodiment, the invention relates to a method of producing an antibody as described herein, particularly a monoclonal antibody including any functionally equivalent antibody or functional parts thereof, which method comprises raising in a suitable host organism an antibody against a supramolecular antigenic construct comprising an antigenic peptide corresponding to the amino acid sequence of the β-amyloid peptide or a fragment thereof, particularly of β-amyloid peptide $A\beta_{22-35}$ and $A\beta_{29-40}$, respectively, modified with hydrophilic moieties, particularly a polyethylene glycol (PEG) moiety, wherein said hydrophilic moiety is covalently bound to each terminus through an amino acid such as, for example, lysine or any other suitable amino acid or amino acid analogue capable of serving as a linker molecule; and isolating the antibody.

In one embodiment, the invention relates to the use of an antibody according to the invention and as described herein, particularly a monoclonal antibody including any functionally equivalent antibody or functional parts thereof and/or of a pharmaceutical composition according to the invention and as described herein, or of a therapeutic composition according to the invention and as described herein for the preparation of a medicament for treating or alleviating the effects of diseases and disorders in a subject, which are caused by or associated with amyloid or amyloid-like proteins including, but not limited to, amyloidosis, endocrine tumors, and macular degeneration.

In one embodiment, the invention relates to a method for the preparation of a pharmaceutical or therapeutic composition according to the invention and as described herein using an antibody according to the invention and as described herein, particularly a monoclonal antibody including any functionally equivalent antibody or functional parts thereof for use in treating or alleviating the effects of diseases and disorders in a subject, which are caused by or associated with amyloid or amyloid-like proteins including, but not limited to, amyloidosis, endocrine tumors, and macular degeneration.

In one embodiment, the invention provides a method for the preparation of a medicament using an antibody, particularly a monoclonal antibody including any functionally equivalent antibody or functional parts thereof, a pharmaceutical or therapeutic composition according to the invention and as described herein, for preventing, treating or alleviating the effects of diseases and disorders in a subject, which are caused by or associated with amyloid or amyloid-like proteins including, but not limited to, amyloidosis, endocrine tumors, and macular degeneration.

In a specific embodiment, the invention relates to a method for the preparation of a pharmaceutical composition using particularly an antibody according to the invention or as described herein, particularly a monoclonal antibody including any functionally equivalent antibody or functional parts thereof, comprising formulating said antibody in a pharmaceutically acceptable form, particularly such that the antibody is comprised in the composition in a therapeutically effective amount.

In one aspect of the invention, a method is provided for reducing the plaque load in the brain of a subject, particularly a mammal, but especially a human suffering from a disease or condition associated with an increased plaque load in the brain comprising administering to a subject in need thereof, particularly a mammal, more particularly a human in need of such a treatment, a therapeutically effective amount of an antibody, particularly a monoclonal antibody including any functionally equivalent antibody or functional parts thereof, or a composition or a mixture according to the invention and as described herein. In a further aspect of the invention the monoclonal antibodies used in such methods are ACI-11-Ab-9 having the polypeptide sequences SEQ ID NOs: 7-8 or ACI-12-Ab-11 having the polypeptide sequences SEQ ID NO: 9-10, or a functional part thereof as described herein. In particular, the monoclonal antibody is produced by the hybridoma FG1F9E4, deposited on May 25, 2007 as DSM ACC2845, or the hybridoma FK2A6A6, deposited on May 25, 2007 as DSM ACC2846. In particular, the plaque load is reduced by at least 20%, particularly by at least 25%, more particularly by at least 30%, even more particularly by more than 30%.

In another aspect of the invention, a method is provided for reducing the amount of plaques in the brain of a subject, particularly a mammal, but especially a human suffering from a disease or condition associated with an increased plaque load in the brain comprising administering to a subject in need thereof, particularly a mammal, more particularly a human in need of such a treatment, a therapeutically effective amount of an antibody, particularly a monoclonal antibody including any functionally equivalent antibody or functional parts thereof, or a composition or a mixture according to the invention and as described herein. In a further aspect of the invention the monoclonal antibodies used in such methods are ACI-11-Ab-9 having the polypeptide sequences SEQ ID NOs: 7-8 or ACI-12-Ab-11 having the polypeptide sequences SEQ ID NO: 9-10, or a functional part thereof as described herein. In particular, the monoclonal antibody is produced by the hybridoma FG1F9E4, deposited on May 25, 2007 as DSM ACC2845, or the hybridoma FK2A6A6, deposited on May 25, 2007 as DSM ACC2846. In particular, the amount of plaques in the brain is reduced by at least 10%, particularly by at least 15%, more particularly by more than 15%.

In still another aspect of the invention, a method is provided for decreasing the total amount of soluble Aβ in the brain of a subject, particularly a mammal, but especially a human suffering from a disease or condition associated with increased concentrations of soluble Aβ in the brain comprising administering to a subject in need thereof, particularly a mammal, more particularly a human in need of such a treatment, a therapeutically effective amount of an antibody, particularly a monoclonal antibody including any functionally equivalent antibody or functional parts thereof, or a composition or a mixture according to the invention and as described herein. In a further aspect of the invention the monoclonal antibodies used in such methods are ACI-1-Ab-9 having the polypeptide sequences SEQ ID NOs: 7-8 or ACI-12-Ab-11 having the polypeptide sequences SEQ ID NO: 9-10, or a functional part thereof as described herein. In particular, the monoclonal antibody is produced by the hybridoma FG1F9E4, deposited on May 25, 2007 as DSM ACC2845, or the hybridoma FK2A6A6, deposited on May 25, 2007 as DSM ACC2846.

In still another aspect of the invention, a method is provided for preventing, treating or alleviating the effects of diseases and disorders caused by or associated with amyloid or amyloid-like proteins including, but not limited to, amyloidosis, endocrine tumors, and macular degeneration, in a subject, particularly a mammal or a human affected by such a disorder, by administering a therapeutically effective amount of an antibody, particularly a monoclonal antibody, including any functionally equivalent antibody or functional parts thereof, or a composition or a mixture according to the invention and as described herein to a subject, particularly a mammal, more particularly a human in need of such a treatment.

In still another aspect of the invention, a method is provided for retaining or increasing cognitive memory capacity in a subject, particularly a mammal exhibiting an amyloid-associated disease or condition comprising administering to a subject, particularly a mammal, more particularly a human in need of such a treatment, a therapeutically effective amount of an antibody, particularly a monoclonal antibody including any functionally equivalent antibody or functional parts thereof, or a composition or a mixture according to the invention or as described herein.

In one embodiment, the invention relates to a hybridoma cell line characterized in that it produces a monoclonal antibody according to the invention or as described herein.

In particular, the invention relates to a hybridoma cell line characterized in that it produces a monoclonal antibody, which antibody has the characteristic properties of an antibody produced by hybridoma FG1F9E4, deposited on May 25, 2007 and given the DSMZ deposit accession number DSM ACC2845.

In a specific embodiment of the invention, hybridoma cell line FG1F9E4, deposited on May 25, 2007 and given the DSMZ deposit accession number DSM ACC2845 is provided.

In particular, the invention relates to a hybridoma cell line characterized in that it produces a monoclonal antibody which antibody has the characteristic properties of an antibody produced by hybridoma FK2A6A6, deposited on May 25, 2007 and given the DSMZ deposit accession number DSM ACC2846.

In a specific embodiment of the invention, hybridoma cell line FK2A6A6, deposited on May 25, 2007 and given the DSMZ deposit accession number DSM ACC2846 is provided.

In one embodiment, the invention relates to a method of diagnosis of an amyloid-associated disease or condition in a patient comprising detecting the immunospecific binding of an antibody as described herein, particularly a monoclonal antibody including any functionally equivalent antibody or functional parts thereof, to an epitope of the amyloid protein in a sample or in situ which includes the steps of (a) bringing the sample or a specific body part or body area suspected to contain the amyloid protein into contact with an antibody according to the invention, which antibody binds an conformational epitope of the amyloid protein;

(b) allowing the antibody to bind to the amyloid protein to form an immunological complex;

(c) detecting the formation of the immunological complex, particularly such that presence or absence of the immunological complex correlates with presence or absence of amyloid protein; and (d) correlating the presence or absence of the immunological complex with the presence or absence of amyloid protein in the sample or specific body part or area.

In a specific embodiment the composition of step (a) comprises a combination of antibodies for the treatment of said patient In one embodiment, a method of determining the extent of amyloidogenic plaque burden in a tissue of a subject is provided comprising obtaining a sample representative of the tissue under investigation;

testing said sample for the presence of amyloid plaque with an antibody according to the invention and as described herein, particularly a monoclonal antibody including any functionally equivalent antibody or functional parts thereof;

determining the amount of antibody bound to the sample, particularly such that presence or absence of the immunological complex correlates with presence or absence of amyloid plaque; and calculating the plaque burden in the tissue.

In one embodiment, a method for diagnosing a predisposition to an amyloid-associated disease or condition in a patient is provided comprising detecting the specific binding of an antibody as described herein, particularly a monoclonal antibody including any functionally equivalent antibody or functional parts thereof, to an epitope of the amyloid protein in a sample or in situ which includes the steps of (a) bringing the sample or a specific body part or body area suspected to contain the amyloid protein into contact with the antibody, wherein the antibody binds an conformational epitope of the amyloid protein;

(b) allowing the antibody to bind to any amyloid protein in the sample to form an immunological complex;

(c) detecting the formation of the immunological complex; and (d) correlating the presence or absence of the immunological complex with the presence or absence of amyloid protein in the sample or specific body part or area, (e) comparing the amount of said immunological complex to a normal control value, wherein an increase in the amount of said complex compared to a normal control value indicates that said patient is suffering from or is at risk of developing an amyloid-associated disease or condition.

In one embodiment, a method is provided for monitoring minimal residual disease in a patient following treatment with an antibody or a composition according to the invention, wherein said method comprises:

(a) bringing the sample or a specific body part or body area suspected to contain the amyloid protein into contact with an antibody according to the invention and as described herein, particularly a monoclonal antibody including any functionally equivalent antibody or functional parts thereof, which antibody binds an conformational epitope of the amyloid protein;

(b) allowing the antibody to bind to the amyloid protein to form an immunological complex;

(c) detecting the formation of the immunological complex; and (d) correlating the presence or absence of the immunological complex with the presence or absence of amyloid protein in the sample or specific body part or area, (e) comparing the amount of said immunological complex to a normal control value, wherein an increase in the amount of said complex compared to a normal control value indicates that said patient still suffers from a minimal residual disease.

In a specific embodiment the composition of step (a) comprises a combination of antibodies for the treatment of said patient.

In one embodiment, a method is provided for predicting responsiveness of a patient being treated with an antibody or a composition according to the invention comprising (a) bringing the sample or a specific body part or body area suspected to contain the amyloid protein into contact with an antibody according to the invention and as described herein, particularly a monoclonal antibody including any functionally equivalent antibody or functional parts thereof, which antibody binds an conformational epitope of the amyloid protein;

(b) allowing the antibody to bind to the amyloid protein to form an immunological complex;

(c) detecting the formation of the immunological complex; and (d) correlating the presence or absence of the immunological complex with the presence or absence of amyloid protein in the sample or specific body part or area, and (e) comparing the amount of said immunological complex before and after onset of the treatment, wherein an decrease in the amount of said immunological complex indicates that said patient has a high potential of being responsive to the treatment.

In a specific embodiment the composition of step (a) comprises a combination of antibodies for the treatment of said patient In one embodiment, the invention relates to a test kit for the detection and diagnosis of amyloid-associated diseases and conditions comprising an antibody according to the invention and as described herein, particularly a monoclonal antibody including any functionally equivalent antibody or functional parts thereof and instructions for using the antibody for the purpose of binding to amyloid protein to form an immunological complex and detecting the formation of the immunological complex such that presence or absence of the immunological complex correlates with presence or absence of amyloid protein.

These and other objects, features and advantages of the present invention will become apparent after a review of the following detailed description of the disclosed embodiment and the appended claims.

BRIEF DESCRIPTION OF FIGURES AND SEQUENCES

FIG. 1 shows the results of an epitope mapping study of the murine monoclonal antibody ACI-11-Ab-9 performed by ELISA using a peptide library of overlapping peptides covering the complete amino acid sequence of Aβ1-42. Binding to the complete Aβ1-42 was used as positive control. All other peptides were 8-10 aa long. The peptide number corresponds to the aa in the Aβ1-42 sequence on which the peptide starts. Results are expressed as O.D.

FIG. 2 shows the results of an epitope mapping study of the murine monoclonal antibody ACI-11-Ab-9 performed by ELISA using longer peptide covering Aβ1-28, 17-40, 1-40, 1-42A (Anaspec), or 1-42B (Bachem). Results are expressed as O.D., after subtraction of the background. Results show the mean±1 standard error of 2 independent experiments.

FIG. 3 shows the results of an epitope mapping study of the murine monoclonal antibody ACI-12-Ab-11 performed by ELISA using a peptide library of overlapping peptides covering the complete amino acid sequence of Aβ1-42. Binding to the complete Aβ 1-42 was used as positive control. All other peptides were 8-10 aa long. The peptide number corresponds to the aa in the Aβ 1-42 sequence on which the peptide starts. Results are expressed as O.D.

FIG. 4 shows the results of an epitope mapping study of the murine monoclonal antibody ACI-11-Ab-9 performed by ELISA using longer peptide covering. Aβ 1-28, 17-40, 1-40, 1-42A (Anaspec), or 1-42B (Bachem). Results are expressed as O.D., after subtraction of the background. Results show the mean±1 standard error of 2 independent experiments.

Figure 10:
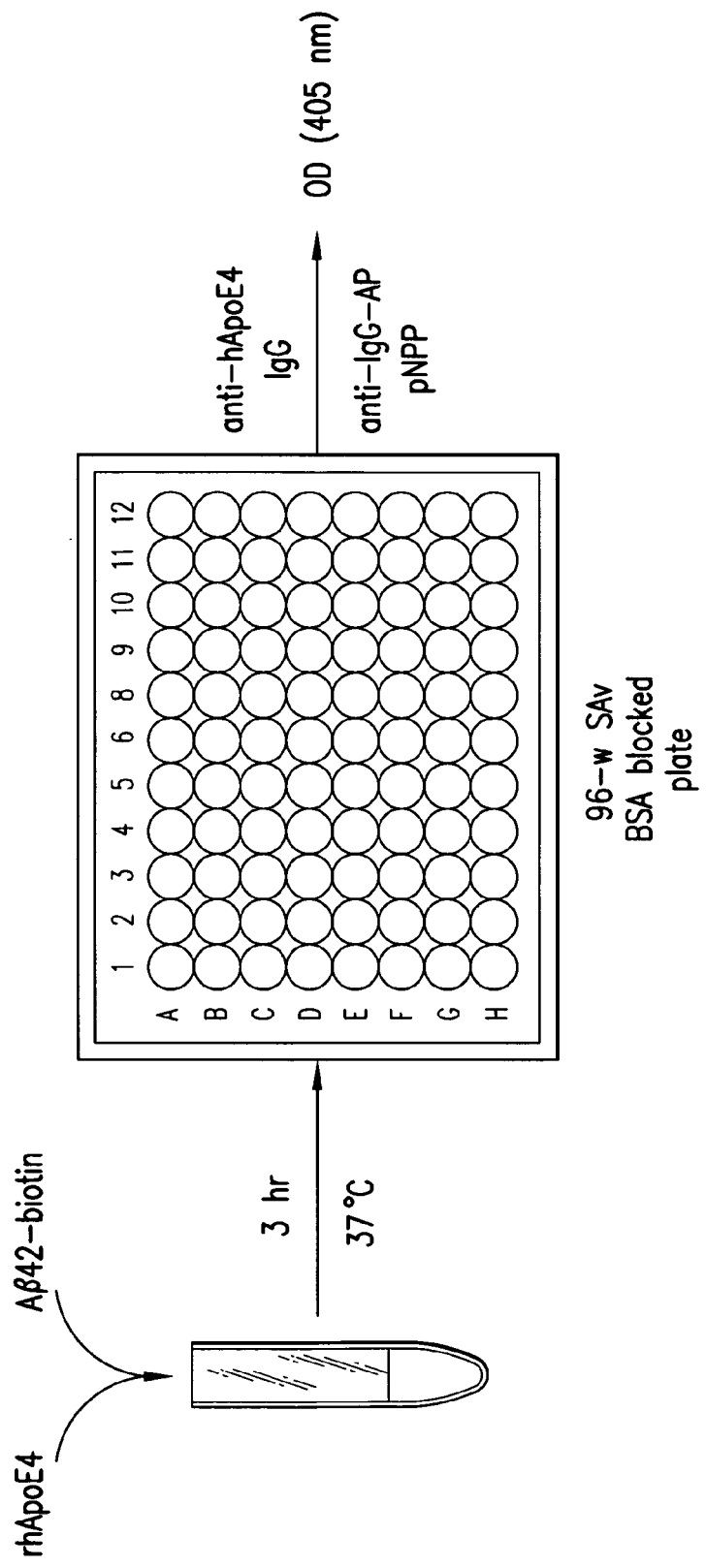

FIG. 10 schematically depicts steps in the ELISA assay that can be used to analyze the binding of rhApoE4 to $A\beta_{42}$-biotin.

Figure 11:
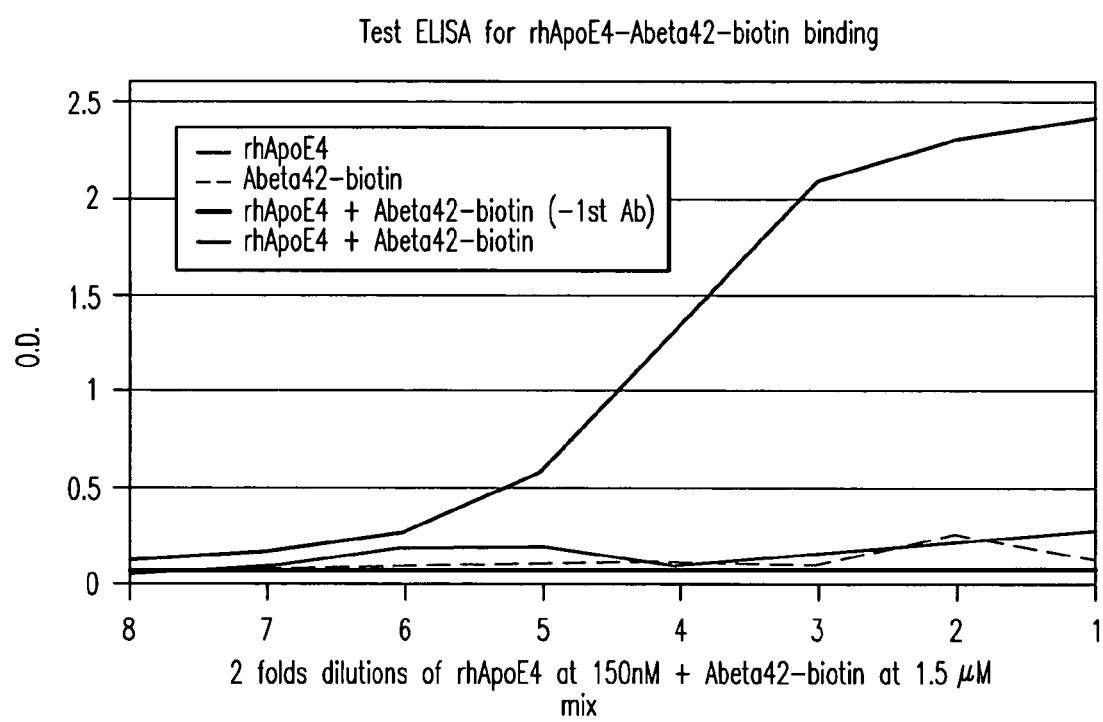

FIG. 11 represents the results obtained from development of an ELISA assay for rhApoE4 to $A\beta_{42}$-biotin binding. To optimize the concentrations of rhApoE4 and $A\beta_{42}$-biotin, dilutions of rhApoE4 are tested with a constant concentration of $A\beta_{42}$-biotin.

Figure 12:
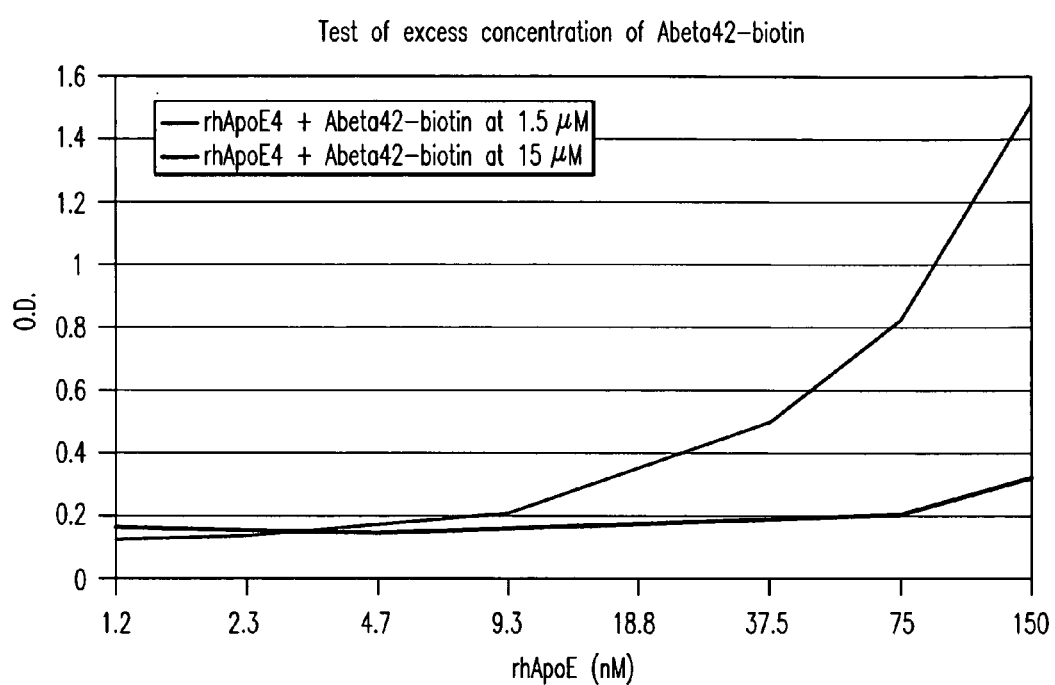

FIG. 12 depicts the effect of excess of $A\beta_{42}$-biotin on the binding of $A\beta_{42}$-biotin complexed to rhApoE4 in the described ELISA assay.

Figure 13:
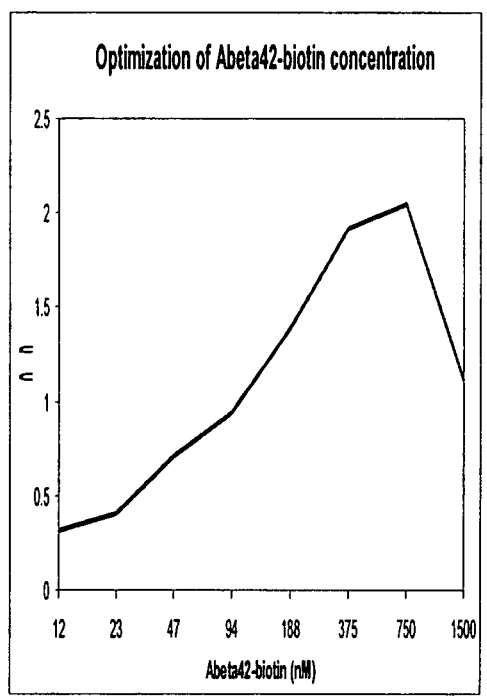

FIG. 13 depicts a sample determination of the optimal concentration of $A\beta_{42}$-biotin for the described ELISA assay.

Table 1 sets forth the antibodies and antigenic constructs used for raising certain antibodies described herein.

Table 2. Binding of Aβ peptides to ACI-11-Ab-9 and ACI-12-Ab-11. Results are expressed as O.D. after background subtraction.

Table 3. Binding of ACI-11-Ab-9 and ACI-12-Ab-11 to 33 overlapping peptides of Aβ 1-42 as analyzed by ELISA. Binding to the complete Aβ 1-42 was used as positive control. All other peptides were 8-10 aa long. The peptide number corresponds to the aa in the Aβ 1-42 sequence on which the peptide starts. Results are expressed as O.D.

Table 4 Binding of the ACI-12-Ab-11 (clone FK2A6A6) antibody to monomers and oligomers of the Aβ1-42 peptide. Results are expressed as O.D. values.

Table 5 Binding of the 6E10 control antibody antibody to monomers and oligomers of the Aβ1-42 peptide. Results are expressed as O.D. values.

SEQ ID NO: 1: Antigenic peptide $A\beta_{22-35}$
SEQ ID NO: 2: Antigenic peptide $A\beta_{29-40}$
SEQ ID NO: 3: Aβ-peptide fragment $A\beta_{1-28}$
SEQ ID NO: 4: Aβ-peptide fragment $A\beta_{17-40}$
SEQ ID NO: 5 Aβ-peptide fragment $A\beta_{1-40}$
SEQ ID NO 6: Aβ-peptide fragment $A\beta_{1-42}$
SEQ ID NO: 7 Amino Acid sequence of the light chain variable domain sequence of ACI-11-Ab-9.
SEQ ID NO: 8 Amino Acid sequence of the heavy chain variable domain sequence of ACI-11-Ab-9.
SEQ ID NO: 9 Amino Acid sequence of the light chain variable domain sequence of ACI-12-Ab-11.
SEQ ID NO: 10 Amino Acid sequence of the heavy chain variable domain sequence of ACI-12-Ab-11.
SEQ ID NO: 11 Amino Acid sequence of the light chain CDR1
SEQ ID NO: 12 Amino Acid sequence of the light chain CDR2
SEQ ID NO: 13 Amino Acid sequence of the light chain CDR3
SEQ ID NO: 14 Amino Acid sequence of the heavy chain CDR1
SEQ ID NO: 15 Amino Acid sequence of the heavy chain CDR2
SEQ ID NO: 16 Amino Acid sequence of the heavy chain CDR3
SEQ ID NO: 17 Polynucleotide sequence encoding the light chain variable domain sequence of ACI-11-Ab-9.
SEQ ID NO: 18 Polynucleotide sequence encoding the heavy chain variable domain sequence of ACI-11-Ab-9.
SEQ ID NO: 19 Polynucleotide sequence encoding the light chain variable domain sequence of ACI-12-Ab-11.
SEQ ID NO: 20 Polynucleotide sequence encoding the light chain variable domain sequence of ACI-12-Ab-11.

DETAILED DESCRIPTION OF THE INVENTION

Definitions

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

The terms "detecting" or "detected" as used herein mean using known techniques for detection of biologic molecules such as immunochemical or histological methods and refer to qualitatively or quantitatively determining the presence or concentration of the biomolecule under investigation.

"Amyloid β, Aβ or β-amyloid" is an art recognized term and refers to amyloid β proteins and peptides, amyloid β precursor protein (APP), as well as modifications, fragments and any functional equivalents thereof. As used herein, amyloid β refers to any fragment produced by proteolytic cleavage of APP but especially those fragments which are involved in or associated with the amyloid pathologies including, but not limited to, $A\beta_{1-38}$, $A\beta_{1-39}$, $A\beta_{1-40}$, $A\beta_{1-41}$ $A\beta_{1-42}$ and $A\beta_{1-43}$.

The structure and sequences of the amyloid β peptides as mentioned above are well known to those of ordinary skill in the art and methods of producing said peptides or of extracting them from brain and other tissues are described, for example, in Glenner and Wong, Biochem Biophys Res Comm 129, 885-890 (1984). Moreover, amyloid β peptides are also commercially available in various forms.

"Aβ Fibril" or "Aβ Filament" or "amyloid fibrils" are polymeric forms of monomeric protein forming individual or bundled fibers with constant fiber diameter which are insoluble in aqueous medium and contain large amounts of a cross-β structure in their core; mostly with beta-strands perpendicular to the fibril axis.

"Monomeric Aβ" or "Aβ monomer" are completely solubilized amyloid β protein without aggregated complexes in aqueous medium.

"Proto-fibrils" or "proto-fibrillar preparation" as used herein refers to high molecular weight fractions of polymeric Aβ amyloid peptides, which are enriched with soluble amyloid Aβ oligomers.

"Polymeric soluble amyloid" and "oligomeric amyloid peptides Aβ" and "Aβ oligomer" are used interchangeably herein and refer to multiple aggregated monomers of amyloid peptides, or of amyloid-like peptides, or of modified or truncated amyloid peptides or of other derivates of amyloid peptides forming oligomeric or polymeric structures which are soluble both in vitro in aqueous medium and in vivo in the mammalian or human body more particularly in the brain, but particularly to multiple aggregated monomers of amyloid peptides or of modified or truncated amyloid peptides or of derivatives thereof, which are soluble in the mammalian or human body more particularly in the brain.

"Polymeric soluble amyloid Aβ peptides" and "oligomeric amyloid Aβ peptides" and "Aβ oligomer" are used interchangeably herein and refers to multiple aggregated monomers of amyloid Aβ peptides, or of modified or truncated amyloid Aβ peptides or of other derivates of amyloid Aβ peptides forming oligomeric or polymeric structures which are soluble both in vitro in aqueous medium and in vivo in the mammalian or human body more particularly in the brain, but particularly to multiple aggregated monomers of amyloid β (Aβ) or of modified or truncated amyloid β (Aβ) peptides or of derivatives thereof, which are soluble in the mammalian or human body more particularly in the brain.

With respect to a monoclonal antibody including any functionally equivalent antibody or functional parts thereof, which antibody binds to Aβ monomeric peptide 1-40 particularly to Aβ monomeric peptide 1-40 and to soluble polymeric and/or oligomeric amyloid peptide comprising a plurality of Aβ1-42 monomeric peptides but shows a substantially weaker binding to Aβ monomeric peptide 1-28 and an intermediated binding to monomeric peptide 1-42 and essentially no binding to Aβ monomeric peptide 17-40, by a "substantially weaker binding" a binding is meant, which is at least about 80%, particularly at least about 85%, more particularly at least about 90% but especially at least about 95% less than the binding to Aβ monomeric peptide 1-40.

With respect to a monoclonal antibody including any functionally equivalent antibody or functional parts thereof, which antibody binds to Aβ monomeric peptide 1-42 and polymeric soluble Aβ peptides comprising a plurality of Aβ$_{1-42}$ monomeric peptides and Aβ fibrils or fibers incorporating a plurality of said polymeric peptides, but shows a substantially weaker binding to Aβ monomeric peptide 1-28 and essentially no binding to Aβ monomeric peptide 17-40, by a "substantially weaker binding" a binding is meant, which is at least about 60%, particularly at least about 65%, more particularly at least about 70%, even more particularly at least about 80%, but especially at least about 90% and up to 100% less than the binding to Aβ monomeric peptide 1-42.

With respect to a monoclonal antibody including any functionally equivalent antibody or functional parts thereof, which antibody binds to Aβ monomeric peptide 1-40 particularly to Aβ monomeric peptide 1-40 and to soluble polymeric and/or oligomeric amyloid peptide comprising a plurality of Aβ1-42 monomeric peptides but shows a substantially weaker binding to Aβ monomeric peptide 1-28 and an intermediated binding to monomeric peptide 1-42 and essentially no binding to Aβ monomeric peptide 17-40, by an "intermediate binding" a binding is meant, which is at least about 60%, particularly at least about 65%, more particularly at least about 70%, even more particularly at least about 80%, less than the binding to Aβ monomeric peptide 1-40.

With respect to a monoclonal antibody including any functionally equivalent antibody or functional parts thereof, which antibody binds to Aβ monomeric peptide 1-40 particularly to Aβ monomeric peptide 1-40 and to soluble polymeric and/or oligomeric amyloid peptide comprising a plurality of Aβ1-42 monomeric peptides but shows a substantially weaker binding to Aβ monomeric peptide 1-28 and an intermediated binding to monomeric peptide 1-42 and essentially no binding to Aβ monomeric peptide 17-40, by "essentially no binding" a binding is meant, which is at least about 95%, particularly at least about 98%, but especially at least about 99% and up to 100% less than the binding to Aβ monomeric peptide 1-40.

With respect to a monoclonal antibody including any functionally equivalent antibody or functional parts thereof, which antibody binds to Aβ monomeric peptide 1-42 and polymeric soluble Aβ peptides comprising a plurality of Aβ$_{1-42}$ monomeric peptides and Aβ fibrils or fibers incorporating a plurality of said polymeric peptides, but shows a substantially weaker binding to Aβ monomeric peptide 1-28 and essentially no binding to Aβ monomeric peptide 17-40, by "essentially no binding" a binding is meant, which is at least about 85%, particularly at least about 90%, more particularly at least about 95%, even more particularly at least about 98%, but especially at least about 99% and up to 100% less than the binding to Aβ monomeric peptide 1-42.

The binding of the antibody according to the invention as described herein, particularly a monoclonal antibody including any functionally equivalent antibody or functional parts thereof, to Aβ monomeric peptides is determined by an ELISA-type assay, particularly by an ELISA assay using biotinylated Aβ monomeric peptides, but especially by an ELISA assay as described in Example 16 below.

The language "diseases and disorders which are caused by or associated with amyloid or amyloid-like proteins" includes, but is not limited to, diseases and disorders caused by the presence or activity of amyloid-like proteins in monomeric, fibril, or polymeric state, or any combination of the three. Such diseases and disorders include, but are not limited to, amyloidosis, endocrine tumors, and macular degeneration.

The term "optically associated amyloid diseases" refers to drusen-related optic neuropathy, cataract due to beta-amyloid deposition, and macular degemation.

The term "amyloidosis" refers to a group of diseases and disorders associated with amyloid plaque formation including, but not limited to, secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; and senile cardiac amyloidosis, and various eye diseases including macular degeneration, drusen-related optic neuropathy, and cataract due to beta-amyloid deposition By "isolated" is meant a biological molecule free from at least some of the components with which it naturally occurs.

The terms "antibody" or "antibodies" as used herein are art recognized terms and are understood to refer to molecules or active fragments of molecules that bind to known antigens, particularly to immunoglobulin molecules and to immunologically active portions of immunoglobulin molecules, i.e. molecules that contain a binding site that immunospecifically binds an antigen. The immunoglobulin according to the invention can be of any type (IgG, IgM, IgD, IgE, IgA and IgY) or class (IgG1, IgG2, IgG3, IgG4, IgA1 and IgA2) or subclasses of immunoglobulin molecule.

"Antibodies" are intended within the scope of the present invention to include monoclonal, polyclonal, chimeric, single chain, bispecific or bi-effective, simianized, human and humanized antibodies as well as active fragments thereof. Examples of active fragments of molecules that bind to known antigens include Fab, F(ab')$_2$, scFv and Fv fragments, including the products of an Fab immunoglobulin expression library and epitope-binding fragments of any of the antibodies and fragments mentioned above.

Such active fragments can be derived from an antibody of the present invention by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl. Acad Sci USA, 86:10029-10032 (1989), Hodgson et al., Bio/Technology, 9:421 (1991)).

A "humanized antibody" may also be obtained by a novel genetic engineering approach that enables production of affinity-matured humanlike polyclonal antibodies in large animals such as, for example, rabbits (see, e.g. U.S. Pat. No. 7,129,084).

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody. For the purpose of the present invention, "monoclonal antibody" is also to be understood to comprise antibodies that are produced by a mother clone which has not yet reached full monoclonality.

The term "CDR" refers to the hypervariable region of an antibody. The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions are based on sequence variability and are the most commonly used (Kabat et al., Sequences of Proteins of Immunological Interest, 5th Ed. Public Health Service, National Institutes of Health, Bethesda, Md. (1991)).

The letters "HC" and "LC" preceding the term "CDR" refer, respectively, to a CDR of a heavy chain and a light chain. Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991).

Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Functionally equivalent antibody" is understood within the scope of the present invention to refer to an antibody which substantially shares at least one major functional property with an antibody, for example functional properties herein described including, but not limited to: binding specificity to the β-amyloid protein, particularly to the $A\beta_{1-42}$ protein, and more particularly to the 4-16 epitopic region of the $A\beta_{1-42}$ protein, immunoreactivity in vitro, inhibition of aggregation of the $A\beta_{1-42}$ monomers into high molecular polymeric fibrils and/or disaggregation of preformed $A\beta_{1-42}$ polymeric fibrils, and/or a β-sheet breaking property and alleviating the effects of diseases and disorders which are caused by or associated with amyloid or amyloid-like proteins including, but not limited to, amyloidosis, endocrine tumors, and macular degeneration, when administered prophylactically or therapeutically. The antibodies can be of any class such as IgG, IgM, or IgA, etc or any subclass such as IgG1, IgG2a, etc and other subclasses described herein above or known in the art, but particularly of the IgG4 class. Further, the antibodies can be produced by any method, such as phage display, or produced in any organism or cell line, including bacteria, insect, mammal or other type of cell or cell line which produces antibodies with desired characteristics, such as humanized antibodies. Antibodies can also be formed by combining a Fab portion and an Fc region from different species.

The term "bispecific" or "bifunctional" and "bi-effective" is used synonymously within the scope of this application to characterize an antibody which exhibits both an inhibition property on amyloid or amyloid-like fiber formation as well as a disaggregation property of amyloid or amyloid-like fibers.

The term "antigen" refers to an entity or fragment thereof which can induce an immune response in an organism, particularly an animal, more particularly a mammal including a human. The term includes immunogens and regions thereof responsible for antigenicity or antigenic determinants.

As used herein, the term "soluble" means partially or completely dissolved in an aqueous solution.

Also as used herein, the term "immunogenic" refers to substances which elicit or enhance the production of antibodies, T-cells or other reactive immune cells directed against an immunogenic agent and contribute to an immune response in humans or animals.

An immune response occurs when an individual produces sufficient antibodies, T-cells and other reactive immune cells against administered immunogenic compositions of the present invention to moderate or alleviate the disorder to be treated.

"Polymeric soluble amyloid" refers to multiple aggregated monomers of amyloid peptides, or of amyloid-like peptides, or of modified or truncated amyloid peptides or of other derivates of amyloid peptides forming oligomeric or polymeric structures which are soluble in the mammalian or human body more particularly in the brain, but particularly refer to multiple aggregated monomers of amyloid β (Aβ) or of modified or truncated amyloid β (Aβ) peptides or of derivatives thereof, which are soluble in the mammalian or human body more particularly in the brain.

The term "hybridoma" is art recognized and is understood by those of ordinary skill in the art to refer to a cell produced by the fusion of an antibody-producing cell and an immortal cell, e.g. a multiple myeloma cell. Such a hybrid cell is capable of producing a continuous supply of antibody. See the definition of "monoclonal antibody" above and the Examples below for a more detailed description of one art known method of fusion.

The term "carrier" as used herein means a structure in which antigenic peptide or supramolecular construct can be incorporated into or can be associated with, thereby presenting or exposing antigenic peptides or part of the peptide to the immune system of a human or animal. Any particle that can be suitably used in animal or human therapy such as, for example, a vesicle, a particle or a particulate body may be used as a carrier within the context of the present invention. The term further comprises methods of delivery wherein supramolecular antigenic construct compositions comprising the antigenic peptide may be transported to desired sites by delivery mechanisms. One example of such a delivery system utilizes colloidal metals such as colloidal gold. The term "carrier" further comprises delivery mechanisms known to those of ordinary skill in the art including, but not limited to, keyhole limpet hemocyanin (KLH), bovine serum albumin (BSA) and other adjuvants.

In a supramolecular antigenic construct according to the present invention, the liposome may have a dual function in that it can be used as a carrier comprising a supramolecular construct as described herein and, at the same time, function as an adjuvant to increase or stimulate the immune response within the target animal or human to be treated with the therapeutic vaccine according to the invention. It is also to be understood that the supramolecular antigenic construct compositions of the present invention can further comprise additional adjuvants such as, for example, lipid A, alum, calcium phosphate, interleukin 1, and/or microcapsules of polysaccharides and proteins, but particularly a detoxified lipid A, such as monophosphoryl or diphosphoryl lipid A, or alum, further preservatives, diluents, emulsifiers, stabilizers, and other components that are known and used in vaccines in the art. Moreover, any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), TITERMAX® (polyoxyethylene-polyoxypropylene copolymer adjuvants from CytRx Corporation), modified lipid adjuvants from Chiron Corporation, saponin derivative adjuvants from Cambridge Biotech, killed Bordetella pertussis, the lipopolysaccharide (LPS) of gram-negative bacteria, large polymeric anions such as dextran sulfate, and inorganic gels such as alum, aluminum hydroxide, or aluminum phosphate.

Carrier proteins that can be used in the supramolecular antigenic construct compositions of the present invention include, but are not limited to, maltose binding protein "MBP"; bovine serum albumin "BSA"; keyhole lympet hemocyanin "KLH"; ovalbumin; flagellin; thyroglobulin; serum albumin of any species; gamma globulin of any species; syngeneic cells; syngeneic cells bearing Ia antigens; and polymers of D- and/or L-amino acids.

Further, the term "therapeutically effective amount" refers to the amount of antibody which, when administered to a human or animal, elicits an immune response which is sufficient to result in a therapeutic effect in said human or animal. The effective amount is readily determined by one of ordinary skill in the art following routine procedures.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for example 95% identity with a reference sequence of the present invention, the parameters are preferably adjusted so that the percentage of identity is calculated over the entire length of the reference sequence and homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

As used herein a "conservative change" refers to alterations that are substantially conformationally or antigenically neutral, producing minimal changes in the tertiary structure of the mutant polypeptides, or producing minimal changes in the antigenic determinants of the mutant polypeptides, respectively, as compared to the native protein. When referring to the antibodies and antibody fragments of the invention, a conservative change means an amino acid substitution that does not render the antibody incapable of binding to the subject receptor. One of ordinary skill in the art will be able to predict which amino acid substitutions can be made while maintaining a high probability of being conformationally and antigenically neutral. Such guidance is provided, for example in Berzofsky, (1985) Science 229:932-940 and Bowie et al. (1990) Science 247:1306-1310. Factors to be considered that affect the probability of maintaining conformational and antigenic neutrality include, but are not limited to: (a) substitution of hydrophobic amino acids is less likely to affect antigenicity because hydrophobic residues are more likely to be located in a protein's interior; (b) substitution of physiochemically similar, amino acids is less likely to affect conformation because the substituted amino acid structurally mimics the native amino acid; and (c) alteration of evolutionarily conserved sequences is likely to adversely affect conformation as such conservation suggests that the amino acid sequences may have functional importance. One of ordinary skill in the art will be able to assess alterations in protein conformation using well-known assays, such as, but not limited to microcomplement fixation methods (see, e.g. Wasserman et al. (1961) J. Immunol. 87:290-295; Levine et al. (1967) Meth.

Enzymol. 11:928-936) and through binding studies using conformation-dependent monoclonal antibodies (see, e.g. Lewis et al. (1983) Biochem. 22:948-954).

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 70° C., preferably at 65° C. (regarding the definition of SSPE, SSC and Denhardts solution see Sambrook et al. Molecular Biology: A Laboratory Manual, Cold Spring Harbor Press, Cold Spring Harbor, N.Y., 1989). Stringent hybridization conditions as for instance described in Sambrook et al, supra, are particularly preferred. Particularly preferred stringent hybridization conditions are for instance present if hybridization and washing occur at 65° C. as indicated above. Non-stringent hybridization conditions, for instance with hybridization and washing carried out at 45° C. are less preferred and at 35° C. even less.

The present invention may be understood more readily by reference to the following detailed description of specific embodiments included herein. Although the present invention has been described with reference to specific details of certain embodiments thereof, it is not intended that such details should be regarded as limitations upon the scope of the invention.

The present invention provides antibodies and functional parts thereof which are conformationally sensitive antibodies. These antibodies recognize specific epitopes on a wide variety of amyloid proteinic antigens. The antibodies are useful for diagnostic and therapeutic intervention in diseases and disorders which are caused by or associated with amyloid or amyloid-like proteins, and especially in Alzheimer's Disease.

Antibodies may be administered to individuals to passively immunize them against a variety of diseases or disorders which are caused by or associated with amyloid or amyloid-like proteins, such as Alzheimer's disease.

The antibodies provided herein are monoclonal or polyclonal antibodies having binding specificity for antigenic peptides involved in the initiation, progression, and/or worsening of various diseases or disorders which are caused by or associated with amyloid or amyloid-like proteins, such as, Alzheimer's disease.

The antibodies according to the invention are prepared by immunizing an animal, such as a mouse, rat, rabbit or any other animal species which can produce native or human antibodies, with a supramolecular antigenic construct composition.

The supramolecular antigenic constructs as disclosed herein generally comprise peptides modified to enhance antigenic effect wherein such peptides are modified via pegylation (using polyethylene glycol or modified polyethylene glycol), or modified via other methods such as by palmitic acid, poly-amino acids (e.g. poly-glycine, poly-histidine), polysaccharides (e.g. polygalacturonic acid, polylactic acid, polyglycolide, chitin, chitosan), synthetic polymers (polyamides, polyurethanes, polyesters) or co-polymers (e.g. poly (methacrylic acid) and N-(2-hydroxy) propyl methacrylamide) and the like.

Modification by palmitic acid (palmitoylation), while providing an anchor for the peptide in the liposome bilayer, due to the relative reduced length of the $C_{16:0}$ fatty acid moiety leads to the peptide practically laying on the liposome surface. Therefore, the cells processing the antigen will have to take up the entire liposome with the peptide, which, in the majority of cases, results in a slower immune response in relative terms.

In one embodiment of the invention, a modified amyloid $A\beta_{22-35}$ peptide and $A\beta_{29-40}$, peptide, respectively, is used in the preparation of an antibody, particularly a monoclonal antibody according to the invention. The modified amyloid peptide may be synthesized following the method reported in Nicolau et. al. 2002. The approach reported in Nicolau et al involves modifying the antigenic peptide by an on-resin grafting of a lipophilic or hydrophobic moiety, to the terminal amino acid residues of a pre-formed peptide resulting in a product of considerably high purity. In particular, a protected amino acid, particularly a Fmoc-protected amino acid, is attached to a resin using known coupling chemistry. The protecting group is removed and a second protected amino acid residue coupled. Standard automated peptide synthesis using known protection chemistry, particularly Fmoc/tBu chemistry, and standard side-chain protecting groups are then used to synthesize the Aβ antigenic peptide by coupling on amino acids 22 to 35 and 29-40, respectively, of amyloid protein $A\beta_{1-42}$. to produce the peptide fragment. In a final step two further protected amino acids are coupled to the growing peptide fragment. The Mtt groups can then be selectively cleaved and coupled to palmitic acid. After washing of the resin, the protecting group is removed and the resin simultaneously cleaved, followed by side-chain deprotections using standard methodology. The final product can then be obtained in high purity and its identity confirmed by methods known in the art such as, for example, electrospray mass spectrometry.

The lipophilic or hydrophobic moiety according to the present invention may be a fatty acid, a triglyceride or a phospholipid wherein the fatty acid carbon back bone has at least 10 carbon atoms. Particularly, the lipophilic or hydrophobic moiety is a fatty acids with a carbon backbone of at least approximately 14 carbon atoms and up to approximately 24 carbon atoms, with each individual number of carbon atom falling within this range also being part of the present invention. More particularly, the lipophilic or hydrophobic moiety has a carbon backbone of at least 14 carbon atoms. Examples of hydrophobic moieties include, but are not limited to, palmitic acid, stearic acid, myristic acid, lauric acid, oleic acid, linoleic acid, linolenic acid and cholesterol or DSPE. In a specific embodiment of the present invention the lipophilic or hydrophobic moiety is palmitic acid.

To enhance the immune response, another anchor/spacer can suitably be applied to reconstitute the peptide in the liposome, e.g. polyethylene glycol (PEG).

PEG is covalently attached to an amino acid residue bound at both termini of the peptide, in particular Glu, Cys or Lys amino acid residue or any other amino acid residue that can be suitably used to covalently bind PEG to the peptide. At the other end of the chain a hydrophobic moiety may be covalently bound to function as the anchoring element in the liposome bilayer such as, for example, phosphatidyl ethanol amine (PEA). Thus, the liposome still functions as an adjuvant and the peptide being sufficiently far away from the bilayer can be processed alone and thus increases its immunogenicity as compared to the palmitoylated antigen.

In certain embodiments, the supramolecular antigenic constructs used within the scope of the present invention comprise a peptide sequence, covalently attached to pegylated lysine-one at each terminus. The length of the PEG (polyethylenglycol) chain may vary from n=8 to n=150.000 or more, particularly from n=10 to n=80.000, more particularly from n=20 to n=10.000. In a specific embodiment of the invention the length of the PEG chain is not more than n=45, particularly between n=5 and n=40, more particularly between n=10 and n=30, and even more particularly n=10.

The supramolecular constructs described herein can be synthesized using automated peptide synthesis and known protection chemistry, particularly Fmoc/tBu chemistry and standard side-chain protecting groups. Typically, pegylation of peptides results in mixtures of regioisomers.

To achieve a site-specific attachment of a PEG-lipid conjugate to both the C- and N-terminus of Aβ partially protected peptides may be used. For those peptide sequences containing internal Lys or His residues an orthogonally protected Lys (ivDde) is added to each terminus. An additional Gly may be added to the C-terminal end to facilitate synthesis. The protecting group is removed and N-acetylated using acetic anhydride followed by selective cleavage of the ivDde groups.

A resin, particularly a 2-chlorotrityl resin, is to be favored which is acid sensitive and thus enables the isolation of protected peptides.

In a specific embodiment of the invention, the coupling reaction is performed in the solution phase. Selective cleavage from the resin under mild conditions then release the internally protected peptides.

Solution-phase couplings were achieved successfully with the peptides derived from a β-amyloid protein sequence such as, for example, a $A\beta_{22-35}$ and $A\beta_{29-40}$, respectively, to a PEG molecule modified by a fatty acid—phosphatidylcholine such as, for example, DSPE. Separation of the mono- and di-coupled products before final side-chain deprotections can be achieved by using cation-exchange chromatography. Subsequent peptide side-chain deprotections leads to the isolation of the desired conjugates with an acceptable purity. Purification can be achieved by methods well known in the art such as, for example, HPLC. etc.

This approach to the synthesis of N- and C-terminal lipid-PEG β-amyloid antigens using protected peptides is applicable to a wide variety of peptide sequences.

Liposomal antigens according to the invention may then be prepared as described in Nicolau et al., 2002. The modified amyloid Aβ antigenic peptide, particularly the modified PEGylated $A\beta_{22-35}$ and $A\beta_{29-40}$ antigenic peptide may be reconstituted in a construct consisting of liposomes, particularly liposomes made of dimyristoyl phosphatidyl choline (DMPC), dimyristoyl phosphatidyl ethanolamine (DMPEA), dimyristoyl phosphatidyl glycerol (DMPG) and cholesterol, optionally containing monophosphoryl lipid A.

In a specific embodiment of the invention liposomes with lipid A are used as adjuvant to prepare the anti-amyloid vaccine. Dimyristoylphosphatidyl-choline, -glycerol and cholesterol are mixed, particularly in a molar ratio of 0.9:1.0:0.7. A strong immunmodulator such as, for example, monophosphoryl lipid A is then added at a suitable concentration, particularly at a concentration of between 30 and 50 mg per mmol, more particularly at 40 mg per mmol of phospholipids. The modified antigenic Aβ peptide is then added at a molar ratio peptide to phospholipids of between 1:30 and 1:200, particularly at a molar ratio of between 1:1000, 1:50, and 1:120, more particularly of 1:100. Solvents are removed, for example through evaporation, and the resulting film hydrated with sterile buffer solution such as, for example PBS.

Liposomes may also be prepared by the crossflow injection technique as described, for example, in Wagner et al (2002) Journal of Liposome Research Vol 12(3), pp 259-270. During the injection of lipid solutions into an aqueous buffer system, lipids tend to form "precipitates", followed by self arrangement in vesicles. The obtained vesicle size depends on factors such as lipid concentration, stirring rate, injection rate, and the choice of lipids. The preparation system may consist of a crossflow injection module, vessels for the polar phase (e.g. a PBS buffer solution), an ethanol/lipid solution vessel and a pressure device, but particularly a nitrogen pressure device. While the aqueous or polar solution is pumped through the crossflow injection module the ethanol/lipid solution is injected into the polar phase with varying pressures applied.

The liposome still functions as an adjuvant and the peptide being sufficiently far away from the bilayer can be processed alone and thus increases its immunogenicity as compared to the palmitoylated antigen.

The free PEG terminus is covalently attached to a molecule of phosphatidyl-ethanolamine (where the fatty acid can be: myristic, palmitic, stearic, oleic etc. or a combination thereof) to function as the anchoring element. This supramolecular structure may be anchored by reconstitution in liposomes consisting of phospholipids and cholesterol (phosphatidylethanol amine, phosphatidyl glycerol, cholesterol in varied molar ratios. Other phospholipids can be used. Lipid A is used at a concentration of approximately 40 μg/μmole of phospholipids.

In certain embodiments, the palmitoylated or pegylated supramolecular antigenic constructs comprise a peptide having the amino acid sequence of β-amyloid. The peptides may also comprise or correspond to whole amyloid beta peptide and active fragments thereof. Additionally, peptides useful for the present invention in particular comprise $A\beta_{22-35}$ and $A\beta_{29-40}$, respectively, and active fragments thereof.

For eliciting and preparing antibodies and for determining immuogenicity of the modified Aβ antigenic construct a suitable animal selected from the group consisting of mice, rats, rabbits, pigs, birds, etc, but particularly mice, especially C57BL/6 mice are immunized with the antigenic peptide. Immunogenicity of the antigenic construct is determined by probing sera samples in suitable time intervals after immunization using a immunoassay such as, for example, an ELISA assay.

The monoclonal antibodies of the present invention can be prepared using classical cloning and cell fusion techniques well known in the art. The immunogen (antigen) of interest, is typically administered (e.g. intraperitoneal injection) to wild type or inbred mice (e.g. BALB/c or especially C57BL/6 mice), rats, rabbits or other animal species or transgenic mice which can produce native or human antibodies. The immunogen can be administered alone, or mixed with adjuvant, or expressed from a vector (VEE replicon vector, vaccinia), or as DNA, or as a fusion protein to induce an immune response. Fusion proteins comprise the peptide against which an immune response is desired coupled to carrier proteins, such as, for example, beta.-galactosidase, glutathione S-transferase, keyhole limpet hemocyanin (KLH), and bovine serum albumin. In these cases, the peptides serve as haptens with the carrier proteins. After the animal is boosted, for example, two or more times, spleen cells are harvested from the immunized animals and hybridomas generated by fusing sensitized spleen cells with a myeloma cell line, such as murine SP2/O myeloma cells (ATCC, Manassas, Va.) using the well-known processes of Kohler and Milstein (Nature 256: 495-497 (1975)) and Harlow and Lane (Antibodies: A Laboratory Manual (Cold Spring Harbor Laboratory, New York 1988)).

In a specific embodiment of the invention the antigenic construct according to the invention, particularly a vaccine composition comprising said antigenic construct in a pharmaceutically acceptable form, is administered in repeated doses, in particular in 1 to 15 doses, more particularly in 2 to 10 doses, even more particularly in 3 to 7 doses but especially in 4 to 6 doses, in time intervals of between 1 and 10 weeks, particularly in time intervals of between 1 and 6 weeks, more particularly in time intervals of between 1 and 4 weeks, and even more particularly in time intervals of between 2 and 3 weeks. The immune response is monitored by taking sera samples at a suitable time after boosting, particularly 3 to 10 days after boosting, more particularly 4 to 8 days after boosting and more particularly 5 to 6 days after boosting and determining the immunogenicity of the antigenic construct using known methodology, particularly one of the commonly used immunoassays such as, for example, an ELISA assay Immunization with the antigenic construct according to the invention, but particularly with a vaccine composition comprising the antigenic construct according to the invention in a pharmaceutically acceptable form leads to a significant immune response in the treated animal. Animals, but especially mice with therapeutic titers are selected for a fusion of antibody producing cells, particularly B-lymphocytes with a continuously growing or immortal cell line, such as a myeloma cell line. The cells are induced to fuse by the addition of polyethylene glycol. Therapeutic titers are those which give a positive result in an ELISA assay in a dilution of between 1:4000 and 1:6000, particularly of between 1:4500 and 1:5500, more particularly of 1:5000.

The resulting hybrid cells are then cloned in the conventional manner, e.g. using limiting dilution, and the resulting clones, which produce the desired monoclonal antibodies, cultured.

The so obtained hybridomas are chemically selected by plating the cells in a selection medium containing hypoxanthine, aminopterin and thymidine (HAT).

Hybridomas are subsequently screened for the ability to produce monoclonal antibodies against specific amyloid-associated diseases or disorders. Hybridomas producing antibodies of interest are cloned, expanded and stored frozen for future production. The preferred hybridoma produces a monoclonal antibody having the IgG isotype.

The polyclonal antibody is prepared by immunizing animals, such as mice or rabbits, or any other suitable animal with supramolecular antigenic construct compositions of the present invention described herein. Blood sera is subsequently collected from the animals, and antibodies in the sera screened for binding reactivity against the amyloid protein.

The antibodies according to the invention can be prepared in a physiologically acceptable formulation and may comprise a pharmaceutically acceptable carrier, diluent and/or excipient using known techniques. For example, the antibody according to the invention and as described herein including any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical composition according to the invention can be accomplished according to standard methodology know to those of ordinary skill in the art.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It is well known to those of ordinary skill in the art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The composition may be administered in combination with other compositions comprising an biologically active substance or compound, particularly at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, β- and γ-secretase inhibitors, tau proteins, neurotransmitter, β-sheet breakers, anti-inflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B12, cysteine, a precursor of acetylcholine, lecithin, choline, *Ginkgo biloba*, acyetyl-L-carnitine, idebenone, propentofylline, or a xanthine derivative, together with an antibody according to the present invention and, optionally, a pharmaceutically acceptable carrier and/or a diluent and/or an excipient and instructions for the treatment of diseases.

Proteinaceous pharmaceutically active matter may be present in amounts between 1 ng and 10 mg per dose. Generally, the regime of administration should be in the range of between 0.1 µg and 10 mg of the antibody according to the invention, particularly in a range 1.0 µg to 1.0 mg, and more particularly in a range of between 1.0 µg and 100 µg, with all individual numbers falling within these ranges also being part of the invention. If the administration occurs through continuous infusion a more proper dosage may be in the range of between 0.01 µg and 10 mg units per kilogram of body weight per hour with all individual numbers falling within these ranges also being part of the invention.

Administration will generally be parenterally, e.g. intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on its the intended use.

When the binding target is located in the brain, certain embodiments of the invention provide for the antibody or active fragment thereof to traverse the blood-brain barrier. Certain neurodegenerative diseases are associated with an increase in permeability of the blood-brain barrier, such that the antibody or active fragment thereof can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or active fragment thereof across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)) and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or active fragment thereof across the blood-brain barrier include, but are not limited to, encapsulating the antibody or active fragment thereof in liposomes that are coupled to active fragments thereof that bind to receptors on the vascular endothelium of the blood-brain barrier (see, e.g., U.S. Patent Application Publication No. 20020025313), and coating the antibody or active fragment thereof in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or active fragment thereof across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

In a further embodiment the present invention provides methods and kits for the detection and diagnosis of amyloid-associated diseases or conditions, for diagnosing a predisposition to an amyloid-associated disease or condition or for monitoring minimal residual disease in a patient or for predicting responsiveness of a patient to a treatment with an antibody or a vaccine composition according to the invention and as described herein. These methods include known immunological methods commonly used for detecting or quantifying substances in biological samples or in an in situ condition.

Diagnosis of an amyloid-associated disease or condition or of a predisposition to an amyloid-associated disease or condition in a patient may be achieved by detecting the immunospecific binding of an antibody of the invention, particularly a monoclonal antibody or an active fragment thereof to an epitope of the amyloid protein in a sample or in situ, which includes bringing the sample or a specific body part or body area suspected to contain the amyloid protein into contact with an antibody which binds an epitope of the amyloid protein, allowing the antibody to bind to the amyloid protein to form an immunological complex, detecting the formation of the immunological complex and correlating the presence or absence of the immunological complex with the presence or absence of amyloid protein in the sample or specific body part or area, optionally comparing the amount of said immunological complex to a normal control value, wherein an increase in the amount of said immunological complex compared to a normal control value indicates that said patient is suffering from or is at risk of developing an amyloid-associated disease or condition. The amyloid protein may be in the monomeric, fibril, and/or polymeric form. The antibody or active portion thereof may be specific for the monomeric, fibril, and/or polymeric forms of the amyloid protein.

Monitoring minimal residual disease in a patient following treatment with an antibody or a vaccine composition according to the invention may be achieved by detecting the immunospecific binding of an antibody of the invention, particularly a monoclonal antibody or an active fragment thereof to an epitope of the amyloid protein in a sample or in situ, which includes bringing the sample or a specific body part or body area suspected to contain the amyloid protein into contact with an antibody which binds an epitope of the amyloid protein, allowing the antibody to bind to the amyloid protein to form an immunological complex, detecting the formation of the immunological complex and correlating the presence or absence of the immunological complex with the presence or absence of amyloid protein in the sample or specific body part or area, optionally comparing the amount of said immunological complex to a normal control value, wherein an increase in the amount of said immunological complex compared to a normal control value indicates that said patient may still suffer from a minimal residual disease. The amyloid protein may be in the monomeric, fibril, and/or polymeric form. The antibody or active portion thereof may be specific for the monomeric, fibril, and/or polymeric forms of the amyloid protein.

Predicting responsiveness of a patient to a treatment with a vaccine composition according to the invention may be achieved by detecting the immunospecific binding of a monoclonal antibody or an active fragment thereof to an epitope of the amyloid protein in a sample or in situ, which includes bringing the sample or a specific body part or body area suspected to contain the amyloid protein into contact with an antibody which binds an epitope of the amyloid protein, allowing the antibody to bind to the amyloid protein to form an immunological complex, detecting the formation of the immunological complex and correlating the presence or absence of the immunological complex with the presence or absence of amyloid protein in the sample or specific body part or area, optionally comparing the amount of said immunological complex before and after onset of the treatment, wherein an decrease in the amount of said immunological complex indicates that said patient has a high potential of being responsive to the treatment. The amyloid protein may be in the monomeric, fibril, and/or polymeric form. The antibody or active portion thereof may be specific for the monomeric, fibril, and/or polymeric forms of the amyloid protein.

Biological samples that may be used in the diagnosis of an amyloid-associated disease or condition, for diagnosing a predisposition to an amyloid-associated disease or condition or for monitoring minimal residual disease in a patient or for predicting responsiveness of a patient to a treatment with an antibody or a vaccine composition according to the invention and as described herein are, for example, fluids such as serum, plasma, saliva, gastric secretions, mucus, cerebrospinal fluid, lymphatic fluid and the like or tissue or cell samples obtained from an organism such as neural, brain, cardiac or vascular tissue. For determining the presence or absence of the amyloid protein in a sample any immunoassay known to those of ordinary skill in the art may be used such as, for example, assays which utilize indirect detection methods using secondary reagents for detection, ELISA's and immunoprecipitation and agglutination assays. A detailed description of these assays is, for example, given in See Harlow and Lane, Antibodies: A Laboratory Manual (Cold Spring Harbor Laboratory, New York 1988 555-612, WO96/13590 to Maertens and Stuyver, Zrein et al. (1998) and WO96/29605.

For in situ diagnosis, the antibody or any active and functional part thereof may be administered to the organism to be diagnosed by methods known in the art such as, for example, intravenous, intranasal, intraperitoneal, intracerebral, intraarterial injection such that a specific binding between an antibody according to the invention with an eptitopic region on the amyloid protein may occur. The antibody/antigen complex may conveniently be detected through a label attached to the antibody or a functional fragment thereof or any other art-known method of detection.

The immunoassays used in diagnostic applications or in applications for diagnosing a predisposition to an amyloid-associated disease or condition or for monitoring minimal residual disease in a patient or for predicting responsiveness of a patient to a treatment with an antibody or a vaccine composition according to the invention and as described herein. typically rely on labelled antigens, antibodies, or secondary reagents for detection. These proteins or reagents can be labelled with compounds generally known to those of ordinary skill in the art including enzymes, radioisotopes, and fluorescent, luminescent and chromogenic substances including, but not limited to colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Antibodies useful in these assays include monoclonal antibodies, polyclonal antibodies, and affinity purified polyclonal antibodies.

Alternatively, the antibody may be labelled indirectly by reaction with labelled substances that have an affinity for immunoglobulin, such as protein A or G or second antibodies. The antibody may be conjugated with a second substance and detected with a labelled third substance having an affinity for the second substance conjugated to the antibody. For example, the antibody may be conjugated to biotin and the antibody-biotin conjugate detected using labelled avidin or streptavidin. Similarly, the antibody may be conjugated to a hapten and the antibody-hapten conjugate detected using labelled anti-hapten antibody.

Those of ordinary skill in the art will know of these and other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 81:1-40). Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein the antibody is labeled indirectly by reactivity with a second antibody that has been labeled with a detectable label. The second antibody is preferably one that binds to antibodies of the animal from which the monoclonal antibody is derived. In other words, if the monoclonal antibody is a mouse antibody, then the labeled, second antibody is an anti-mouse antibody. For the antibody to be used in the assay described herein, this label is preferably an antibody-coated bead, particularly a magnetic bead. For the antibody to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antibody and the analyte. According to one embodiment of the present invention, the presence of the amyloid protein is determined using a pair of antibodies, each specific for amyloid protein. One of said pairs of antibodies is referred to herein as a "detector antibody" and the other of said pair of antibodies is referred to herein as a "capture antibody". The monoclonal antibody of the present invention can be used as either a capture antibody or a detector antibody. The monoclonal antibody of the present invention can also be used as both capture and detector antibody, together in a single assay. One embodiment of the present invention thus uses the double antibody sandwich method for detecting amyloid protein in a sample of biological fluid. In this method, the analyte (amyloid protein) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those of ordinary skill in the art. More recently, a number of porous material such as nylon, nitrocellulose, cellulose acetate, glass fibers and other porous polymers have been employed as solid supports.

The present invention also relates to a diagnostic kit for detecting amyloid protein in a biological sample comprising a composition as defined above. Moreover, the present invention relates to the latter diagnostic kit which, in addition to a composition as defined above, also comprises a detection reagent as defined above. The term "diagnostic kit" refers in general to any diagnostic kit known in the art. More specifically, the latter term refers to a diagnostic kit as described in Zrein et al. (1998).

It is still another object of the present invention to provide novel immunoprobes and test kits for detection and diagnosis of amyloid-associated diseases and conditions comprising antibodies according to the present invention. For immunoprobes, the antibodies are directly or indirectly attached to a suitable reporter molecule, e.g., an enzyme or a radionuclide. The test kit includes a container holding one or more antibodies according to the present invention and instructions for using the antibodies for the purpose of binding to amyloid protein to form an immunological complex and detecting the formation of the immunological complex such that presence or absence of the immunological complex correlates with presence or absence of amyloid protein.

EXAMPLES

Example 1

Methods for Making Supramolecular Antigenic Constructs

Synthesis of Pegylated β-Amyloid Peptide Antigen

To enhance the immune response, an anchor/spacer has been applied to reconstitute the peptide in the liposome, e.g. polyethylene glycol (PEG). PEG was covalently attached to the lysine residue bound at both termini of the peptide. At the other end of the chain (PEG n=70) phosphatidyl ethanol amine (PEA) was covalently bound to function as the anchoring element in the liposome bilayer. Thus, the liposome still functions as an adjuvant and the peptide being sufficiently far away from the bilayer can be processed alone and thus increases its immunogenicity as compared to the palmitoylated antigen.

The supramolecular constructs described herein were uniquely synthesized using standard Fmoc/tBu amino acid side-chain protections. Typically, pegylation of peptides results in mixtures of regioisomers. Herein a convenient method for the site-specific attachment of a PEG-lipid conjugate to both the C- and N-terminus of Aβ is demonstrated using partially protected peptides.

For those peptide sequences containing internal Lys or His residues (22-35), an orthogonally protected Lys(ivDde) was added to each terminus. An additional Gly was added to the C-terminal to facilitate synthesis. The Fmoc group was removed with 20% piperidine in DMF and N-acetylated using acetic anhydride. Selective cleavage of the ivDde groups was achieved with 3% hydrazine hydrate in DMF for one hour. The 2-chlorotrityl resin was favored over the more widely used Wang resin since the former proved to be much more resistant to hydrazinolysis. Furthermore, the 2-chlorotrityl resin is extremely acid sensitive and thus, unlike the Wang resin, enables the isolation of protected peptides. Indeed, it was necessary to perform the coupling reaction in the solution phase as coupling of the resin-bound peptide to the pre-activated pegylated lipid reagent DSPE-PEG-SPA did not give rise to any coupling product. Thus selective cleavage from the resin under mild conditions (acetic acid/trifluoroethanol/dichloromethane, 1:1:8, 1 h, rt) gave the internally protected peptides.

Solution-phase couplings were achieved successfully with the peptides derived from sequence $A\beta_{22-35}$ and $A\beta_{29-40}$, respectively, to DSPE-PEG-SPA in DMSO and excess base. The reactions were then quenched by the addition of excess ethanolamine for 2 h and the solution lyophilized.

For the sequence 29-40, no special protection strategy was required.

Purification by HPLC (semi-preparative reverse-phase $C_4$ column) gave between 50-70% purity of the N- and C-terminal PEG-lipid conjugates whose identities were confirmed by MALDI (matrix assisted laser desorption ionization). Each sequence showed considerable variation in the ease of the coupling reaction and conditions were adjusted accordingly (temperature, number of molar equivalents DSPE-PEG-SPA, time). For the separation of excess DSPE-PEG-SPA from the desired product HPLC purification is applied. Separation of the mono- and di-coupled products before final side-chain deprotections can be achieved by using cation-exchange chromatography. Subsequent peptide side-chain deprotections and separation of the excess quenched DSPE-PEG-SPA leads to the isolation of the desired conjugates with an acceptable purity.

This approach to the synthesis of N- and C-terminal lipid-PEG β-amyloid antigens using protected peptides is applicable to a wide variety of peptide sequences.

Example 2

Antibodies Elicited by Supramolecular Antigenic Constructs

Manufacturing of mAbs Raised Against Pegylated $A\beta_{22-35}$ and $A\beta_{29-40}$ Supramolecular Antigenic Constructs:

Liposomal antigens were prepared as described (Nicolau et al., 2002, PNAS, 99, 2332-37). The sequences PEG-$A\beta_{22-35}$ and $A\beta_{29-40}$ were reconstituted in a construct consisting of liposomes made of dimyristoyl phosphatidyl choline (DMPC), dimyristoyl phosphatidyl ethanolamine (DMPEA), dimyristoyl phosphatidyl glycerol (DMPG) and cholesterol (0.9:0.1:0.1:0.7 molar ratios) containing monophosphoryl lipid A (40 mg/mM phospholipids). These antigens were used for the immunization in C57BL/6 mice in 2 week intervals. 10-12 animals were immunized with each antigen. After 3 to 6 boostings, mice with therapeutic titers (when a 1:5,000 dilution of the sera were positive in ELISA) were selected for a fusion. Spleen cells are harvested from the immunized animals and hybridomas generated by fusing sensitized spleen cells with a myeloma cell line. The fusion of the mice's B-lymphocytes from the spleens was conducted with cells of myeloma cell line SP2-0. (ATCC, Manassas, Va.) using the well-known processes of Kohler and Milstein (Nature 256:

495-497 (1975)) and Harlow and Lane (Antibodies: A Laboratory Manual (Cold Spring Harbor Laboratory, New York 1988))

The cells were induced to fuse by the addition of polyethylene glycol. The resulting hybrid cells were then cloned in the conventional manner, e.g. using limiting dilution. IgG producing hybridoma clones were selected and tested for their specific binding to the $A\beta_{1-42}$ peptide by ELISA and the resulting clones, which produce the desired monoclonal antibodies, cultured.

The so obtained hybridomas were chemically selected by plating the cells in a selection medium containing hypoxanthine, aminopterin and thymidine (HAT).

Hybridomas were subsequently screened for the ability to produce monoclonal antibodies against specific amyloid-associated diseases or disorders. Hybridomas producing antibodies of interest were cloned, expanded and stored frozen for future production. The preferred hybridomas produce monoclonal antibodies having the IgG isotype.

Example 3

Specificity Determination for Antibody ACI-11-Ab-9 and ACI-12-Ab-11

To analyze the specificity of the antibody ACI-11-Ab-9 and ACI-12-Ab-11, different concentrations of pre-formed Amyloid 1-42, 1-40 and 17-40, 1-28 fibrils are blotted onto Hybond ECL Nitrocellulose Membrane (Amersham Biosciences). After blocking with 10% dry milk and 0.7% Tween 20, membranes are incubated with primary antibody at 20 μg/ml for 2 h at RT. After washing, membranes are incubated with horse radish peroxidase conjugated sheep anti-mouse IgG antibody (Amersham Biosciences) for 1 h at RT, washed and incubated with cheminluminescent solution followed by the exposure of the membrane to X-ray film.

To measure binding of the mAb ACI-11-Ab-9 and ACI-12-Ab-11 to amyloid β 1-42, 1-40 and 17-40, 1-28 fibers are pre-formed for seven days at 37° C. and blotted on the membrane. 20 μg/ml antibody is used to measure binding capacity and the bound antibody is detected by horse radish peroxidase conjugated sheep anti-mouse IgG antibody for 20 minutes of exposure.

Example 4

Thioflavin T (Th-T) Fluorescent Assay

To measure both inhibition of aggregation as well as disaggregation properties of the mAbs the Thioflavin T (Th-T) fluorescent assay was used which specifically binds to fibrillar $A\beta_{1-42}$ molecules and subsequently the fluorescent emission intensity correlates with the amount of $A\beta_{1-42}$ filaments present in the solution.

Aβ1-42 lyophilized powder was reconstituted in hexafluoroisopropanol (HFIP) to 1 mM. The peptide solution was sonicated for 15 min at room temperature, agitated overnight, and aliquots made into non-siliconized microcentrifuge tubes. The HFIP was then evaporated under a stream of argon. The resulting peptide film was vacuum dried for 10 min and stored at −80° C. until used.

4.1 Aβ1-42 Aggregation Assay

To assay for the antibody-mediated inhibition of Aβ1-42 aggregation the antibody was pre-diluted in PBS and an assay solution containing the following components was made in a non-siliconized incubation tube: 3.3 or 0.33 μM pre-diluted antibody, 10 μM thioflavin T, 33 μM Aβ1-42, and 8.2% DMSO. Therefore the final molar ratios of antibody to Aβ1-42 were 1:10 and 1:100. Appropriate control solutions were also prepared. The solutions were then incubated for 24 hrs at 37° C., and the spectrofluorescence (relative fluorescence units; RFU) read in six replicates in black 348-well plates (Perkin-Elmer) on a Perkin-Elmer FluoroCount spectrofluorometer. Inhibition of aggregation or disaggregation is expressed as mean % inhibition or disaggregation, respectively, according to the following equation $$\% \text{ inhibition} = \frac{(RFU \text{ of } pos\ contrl - RFU \text{ of } neg\ contrl) - (RFU \text{ of } sample \text{ with } A\beta1-42 - RFU \text{ of } sample \text{ without } A\beta1-42)}{RFU \text{ of } pos\ contrl - RFU \text{ of } neg\ contrl} \times 100$$

Antibody ACI-11-Ab-9 showed a significant inhibition of Aβ1-42 aggregation as compared to the control. At an antibody to Aβ1-42 molar ratio of 1:100 the inhibition averaged 34% (3 independent experiments), whereas at a 1:10 molar ratio the inhibition was 69% (2 independent experiments).

Antibody ACI-12-Ab-11 also showed a significant inhibition of Aβ1-42 aggregation as compared to the control. At an antibody to Aβ1-42 molar ratio of 1:100 the inhibition averaged 30% (2 independent experiments), whereas at a 1:10 molar ratio the inhibition was 66% (2 independent experiments).

4.2 Aβ1-42 Disaggregation Assay

To measure the disaggregation properties of the mAb the Thioflavin T (ThT) fluorescent assay was used which specifically binds to fibrillar $A\beta_{1-42}$ molecules and subsequently the fluorescent emission intensity correlates with the amount of $A\beta_{1-42}$ filaments present in the solution.

To assay for antibody-mediated disaggregation of pre-aggregated Aβ1-42, a low-molecular weight Aβ1-42, prepared as described above, was made up as a 110 μM solution in 27% DMSO and 1×PBS. This solution was then allowed to aggregate at 37° C. for 24 hrs after which the following were added: 3.3 or 0.33 μM pre-diluted antibody, and 10 μM thioflavin T. This resulted in a molar ratio of 1:10 and 1:100 antibody to Aβ1-42, containing 8.2% DMSO. This solution was then incubated for additional 24 hrs at 37° C. The spectrofluorescence was then measured and % disaggregation calculated as described above.

Antibody ACI-11-Ab-9 showed a significant disaggregation of pre-aggregated Aβ1-42 in the disaggregation assay. At an antibody to Aβ1-42 molar ratio of 1:100 the disaggregation averaged 22% (3 independent experiments), whereas at a 1:10 molar ratio the disaggregation was 52% (3 independent experiments).

Antibody ACI-12-Ab-11 also showed a significant disaggregation of pre-aggregated Aβ1-42 in the disaggregation assay. At an antibody to Aβ1-42 molar ratio of 1:100 the disaggregation averaged 18% (2 independent experiments), whereas at a 1:10 molar ratio the disaggregation was 54% (2 independent experiments).

From the above results it is evident that antibodies ACI-1-Ab-9 and ACI-12-Ab-11 exhibit bi-functionality in interacting with Aβ$_{1-42}$ filaments, in that both antibodies are capable of inhibiting aggregation of Aβ1-42 and disaggregation of preformed Aβ1-42 fibers.

Example 5

ACI-11-Ab-9 and ACI-12-Ab-11 Interactions

The interactions between antibodies ACI-11-Ab-9 and ACI-12-Ab-11 with amyloid peptide Aβ$_{1-42}$ is studied using surface plasmon resonance. The binding of the mouse antibody to either monomers or fibers of Aβ$_{1-42}$ is determined.

All SPR experiments are carried out on a Biacore X instrument (Biacore AB). Reagents for immobilization (EDC, NHS and ethanolamine), sensor chips CM5 and SA as well as running and sample buffer HBS-EP are purchased from Biacore AB. Sodium acetate (10 mM, pH 5.0) is used as coupling buffer to increase coupling yield. Fibrillar Aβ$_{1-42}$ (BAchem) is prepared by adding PBS buffer to Aβ$_{1-42}$ to a final concentration of 3 mg/ml and leaving the vials at 37° C. for 7 days. Fibrillar Aβ$_{1-42}$ is coupled to a CM5 sensor chip containing a surface-bound carboxymethyl dextran matrix. Biotinylated monomeric Aβ$_{1-42}$ (Bachem) is coupled to a Sensor chip SA consisting of carboxymethyl dextran matrix with covalently attached Streptavidin. Typically four or five concentrations of mAb are assayed by serial dilutions using running buffer. Injections are performed starting from the lowest concentration and are passed over both fc 1 and 2 at a flow rate of 30 µL/min for 3 min. Flow cell 2 is underivatised and responses are subtracted from fc 1 to correct for instrument noise and bulk refractive changes. After injection is finished, the surfaces are washed immediately with running buffer for 5 min. To remove remaining bound antibody from the Aβ$_{1-42}$ fibrils, surface regeneration is performed by injecting pulses of 10 mM NaOH. Kinetic analysis is performed using algorithms for numerical integration and global analysis using BIAevaluation 3.0. The curves obtained for injections of analyte at different concentrations are overlaid and the baselines adjusted to zero. For curve fitting, all data are fit simultaneously to a 1:1 homogeneous complex.

Binding of the mouse ACI-1-Ab-9 and ACI-12-Ab-11 antibodies to amyloid is determined.

Example 6

Binding of ACI-11-Ab-9 and ACI-12-Ab-11 Monoclonal Antibody to Amyloid Fibers

To analyze the molecular binding side of antibodies ACI-11-Ab-9 and ACI-12-Ab-11 on pre-formed fibers negatively contrasted transmission electronic microscopy (TEM) is performed.

The antibodies ACI-11-Ab-9 and ACI-12-Ab-11 are coupled with 8 nm colloidal gold according to Slot J W, Geuze H J (1985). For the co-incubation of amyloid 1-42 (Aβ1-42) fibers 6.65 µM fibers are incubated for 24 h at RT with the gold-labeled antibody with the molar ratio of 1:100. Subsequently 5 µl of sample are incubated on the fresh glow-discharged Cu grid (mesh 200) covered with parlodium/C film for 45 seconds, washed 3 times with water and 1 times with 2% fresh diluted and filtered uranyl acetate. Samples are stained in 2% uranyl acetate for 15-20 sec. Excess of stain on the grids is sucked and consequently air-dried. Three grids of each sample are prepared. The grids are analyzed in transmission electron microscopy Hitachi 7000.

Example 7

Fractionation by Density-Gradient Ultracentrifugation

The properties of monoclonal antibodies ACI-11-Ab-9 and ACI-12-Ab-11 in inhibiting Aβ$_{1-42}$ fiber polymerization and disaggregating of Aβ$_{1-42}$-fibers are studied by density-gradient ultracentrifugation (Rzepecki et al., 2004) which is based on the principle to distribute between differently sized resulting peptide fibers after incubation with and without antibodies followed by a SDS-PAGE sedimentation analysis on a preformed gradient (OptiPrep™). Simultaneous analysis of populations of preformed Aβ-fibers, disaggregation and inhibition of aggregation properties of the co-incubated antibodies, and the binding of the antibodies to the fibers are obvious advantages of this methods.

For the inhibition of Aβ$_{1-42}$ aggregation, Aβ$_{1-42}$ monomers are incubated with mAb ACI-11-Ab-9 and ACI-12-Ab-11, respectively, at two different molar ratios (molar ratio of monomer Aβ$_{1-42}$ thirty- or hundred-fold higher than mAb) with the Aβ final concentration of 50 µM. After 24 hrs incubation at 37° C., samples are overlayed over a discontinuous gradient of Optiprep™ and tubes are spun at 259 000 g for 3 hrs at 4° C. 15 fractions are harvested (140 µL each), fraction 1 is the least dense fraction from the top of the gradient and fraction 15 is the densest fraction from the bottom of the gradient. The pellet is also taken. The collected fractions are analyzed by SDS-PAGE with silver staining. The concentration Aβ$_{1-42}$ for inhibition assays is five times less than for disaggregation assays which decrease amyloid aggregation kinetic and ensure measurement within the linear phase.

For the disaggregation of preformed Aβ$_{1-42}$ fibrils by co-incubation with mAb ACI-11-Ab-9 and ACI-12-Ab-11 (at two different molar ratios 1:30 and 1:100, mAb+Monomer Aβ$_{1-42}$ with the Aβ final concentration of 246 µM), the samples are incubated for 24 hours at 37° C. After 24 hrs samples are fractioned by ultracentrifugation and separated by SDS-PAGE as described above and before (Rzepecki et al., 2004).

Example 8

Fluorescent Assay to Assess Inhibition of Aβ$_{1-42}$ Filament Aggregation and Disaggregation of Preformed Aβ$_{1-42}$ Filaments by Co-Incubation with mAb ACI-11-Ab-9 and ACI-12-Ab-11, Respectively BIS-ANS Fluorescent Assay To assess the inhibition properties of the mAb the BIS-ANS (LeVine, 2002) fluorescent assay is used which specifically detects the monomer or non-fibrillous population of Aβ$_{1-42}$ filaments. Before fluorescent measurement, Aβ$_{1-42}$ monomers are pre-incubated with either buffer, served as control, or mAb ACI-1-Ab-9 and ACI-12-Ab-11 (molar ratio 1:100, mAb vs. Aβ$_{1-42}$ peptide) for 14 hours at 37° C. Relative fluorescent units are automatically recorded and results are expressed as changes to the control in percentage.

Example 9

NMR and Fluorescence Characterization of the Interaction of ACI-11-Ab-9 and ACI-12-Ab-11 Monoclonal Antibody with $^{13}$C-Labeled β-Amyloid 1-42 Peptide To evaluate the potential mechanism by which the mAb solubilize pre-formed fibers or inhibit fiber formation, a headto-head-experiment between Th-T fluorescent assay and solid-state NMR of U-$^{13}$C Tyr10 and Val12-labeled β-amyloid 1-42 peptide is performed. Therefore the aim of this investigation is to follow the β-sheet transition by solid state NMR spectroscopy in the β-amyloid peptide and in the presence of the monoclonal antibody and to directly compare this with disaggregation capacity measured by Th-T fluorescent assay.

Solid-state NMR spectroscopy not only detects a transition in the secondary structure, but it also allows to localize the domains of the Aβ$_{1-42}$-peptide which dominate the structural transition. Solid-state NMR has proven its applicability to the problem as it has contributed to the structure determination of the Aβ$_{1-42}$-fibers (Petkova et al., 2004, Petkova et al., 2002). In particular the correlation of the $^{13}$C$_α$ and $^{13}$C$_β$ chemical shift with the secondary structure (Comilescu et al., 1999, Luca et al., 2001, Iwadate et al, 1999) is a valuable tool to test changes of the secondary structure within a peptide.

The synthesis of the peptide labeled including a $^{13}$C pre-labeled valine at position 12 ($^{12}$Val) and a $^{13}$C pre-labeled tyrosine at position 10 ($^{10}$Tyr) is performed by an Fmoc synthesis protocol. Identity and purity of the peptide are confirmed my MALDI mass spectroscopy. The labeled β-amyloid peptide (1-42) is used to generate fibers by incubating the peptide solution in PBS buffer for 1 week at 37° C. The major problem, the poor solubility of the amyloid β-peptide in PBS buffer, could be solved in the following manner: The pH value of the PBS buffer is temporarily increased by tiny amounts of ammonia to dissolve the amyloid β-peptide. The original pH value of the PBS buffer is re-obtained by incubating the sample in the presence of a bigger PBS bath using the volatile character of ammonia.

To measure the effect of the β-sheet breaking antibodies, solution of fibers are incubated with the antibody for 24 hours at 37° C. for both NMR and Th-T assay. For real-time comparison an aliquot of the same solution is used for Th-T fluorescent assay and the remaining solution is lyophilized for the NMR measurements.

The disaggregation capacities of ACI-11-Ab-9 and ACI-12-Ab-11 are analyzed by co-incubation with pre-formed 13C-labeled amyloid β-fibers using Th-T fluorescent assay.

To investigate the differences between PBS (control) and mAb incubation each spectrum is deconvoluted using PeakFit (http://www.systat.com/-products/PeakFit). The lines are well matched by employing a mixed Lorentzian/Gaussian fitting procedure.

Example 10

Functionality of ACI-11-Ab-9 and ACI-12-Ab-11 on Amyloid Fibers 12.1 Modification of Conformation of Aβ1-42 Fibers and Initiation of Disaggregation after Binding of the ACI-11-Ab-9 and ACI-12-Ab-11 Antibody In order to evaluate the mechanism by which the antibodies are capable to disaggregate preformed beta-amyloid (Aβ$_{1-42}$) fibers a head-to-head comparison of Thioflavin-T (Th-T) fluorescent assay is performed measuring disaggregation and solid-state Nuclear Magnetic Resonance (NMR) of U-$^{13}$C Tyrosine 10 and Valine 12-labelled Aβ1-42 peptide analysing secondary conformation.

Example 11

Epitope mapping of Monoclonal Antibodies ACI-11-Ab-9 and ACI-12-Ab-11

Epitope mapping of the monoclonal antibodies ACI-11-Ab-9 and ACI-12-Ab-11 was performed by ELISA using a peptide library comprising a total of 33 biotinylated peptides covering the complete amino acid (aa) sequence of Aβ1-42 (produced by Mimotopes, Clayton Victoria, Australia and purchased from ANAWA Trading SA, Wangen Switzerland). The peptides in the peptide library were composed of 8, 9 or 10-mer aa peptides. A biotinylated complete Aβ1-42 peptide (human sequence) was used as positive control (Bachem, Bubendorf, Switzerland). In addition, longer peptides covering Aβ1-28, Aβ17-40, Aβ1-40 and Aβ1-42 were used to define the broader region to which these antibodies may bind. These 4 peptides were also biotinlyated (manufactured by Anaspec and purchased from ANAWA Trading SA, Switzerland). Epitope mapping was done according to the manufacturer's (Mimotopes) instructions. Briefly, Streptavidin coated plates (NUNC, Roskilde, Denmark) were blocked with 0.1% BSA in PBS overnight at 4° C. After washing with PBS-0.05% Tween 20, plates were coated for 1 hour at RT with the different peptides from the library, diluted in 0.1% BSA, 0.1% Sodium Azide in PBS to a final concentration of 10 μM. After washing, plates were incubated for 1 hour at RT with the different antibodies, diluted to 10 μg/ml for antibodies ACI-1-Ab-9 and ACI-12-Ab-11 in 2% BSA, 0.1% Sodium Azide in PBS. Plates were washed again and incubated with alkaline phosphatase conjugated goat anti mouse IgG (Jackson Immunresearch West Grove, Pa., USA) for 1 h at RT. After final washing, plates were incubated with phosphatase substrate (PNPP, Sigma-Aldrich, St Louis, Mo., USA) and read after 3 hours of incubation at 405 nm using an ELISA plate reader.

ACI-11-Ab-9 was shown to bind significantly to Aβ1-42, but was unable to bind to any of the short peptides in the peptide library. It is therefore concluded, that the antibody needs more than 8 aa to bind the epitope and/or that ACI-11-Ab-9 may recognize a conformational epitope that is only present in the full length Aβ1-42.

ACI-12-Ab-11 also showed significant binding to Abl-42, but similarly to ACI-11-Ab-9, ACI-12-Ab-11 did not bind to any of the short peptides in the peptide library.

To determine whether antibodies ACI-11-Ab-9 and ACI-12-Ab-11 may recognize other Aβ peptides the binding to Aβ1-28, Aβ17-40, and Aβ1-40 and Aβ1-42 was evaluated.

ACI-1-Ab-9 showed considerable binding to Aβ1-28, Aβ1-40 and Aβ1-42, but did not show any binding to Aβ17-40.

Taken together, these results suggest that the epitope of ACI-11-Ab-9 lies in region 1-28 of Aβ and that the epitope is either longer than 8 aa and/or that the binding to Aβ is dependent on the conformation of Aβ.

ACI-12-Ab-11 showed significant binding to Abl-40 and Abl-42 but did not show any binding to Aβ1-28 or to Aβ17-40. Thus, ACI-12-Ab-11 could only bind to full-length Aβ1-40 and Aβ1-42 and not to any shorter peptides of Aβ. These results suggest that the epitope recognized by ACI-12-Ab-11 is dependent on the conformation of Aβ as even 24- or 28-mers of Aβ were insufficient for binding of the antibody.

Example 12

Influence of Passive Vaccination with ACI-11-Ab-9 and ACI-12-Ab-11 on Brain Amyloid Load in Single Transgenic hAPP Mice To assess the in vivo capacity of the ACI-11-Ab-9 and ACI-12-Ab-11 monoclonal antibodies to bind and clear soluble amyloid out of the brain, 6 month old single hAPP mice, gender and age matched, are used for a passive immunization study with different dose. Soluble Amyloid load is analyzed at the end of the study by harvesting the brain of the animals and by performing an Aβ 1-40 and Aβ 1-42 specific ELISA (TGC, Germany).

8-13 animals per group receive two injections at an interval of one week of 100, 300 and 1000 μg monoclonal antibody in 200 μl PBS whereas injection of PBS alone serves as control. One day after the second injection animals are sacrificed for biochemical analysis of soluble amyloid fraction. To quantify the amount of human Aβ 1-40 and human Aβ 1-42 in the soluble fraction of the brain homogenates and/or in cerebrospinal fluid (CSF), commercially available Enzyme-Linked-Immunosorbent-Assay (ELISA) kits are used (h Amyloid β 40 or β 42 ELISA high sensitive, TGC, Switzerland). The ELISA is performed according to the manufacturer's protocol. Briefly, standards (a dilution of synthetic Aβ 1-40 or Aβ 1-42) and samples are prepared in a 96-well polypropylene plate without protein binding capacity (Greiner, Germany). The standard dilutions with final concentrations of 1000, 500, 250, 125, 62.5, 31.3 and 15.6 pg/ml and the samples are prepared in the sample diluent, furnished with the ELISA kit, to a final volume of 60 μl. Since amyloid levels increase with the age of the mouse and since the actual evaluation requires that the readings of the samples are within the linear part of the standard curve, the samples for Aβ40 analysis are diluted 2:3, the samples for Aβ42 analysis are not diluted.

Samples, standards and blanks (50 μl) are added to the anti-Aβ-coated polystyrol plate (capture antibody selectively recognizes the C-terminal end of the antigen) in addition with a selective anti-Aβ-antibody conjugate (biotinylated detection antibody) and incubated overnight at 4° C. in order to allow formation of the antibody-Amyloid-antibody-complex. The following day, a Streptavidine-Peroxidase-Conjugate is added, followed 30 minutes later by the addition of a TMB/peroxide mixture, resulting in the conversion of the substrate into a colored product and the color intensity is measured by means of photometry with an ELISA-reader with a 450 nm filter. Quantification of the Aβ content of the samples is obtained by comparing absorbance to the standard curve made with synthetic Aβ 1-40 or Aβ 1-42. Data are expressed as individual changes to mean control value (in percent to control).

Example 13

Influence of Chronic Passive Administration of ACI-11-Ab-9 and ACI-12-Ab-11 on Plaque Load in Double Transgenic hAPPxPS1 Mice To assess the in vivo capacity of the ACI-11-Ab-9 and ACI-12-Ab-11 monoclonal antibodies to bind and reduce amyloid plaques in the brain, 3.5 month old double transgenic hAPPxPS1 mice, gender and age matched, are used for a 4 month long chronic passive immunization study. Amyloid plaques are analyzed at the end of the study by histochemistry of the brain of the animals by binding of Thioflavin S.

15 transgenic animals receive 16 weekly injections of 500 μg monoclonal antibody in PBS. 15 animals are injected with PBS alone, serving as controls. All injections are given intraperitoneally. At sacrifice, mice are anaesthetized and flushed trans-cardially with physiological serum at 4° C. to remove blood from the brain vessels. Subsequently, the brain is removed from the cranium and hindbrain and forebrain are separated with a cut in the coronal/frontal plane. The forebrain is divided evenly into left and right hemisphere by using a midline sagittal cut. One hemisphere is post-fixed overnight in 4% paraformaldehyde for histology. Sagittal vibratome sections (40 μm) are cut for free floating incubations and stored at 4° C. until staining in PBS with 0.1% sodium azide. Five sections at different levels are stained for dense plaques with Thioflavin S. Sections of all animals used are randomized for staining and blind quantification. Images are acquired with a Leica DMR microscope equipped with a Sony DXC-9100P camera and analyzed with a computer using Leica Q-Win software. Light intensity and condenser settings for the microscope are kept constant throughout the image acquisition process. All acquired images are subjected to the same computer subroutines to minimize investigator bias. Density slice thresholding is applied uniformly throughout analysis. The area of the subiculum is selected for automatic quantification of the amyloid load in the Thioflavin S staining.

Example 14

Influence of Passive Vaccination with ACI-11-Ab-9 and ACI-12-Ab-11 on Memory Capacity in Single Transgenic hAPP Mice To analyze the in vivo capacity of the ACI-11-Ab-9 and ACI-12-Ab-11 antibodies to modify or increase cognitive functionality, 9 month old single hAPP mice, gender and age matched, are used for passive immunization study. Non-spatial cognition is measured at the end of the immunization period assed by new Object Recognition Task (ORT).

12 animals per group receive two intra peritoneal injections of 400 μg monoclonal antibody in 200 μl PBS whereas injection of PBS alone serves as control. One day after the second injection cognitive capability are studied in a new Object Recognition Task (ORT)[12, 13]. For ORT enrollment mice are placed for 10 minutes into a behavioral arena and faced to a new unknown object. Exploration time is recorded. Three hours later the same animals are re-placed into the same arena for a $2^{nd}$ session but faced with the old, previously explored, and additionally with a new object. Again, exploration times for both objects are recorded and resulting cognition index is calculated as the ratio of exploration time for the new object related to total exploration time and expressed as proportional changes to the control.

Example 15

Binding of the Mouse Monoclonal Antibody to Proto-Fibrillar (PF) Oligomer Enriched Fractions of Aβ 1-42 Peptide Over Low-Molecular Weight (LMW) Monomers The binding of mouse anti-amyloid beta monoclonal antibodies to low molecular weight (LMW) monomer and high molecular weight proto-fibrillar (PF) preparations of Aβ1-42 peptide may be performed using ELISA.

Size exclusion chromatography (SEC) using 2 SEC columns, Superdex 75 HR 10/30 (Range 3-70 kDa) and Superose 6 HR 10/30 (Range 5-5,000 kDa), are used to prepare Aβ1-42 peptide fractions consisting of high-molecular weight (HMW) proto-fibrillar (PF) oligomer enriched and low-molecular weight (LMW) monomer preparations of Aβ1-42 peptide. The resulting eluates are then stained with uranyl acetate and are examined by high-resolution transmission electron microscopy (TEM) at 100 kV to verify the structural morphology of the eluted Aβ1-42 fractions.

An ELISA is then performed by coating the Aβ1-42 fractions onto high-binding assay plate at 2 μM over night. The coated plate is then blocked with 1.0% BSA and the ACI-24-Ab-3 (mouse EJ1A9) antibody is added in a serial dilution starting at 20 µg/ml. A serial dilution of a standard antibody (6E10, Chemicon) is also used. Anti-mouse IgG antibody conjugated to alkaline phosphatase and 4-nitrophenyl phosphate are used for detection of binding. Plates are read at 405 nm. All conditions are assayed in duplicate with coefficient of variation (CV)<0.2.

Example 16

Binding of ACI-12-Ab-11 Monoclonal Antibody (Clone FK2A6A6) to Monomer- and Oligomer-Enriched Fractions of the Aβ 1-42 Peptide The binding of the anti-Aβ antibody ACI-12-Ab-11 (clone: FK2A6A6) to monomers and oligomers of the Aβ1-42 peptide was assessed. Before being used in the study, the antibody was stored at −80° C. The Aβ1-42 peptide (W. M. Keck Facility, Yale University) was stored as lyophilized powder until the day of use. All other materials were from Sigma-Aldrich (Sigma-Aldrich Chemie GmbH, Buchs, Switzerland) unless otherwise indicated.

To prepare monomers and high molecular weight fractions with improved oligomer-enrichment of Aβ1-42 peptide, an improved methodology was used employing size exclusion chromatography (SEC). Two SEC columns, Supelco TSK G4000PW-XL (range: 10-1500 kDa; Sigma) and Superose 6 HR 10/30 (range 5-5,000 kDa; GE Healthcare Bio-Sciences AB Uppsala, Sweden), were used to prepare Aβ1-42 peptide fractions enriched in LMW monomer and high weight oligomer fractions. The resulting SEC eluates were then stained with uranyl acetate and examined by high-resolution transmission electron microscopy (TEM) at 100 kV to verify the structural morphology of the Aβ1-42 fractions (data not shown). To investigate the binding of the antibody to the Aβ1-42 fractions, an ELISA was performed. Aβ1-42 fractions were coated onto high-binding assay plates at 2.2 µM in PBS for 2 hrs. The coated plates were then washed five times with 0.05% Tween-20 in PBS and blocked with 1.0% BSA. Anti-Aβ antibodies, including the control antibody (6E10) were added in a serial dilution starting at indicated concentrations. Anti-mouse IgG antibody conjugated to alkaline phosphatase (Jackson ImmunoResearch, Suffolk, England), and 4-nitrophenyl phosphate was used for detection of binding. Plates were read at 405 nm following a 14 hr incubation at room temperature. The assay was repeated three times.

Figure 1:
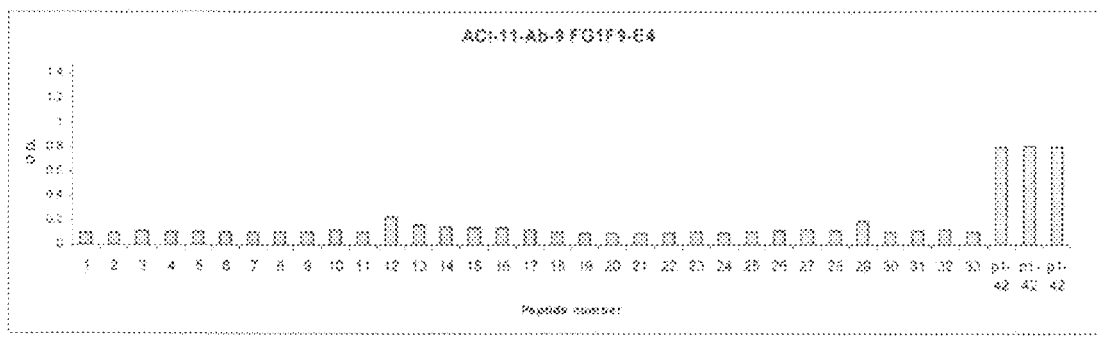
Figure 2:
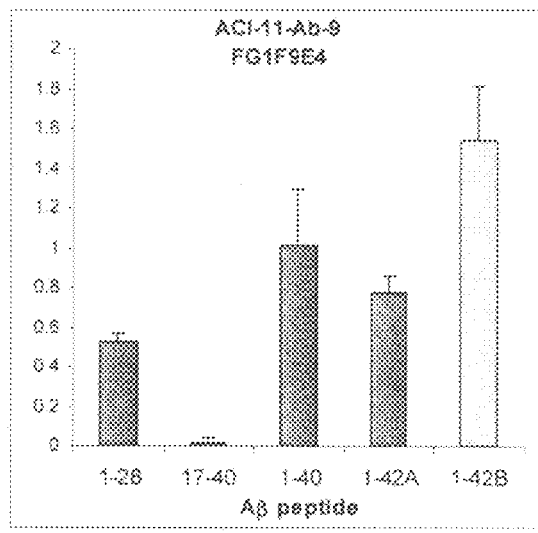
Figure 3:
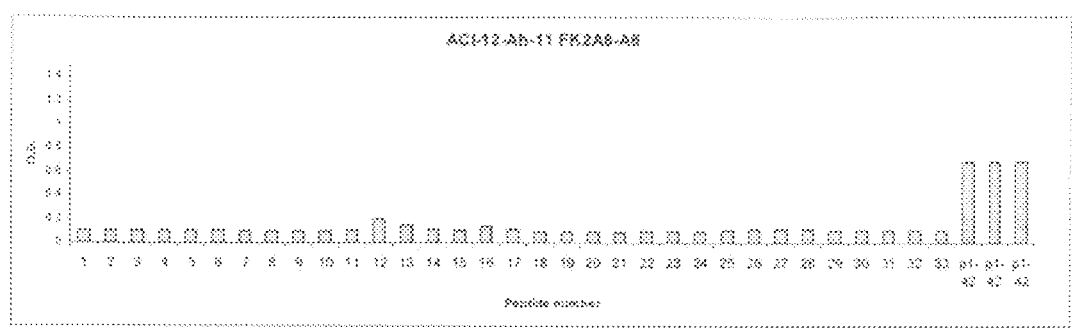
Figure 4:
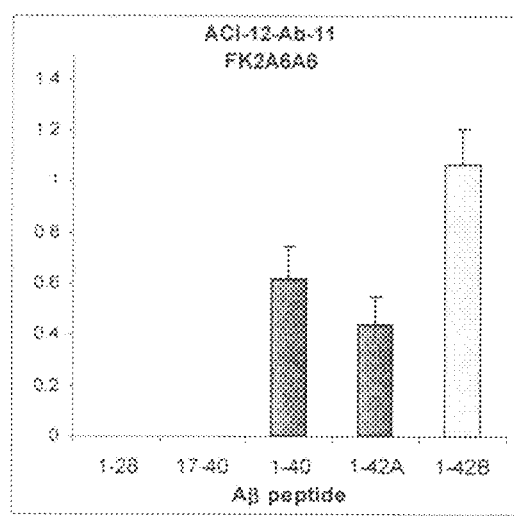
Figure 5:
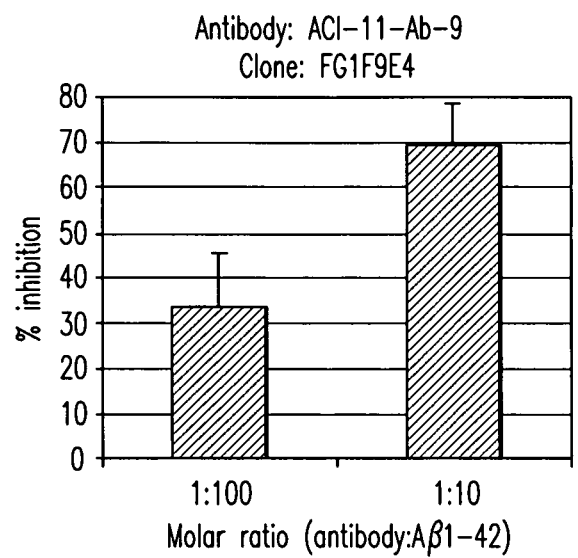
FIG. 5 depicts the ACI-11-Ab-9-mediated inhibition of Aβ1-42 aggregation at a 1:100 and 1:10 antibody to Aβ1-42 molar ratio. Results show mean±1 standard error of 2 independent experiments.
Figure 6:
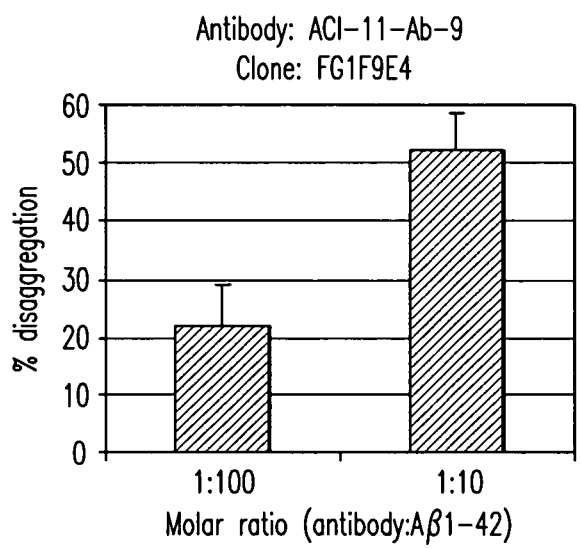
FIG. 6 depicts the ACI-11-Ab-9-mediated disaggregation of pre-aggregated Aβ1-42 at a 1:100 and 1:10 antibody to Aβ1-42 molar ratio. Results show mean±1 standard error of 3 independent experiments.
Figure 7:
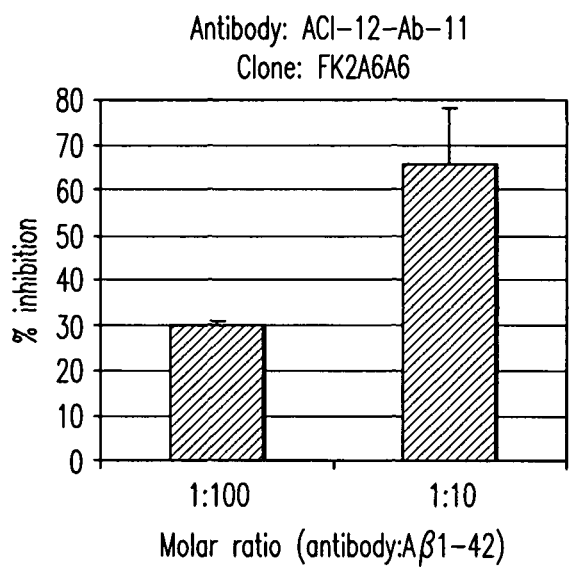
FIG. 7 depicts the ACI-12-Ab-1'-mediated inhibition of Aβ1-42 aggregation at a 1:100 and 1:10 antibody to Aβ1-42 molar ratio. Results show mean±1 standard error of 2 independent experiments.
Figure 8:
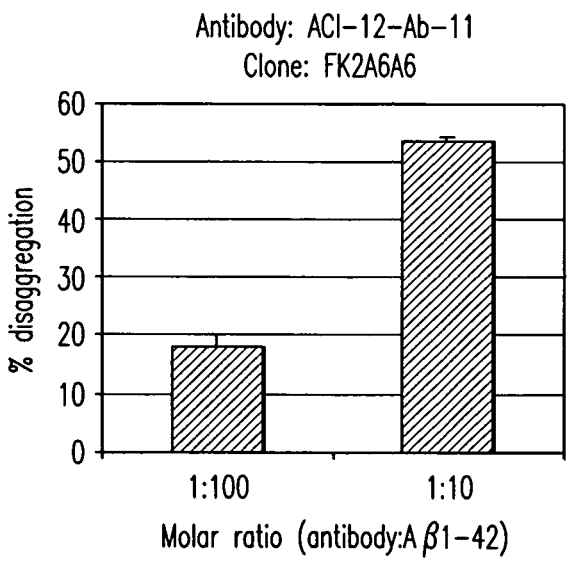
FIG. 8 depicts the ACI-12-Ab-11-mediated disaggregation of pre-aggregated Aβ1-42 at a 1:100 and 1:10 antibody to Aβ1-42 molar ratio. Results show mean±1 standard error of 2 independent experiments.
Figure 9A:
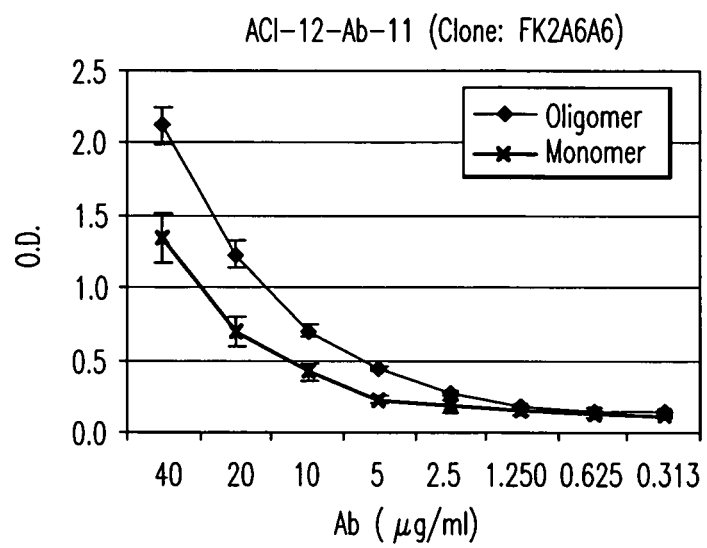
FIG. 9 depicts the binding of ACI-12-Ab-11 antibody (A) and control antibody 6E10 (B) to monomers and oligomers of the Aβ1-42 peptide. The results are reported as mean (±SEM) optical density (O.D.) values of three independent experiments.
Figure 9B:
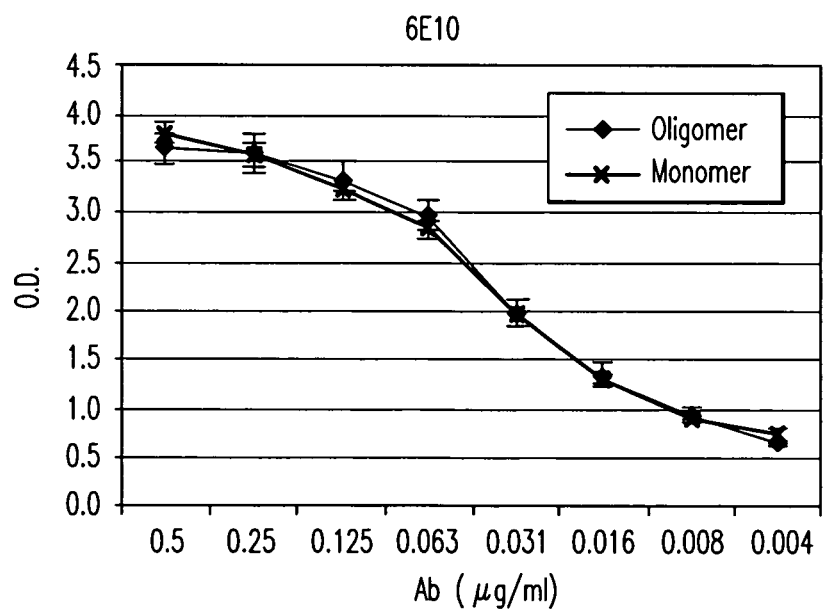

FIG. 9 shows the mean (±SEM) optical density (O.D.) values obtained from the three separate ELISA assays. Antibody ACI-12-Ab-11 demonstrated superior binding to the Aβ1-42 fraction enriched in oligomers as compared to the fraction not enriched in oligomers and consisting primarily of Aβ1-42 monomers (FIG. 9A). In comparison, the control antibody 6E10 bound equally well to both Aβ1-42 fractions (FIG. 9B). Tables 4 and 5 show the O.D. values obtained in ELISA assays 1, 2, and 3, for antibodies ACI-12-Ab-11 and 6E10, respectively.

These results indicate that the antibody ACI-12-Ab-11 (clone: FK2A6A6) shows superior binding affinity to oligomer-enriched fractions of Aβ1-42 than it does to monomeric Aβ1-42.

Example 17

Inhibition of Aβ$_{42}$-ApoE4 Binding

The binding of ApoE4 to amyloid and the capacity of the monoclonal antibodies according to the invention to inhibit the interaction between ApoE4 and Aβ$_{42}$ peptide are assessed.

Human recombinant ApoE4 is diluted to 200 nM with PBS, and stored in 0.5 ml aliquots at −80° C. 1 mg of Aβ$_{42}$-biotin peptide is resuspended in 20 µl of DMSO and then in 1980 µl of PBS/0.1% BSA/0.1% sodium azide to obtain a final solution of 0.5 mg/ml. An ELISA assay is used to determine the binding of rhApoE4 to Aβ$_{42}$. rhApoE4 (100 nM) is incubated for 3 hrs at 37° C. with Aβ$_{42}$-biotin (1 µM) to allow the binding of the protein to the peptide. The mixture is applied on a streptavidin-coated plate previously washed 3 times with PBST (PBS+0.05% Tween 20). After 1 h incubation at room temperature (RT) the plate is washed 3 times with PBST and blocked overnight at 4° C. with PBS containing 0.1% BSA. Bound ApoE4 is detected with an IgG1 mouse anti-human ApoE antibody used at a dilution of 1:3000 in PBS and applied on the plate for 2.5 hrs at RT. The plate is washed 4 times with PBST and then incubated 1 hour at RT with the detection antibody, an anti-mouse IgG coupled to Alkaline Phosphatase (AP) at a dilution of 1:5000 in PBS. After a final wash with 4×PBST, plates are incubated for 5.5 hrs with AP substrate pNPP (Phosphatase substrate, 4-Nitrophenyl phosphate Disodium salt Hexahydrate) and read at 405 nm using an ELISA plate reader. FIG. 10 summarizes the experiment.

The ELISA assay is developed by making 8 times 2-fold dilutions of a mix of rhApoE4 (150 nM) and Aβ$_{42}$-biotin (1.5 µM). The following negative controls are added: (1) rhApoE4 alone; (2) Aβ$_{42}$-biotin; and (3) rhApoE4-Aβ$_{42}$-biotin (protocol without mouse anti-ApoE4). FIG. 11 shows that a positive signal is obtained only when both rhApoE4 and Aβ$_{42}$-biotin are present and the complete ELISA protocol is followed.

To optimize the concentrations of rhApoE4 and Aβ$_{42}$-biotin in the assay, dilutions of rhApoE4 (e.g., 150 nM) are tested with a constant concentration of Aβ$_{42}$-biotin (e.g., normal: 1.5 µM or excess: 15 µM). FIG. 12 shows that an excess of Aβ$_{42}$-biotin dilutes the signal of the ELISA assay as less Aβ$_{42}$-biotin complexed to rhApoE4 binds to the plate. Based on this test an optimal concentration of rhApoE4 is selected.

The concentration of Aβ$_{42}$-biotin in the assay is optimized using a constant concentration of rhApoE4 of 100 nM. Dilutions of Aβ$_{42}$-biotin (e.g., with a starting concentration of 1.5 µM (diluted to lower concentrations, for example as low as 1500 nM)) are tested in the ELISA set-up. Based on the results shown in FIG. 13, an optimal concentration of 1 µM of Aβ$_{42}$-biotin is selected to determine the effect of the monoclonal antibodies on the binding of rhApoE4 to Aβ$_{42}$-biotin.

The effect of one or more of the antibodies of the invention on the binding of rhApoE4 to Aβ$_{42}$-biotin is assessed using the above-described ELISA assay, but further including the antibody of the invention in the binding mixture prior to plating. For example, two-fold dilutions of the antibody may be used, starting at a concentration of 50 µg/mL. The inclusion of the antibody may be at the time when ApoE4 and Aβ$_{42}$-biotin are first combined, or it may be after (e.g., several hours after) the ApoE4 and Aβ$_{42}$-biotin were first combined. In the former instance, the ability of the antibody of the invention to prevent or inhibit the interaction of ApoE4 and Aβ$_{42}$-biotin is assessed, whereas in the latter instance, the ability of the antibody of the invention to disrupt a preexisting complex between ApoE4 and Aβ$_{42}$-biotin is assessed.

Tables

Antigens Used to Raise Mouse Monoclonal Antibodies

TABLE 1

Antibodies and antigenic constructs used for raising said antibodies

| Mouse mAb | Clone | Antigen/Sequence | Linker | Anchor | Adjuvant |
|---|---|---|---|---|---|
| ACI-11-Ab-9 | FG1F9E4 | Aβ$_{22-35}$ | PEG | DSPE | Lipid A |
| ACI-12-Ab-11 | FK2A6A6 | Aβ$_{29-40}$ | PEG | DSPE | Lipid A |

TABLE 2

Binding of Aβ peptides to ACI-11-Ab-9 and ACI-12-Ab-11. Results are expressed as O.D. after background subtraction.

| Peptide | | Antibody ACI-11-Ab-9 | Antibody ACI-12-Ab-11 |
|---|---|---|---|
| 1-28[1] | Mean | 0.53 | −0.02 |
| | SD | 0.06 | 0.00 |
| | SEM | 0.04 | 0.00 |
| 17-40[1] | Mean | 0.02 | −0.02 |
| | SD | 0.04 | 0.01 |
| | SEM | 0.03 | 0.00 |
| 1-40[1] | Mean | 1.02 | 0.62 |
| | SD | 0.39 | 0.18 |
| | SEM | 0.27 | 0.13 |
| 1-42A[1] | Mean | 0.78 | 0.44 |
| | SD | 0.12 | 0.15 |
| | SEM | 0.08 | 0.11 |
| 1-42B[2] | Mean | 1.54 | 1.07 |
| | SD | 0.38 | 0.20 |
| | SEM | 0.27 | 0.14 |

[1]Peptide from Anaspec
[2]Peptide from Bachem

TABLE 3

Binding of ACI-11-Ab-9 and ACI-12-Ab-11 to 33 overlapping peptides of Aβ 1-42 as analyzed by ELISA.

| Peptide | Antibody ACI-11-Ab-9 | Antibody ACI-12-Ab-11 |
|---|---|---|
| 1 | 0.10 | 0.10 |
| 2 | 0.10 | 0.10 |
| 3 | 0.12 | 0.11 |
| 4 | 0.11 | 0.10 |
| 5 | 0.11 | 0.10 |
| 6 | 0.11 | 0.10 |
| 7 | 0.11 | 0.10 |
| 8 | 0.11 | 0.10 |
| 9 | 0.11 | 0.10 |
| 10 | 0.13 | 0.10 |
| 11 | 0.11 | 0.11 |
| 12 | 0.24 | 0.21 |
| 13 | 0.17 | 0.15 |
| 14 | 0.16 | 0.12 |
| 15 | 0.14 | 0.10 |
| 16 | 0.14 | 0.14 |
| 17 | 0.13 | 0.12 |
| 18 | 0.11 | 0.10 |
| 19 | 0.10 | 0.10 |
| 20 | 0.10 | 0.10 |
| 21 | 0.10 | 0.09 |
| 22 | 0.10 | 0.10 |
| 23 | 0.11 | 0.10 |
| 24 | 0.10 | 0.10 |
| 25 | 0.11 | 0.11 |
| 26 | 0.12 | 0.12 |
| 27 | 0.13 | 0.12 |
| 28 | 0.12 | 0.11 |
| 29 | 0.20 | 0.11 |
| 30 | 0.11 | 0.11 |
| 31 | 0.12 | 0.11 |
| 32 | 0.12 | 0.11 |
| 33 | 0.11 | 0.11 |
| Aβ1-42 | 0.80 | 0.69 |
| Aβ1-42 | 0.81 | 0.69 |
| Aβ1-42 | 0.80 | 0.69 |

TABLE 4

Binding of ACI-12-Ab-11 (clone: FK2A6A6) to Monomer- and Oligomer-Enriched Preparations of the Aβ 1-42 Peptide

| Antibody dilution[b] | Monomers (O.D.)[a] | | | | | Oligomers (O.D.)[a] | | | | |
|---|---|---|---|---|---|---|---|---|---|---|
| | Assay 1 | Assay 2 | Assay 3 | Mean | SEM | Assay 1 | Assay 2 | Assay 3 | Mean | SEM |
| 1:1 | 1.60 | 1.04 | 1.37 | 1.34 | 0.16 | 2.24 | 1.85 | 2.27 | 2.12 | 0.14 |
| 1:2 | 0.85 | 0.51 | 0.75 | 0.70 | 0.10 | 1.33 | 1.04 | 1.32 | 1.23 | 0.10 |
| 1:4 | 0.53 | 0.30 | 0.45 | 0.43 | 0.07 | 0.70 | 0.64 | 0.80 | 0.71 | 0.05 |
| 1:8 | 0.29 | 0.18 | 0.25 | 0.24 | 0.03 | 0.44 | 0.42 | 0.47 | 0.44 | 0.02 |
| 1:16 | 0.25 | 0.12 | 0.18 | 0.18 | 0.04 | 0.30 | 0.25 | 0.28 | 0.28 | 0.01 |
| 1:32 | 0.19 | 0.10 | 0.14 | 0.14 | 0.03 | 0.20 | 0.16 | 0.20 | 0.18 | 0.01 |
| 1:64 | 0.15 | 0.09 | 0.13 | 0.12 | 0.02 | 0.19 | 0.14 | 0.16 | 0.16 | 0.01 |
| 1:128 | 0.14 | 0.09 | 0.12 | 0.12 | 0.02 | 0.16 | 0.14 | 0.15 | 0.15 | 0.01 |

[a]O.D.: optical density at 405 nm
[b]Starting dilution for ACI-12-Ab-11 (clone: FK2A6A6) was 40 μg/ml

TABLE 5

Binding of the 6E10 control antibody to Monomer- and Oligomer-Enriched Preparations of the Aβ 1-42 Peptide

| Antibody dilution[b] | Monomers (O.D.)[a] | | | | | Oligomers (O.D.)[a] | | | | |
|---|---|---|---|---|---|---|---|---|---|---|
| | Assay 1 | Assay 2 | Assay 3 | Mean | SEM | Assay 1 | Assay 2 | Assay 3 | Mean | SEM |
| 1:1 | 3.67 | 3.77 | 4.04 | 3.83 | 0.11 | 3.36 | 3.67 | 3.89 | 3.64 | 0.15 |
| 1:2 | 3.30 | 3.48 | 4.00 | 3.59 | 0.21 | 3.39 | 3.55 | 3.83 | 3.59 | 0.13 |
| 1:4 | 3.00 | 3.29 | 3.52 | 3.27 | 0.15 | 3.10 | 3.37 | 3.64 | 3.37 | 0.16 |
| 1:8 | 2.67 | 3.00 | 2.80 | 2.82 | 0.10 | 2.73 | 2.99 | 3.23 | 2.98 | 0.15 |
| 1:16 | 1.78 | 1.94 | 2.23 | 1.98 | 0.13 | 1.78 | 1.92 | 2.07 | 1.92 | 0.08 |
| 1:32 | 1.18 | 1.34 | 1.54 | 1.36 | 0.10 | 1.27 | 1.30 | 1.40 | 1.32 | 0.04 |
| 1:64 | 0.81 | 0.94 | 1.08 | 0.94 | 0.08 | 0.93 | 0.88 | 0.95 | 0.92 | 0.02 |
| 1:128 | 0.64 | 0.75 | 0.86 | 0.75 | 0.06 | 0.62 | 0.61 | 0.66 | 0.63 | 0.02 |

[a]O.D.: optical density at 405 nm
[b]Starting dilution for 6E10 was 0.5 μg/ml

DEPOSITS

The following hybridoma cell lines were deposited with the "Deutsche Sammlung von Mikroorganismen und Zellkulturen GmbH (DSMZ) in Braunschweig, Mascheroder Weg 1 B, 38124 Branuschweig, under the provisions of the Budapest Treaty:

| Hybridoma line designation | Antibody designation | Deposition date | Accession No |
|---|---|---|---|
| FG1F9E4 | ACI-11-Ab-9 | May 25, 2007 | DSM ACC2845 |
| FK2A6A6 | ACI-12-Ab-11 | May 25, 2007 | DSM ACC2846 |

REFERENCES

Bard F, Cannon C, Barbour R, Burke R L, Games D, Grajeda H, Guido T, Hu K, Huang J, Johnson-Wood K, Khan K, Kholodenko D, Lee M, Lieberburg I, Motter R, Nguyen M, Soriano F, Vasquez N, Weiss K, Welch B, Seubert P, Schenk D, Yednock T. (2000). Nature Med. 6, 916-919.

Barghorn S, Nimmrich V, Striebinger A, Krantz C, Keller P, Janson B, Bahr M, Schmidt M, Bitner R S, Harlan J, Barlow E, Ebert U, Hillen H (2005) Globular amyloid beta-peptide oligomer—a homogenous and stable neuropathological protein in Alzheimer's disease. J Neurochem 95:834-847.

Baschong W, Wrigley N G (1990) Small colloidal gold conjugated to Fab fragments or to immunoglobulin G as high-resolution labels for electron microscopy: a technical overview. J Electron Microsc Tech 14:313-323.

Blond and Goldberg, 1987, PNAS Mar. 1, 1987 Vol. 84|no. 5|1147-1151

Comilescu G, Delaglio F, Bax A. (1999) J. Biomol. NMR; 13: 289-302.

Burdick, D. et al. Assembly and aggregation properties of synthetic Alzheimer's A4/beta amyloid peptide analogs. *J. Biol. Chem.* 267, 546-554 (1992).

DeMattos, Bales, K R, Cummins, D J, Dodart, J C, Paul, S M, Holtzmann, D. M (2001). Proc Natl Acad Sci USA 98, 8850-8855.

Dewachter I, Van D J, Smeijers L, Gilis M, Kuiperi C, Laenen I, Caluwaerts N, Moechars D, Checker F, Vanderstichele H, Van L F (2000) Aging increased amyloid peptide and caused amyloid plaques in brain of old APP/V7171 transgenic mice by a different mechanism than mutant presenilin1. J Neurosci 20:6452-6458.

Dewachter I, Reverse D, Caluwaerts N, R is L, Kuiperi C, Van den HC, Spittaels K, Umans L, Serneels L, Thiry E, Moechars D, Mercken M, Godaux E, Van Leuven F (2002) Neuronal deficiency of presenilin 1 inhibits amyloid plaque formation and corrects hippocampal long-term potentiation but not a cognitive defect of amyloid precursor protein [V7171] transgenic mice. J Neurosci 22:3445-3453.

Glenner and Wong, Biochem Biophys Res Comm 129, 885-890 (1984)

Harlow and Lane (Antibodies: A Laboratory Manual (Cold Spring Harbor Laboratory, New York 1988))

Heneka M T, Sastre M, Dumitrescu-Ozimek L, Dewachter I, Walter J, Klockgether T, Van L F (2005) Focal glial activation coincides with increased BACE1 activation and precedes amyloid plaque deposition in APP[V7171] transgenic mice. J Neuroinflammation 2:22.

Hodgson et al., Bio/Technoloy, 9:421 (1991)

Iwadate M, Asakura T, Williamson M P. (1999) J. Biomol. NMR; 13: 199-211.

Kirschner, D. A., Abraham, C., & Selkoe, D. J. X-ray diffraction from intraneuronal paired helical filaments and extraneuronal amyloid fibers in Alzheimer disease indicates cross-beta conformation. *Proc. Natl. Acad. Sci. U.S.A* 83, 503-507 (1986).

Khaw, B. A. et al. J. Nucl. Med. 23:1011-1019 (1982)

Kennedy, J. H., et al., 1976 (Clin. Chim. Acta 70:1-31)

Klein W L (2002) Abeta toxicity in Alzheimer's disease: globular oligomers (ADDLs) as new vaccine and drug targets. Neurochem Int 41(5):345-352.

Kohler and Milstein (Nature 256: 495-497 (1975))

LeVine, H. III, (2002). Arch Biochem Biophys 404, 106-115.

Luca et al., 2001

McGeer et al., 1994

Moechars D, Dewachter I, Lorent K, Reverse D, Baekelandt V, Naidu A, Tesseur I, Spittaels K, Haute C V, Checker F, Godaux E, Cordell B, Van L F (1999) Early phenotypic changes in transgenic mice that overexpress different mutants of amyloid precursor protein in brain. J Biol Chem 274:6483-6492.

Nelson, R. & Eisenberg, D. Recent atomic models of amyloid fibril structure. *Curr. Opin. Struct. Biol.* (2006).

Nicolau, C., Greferath, R., Balaban, T. S., Lazarte, J. E., and Hopkins, R. J. (2002). Proc Natl Acad Sci USA 99, 2332-2337.

Queen et al., Proc. Natl. Acad Sci USA, 86:10029-10032 (1989)

Pearson W. R. (1990), Methods in Enzymology 183, 63-98

Petkova A T, Buntkowsky G, Dyda F, Leapman R D, Yau W M, Tycko R. J. Mol. Biol. 2004; 335: 247-260.

Petkova A T, Ishii Y, Balbach J J, Antzutkin O N, Leapman R D, Delaglio F, Tycko R. (2002) Proc. Nat. Acad. Sci.U.S.A; 99: 16742-16747.

Rousseaux et al. Methods Enzymology, 121:663-69, Academic Press, 1986

Rzepecki, P., Nagel-Steger, L., Feuerstein, S., Linne, U., Molt, O., Zadmard, R., Aschermann, K., Wehner, M., Schrader, T. and Riesner, D. (2004). J Biol Chem 279, 47497-47505.

Sambrook et al. Molecular Biology: A Laboratory Manual, Cold Spring Harbor Press, Cold Spring Harbor, N.Y., 1989.

Schenk D, Barbour R, Dunn W, Gordon G, Grajeda H, Guido T, Hu K, Huang J, Smith, S. O., and Bormann, B. J. (1995). Proc Natl Acad Sci USA 92, 488-491.

Schenk et al., 1999

Schurs, A. H. W. M., et al. 1977 (Clin. Chim Acta 81:1-40

Slot J W, Geuze H J (1985) A new method of preparing gold probes for multiple-labeling cytochemistry. Eur J Cell Biol 38:87-93.

Smith and Waterman, Advances in Applied Mathematics 2 (1981), 482-489

Van dA, I, Wera S, Van L F, Henderson S T (2005) A ketogenic diet reduces amyloid beta 40 and 42 in a mouse model of Alzheimer's disease. Nutr Metab (Lond) 2:28.

Wagner et al (2002) Journal of Liposome Research Vol 12(3), pp 259-270

Ye, J., Dave, U. P., Grishin, N. V., Goldstein, J. L., and Brown, M. S. (2000). Proc Natl Acad Sci USA 97, 5123-5128.

Zrein et al. (1998), Cininical and Diagnostic Laboratory Immunology, 5(1): 45-49.

Experimental Eye Research 78 (2004) 243-256

WO 2004/058258

WO96/1359

WO96/29605

---

The invention claimed is:

1. A monoclonal antibody, or an active fragment thereof, which is produced by hybridoma cell line FG1F9E4, deposited on May 25, 2007 and given deposit number DSM ACC2845.

2. A monoclonal antibody, or an active fragment thereof, which is produced by hybridoma cell line FK2A6A6, deposited on May 25, 2007 and given deposit number DSM ACC2846.

3. An anti-amyloid beta antibody, or active fragment thereof, wherein
   i. CDR1 of the light chain variable region has the amino acid sequence of SEQ ID NO:11;
   ii. CDR2 of the light chain variable region has the amino acid sequence of SEQ ID NO:12;
   iii. CDR3 of the light chain variable region has the amino acid sequence of SEQ ID NO:13; and
   iv. at least one CDR of the heavy chain variable region has an amino acid sequence selected from the group consisting of SEQ ID NO:14, SEQ ID NO:15 and SEQ ID NO:16.

4. An anti-amyloid beta antibody, or active fragment thereof, wherein
   i. CDR1 of the heavy chain variable region has the amino acid sequence of SEQ ID NO:14;
   ii. CDR2 of the heavy chain variable region has the amino acid sequence of SEQ ID NO:15; and
   iii. CDR3 of the heavy chain variable region has the amino acid sequence of SEQ ID NO:16.

5. An anti-amyloid beta antibody, or active fragment thereof, wherein
   i. CDR1 of the light chain variable region has the amino acid sequence of SEQ ID NO:11;
   ii. CDR2 of the light chain variable region has the amino acid sequence of SEQ ID NO:12;
   iii. CDR3 of the light chain variable region has the amino acid sequence of SEQ ID NO:13;
   iv. CDR1 of the heavy chain variable region has the amino acid sequence of SEQ ID NO:14;
   v. CDR2 of the heavy chain variable region has the amino acid sequence of SEQ ID NO:15; and
   vi. CDR3 of the heavy chain variable region has the amino acid sequence of SEQ ID NO:16.

6. A therapeutic composition comprising the monoclonal antibody, or active fragment thereof, according to claim 1, 2, 3, 4, or 5.

7. The composition of claim 6, further comprising a biologically active substance selected from the group consisting of an anti-apoptotic compound, a metal chelator, an inhibitor of DNA repair, 3-amino-1-propanesulfonic acid (3APS), 1,3-propanedisulfonate (1,3PDS), a secretase activator, a β-secretase inhibitor, a γ-secretase inhibitor, a tau protein, a neurotransmitter, a β-sheet breaker, an anti-inflammatory molecule, and a cholinesterase inhibitor.

8. The composition of claim 7, wherein the inhibitor of DNA repair is pirenzepin or a metabolite thereof.

9. The composition of claim 7, wherein the cholinesterase inhibitor is tacrine, rivastigmine, donepezil, galantamine or a nutritive supplement.

10. The therapeutic composition of claim 6 comprising one or more of a pharmaceutically acceptable carrier, a diluent or an excipient.

11. A test kit comprising the monoclonal antibody, or active fragment thereof, of claim 1, 2, 3, 4, or 5, and optionally further comprising instructions for using the monoclonal antibody, or active fragment thereof, for the purpose of binding to amyloid protein to form an immunological complex and detecting the formation of the immunological complex such that presence or absence of the immunological complex correlates with presence or absence of amyloid protein.

12. A cell line characterized in that it produces a monoclonal antibody, or active fragment thereof, of claim 1, 2, 3, 4, or 5.

* * * * *